United States Patent
Therien et al.

(10) Patent No.: US 11,508,462 B2
(45) Date of Patent: Nov. 22, 2022

(54) CONTROL OF TRION DENSITY IN CARBON NANOTUBES FOR ELECTRO-OPTICAL AND OPTO-ELECTRIC DEVICES

(71) Applicant: DUKE UNIVERSITY, Durham, NC (US)

(72) Inventors: Michael Therien, Durham, NC (US); Yusong Bai, Durham, NC (US); Jean-Hubert Olivier, Durham, NC (US); George Bullard, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 914 days.

(21) Appl. No.: 16/222,704

(22) Filed: Dec. 17, 2018

(65) Prior Publication Data

US 2019/0189249 A1    Jun. 20, 2019

Related U.S. Application Data

(60) Provisional application No. 62/599,188, filed on Dec. 15, 2017.

(51) Int. Cl.
| | |
|---|---|
| *G16C 10/00* | (2019.01) |
| *G16C 20/40* | (2019.01) |
| *G16C 60/00* | (2019.01) |
| *C01B 32/174* | (2017.01) |
| *C01B 32/17* | (2017.01) |

(Continued)

(52) U.S. Cl.
CPC ............. *G16C 10/00* (2019.02); *C01B 32/17* (2017.08); *C01B 32/174* (2017.08); *G16C 20/40* (2019.02); *G16C 60/00* (2019.02); *H01L 51/0049* (2013.01); *B82Y 10/00* (2013.01); *B82Y 20/00* (2013.01); *B82Y 30/00* (2013.01); *C01B 32/159* (2017.08); *C01B 2202/02* (2013.01); *C01B 2202/22* (2013.01); *C01B 2202/30* (2013.01); *G06F 17/13* (2013.01)

(58) Field of Classification Search
CPC ........ G16C 10/00; G16C 20/40; G16C 60/00; C01B 32/17; C01B 32/174; C01B 32/159; C01B 2202/02; C01B 2202/22; C01B 2202/30; H01L 51/0049; B82Y 10/00; B82Y 20/00; B82Y 30/00; G06F 17/13
See application file for complete search history.

(56) References Cited

U.S. PATENT DOCUMENTS

| | | | |
|---|---|---|---|
| 2017/0322081 A1* | 11/2017 | Wang | C09K 11/06 |
| 2018/0265779 A1* | 9/2018 | Wang | B82Y 15/00 |
| 2020/0013991 A1* | 1/2020 | Wang | G01N 21/75 |

OTHER PUBLICATIONS

Deria, et al., Potentiometric, Electronic, and Transient Absorptive Spectroscopic Properteis of Oxidized Single-Walled Carbon Nanotubes Helically Wrapped by Ionic, Semiconducting Polymers in Aqueous and Organic Media, J. Am. Chem. Soc. 2014; 136:14193-14199 (Year: 2014).*

(Continued)

*Primary Examiner* — Daniel C. McCracken
(74) *Attorney, Agent, or Firm* — Talem IP Law, LLP

(57) ABSTRACT

An optoelectronic system can include a single walled carbon nanotube (SWNT) device. The SWNT can include a carrier-doping density with optical conditions that control trion formation that respond via optical, electrical, or magnetic stimuli. The carrier-doping density can include a hole-polaron or electron-polaron concentration.

10 Claims, 31 Drawing Sheets

(51) Int. Cl.
*H01L 51/00* (2006.01)
*G06F 17/13* (2006.01)
*C01B 32/159* (2017.01)
*B82Y 30/00* (2011.01)
*B82Y 20/00* (2011.01)
*B82Y 10/00* (2011.01)

(56) References Cited

OTHER PUBLICATIONS

Santos, Silvia et al., "All-Optical Trion Generation in Single Walled Carbon Nanotubes", Phys. Rev. Lett., Oct. 2011, 13 pages, vol. 107, Issue 18, American Physical Society, https://link.aps.org/doi/10.1103/PhysRevLett.107.187401.

Eremin, T.V. et al., "Spectroscopic signatures of many-particle energy levels in non-covalently doped single-wall carbon nanotubes", 2018, 8 pages, https://www.researchgate.net/publication/324981902_Spectroscopic_signatures_of_many-particle_energy_levels_in_non-covalently_doped_single-wall_carbon_nanotubes.

Möhl, Charles et al., "Trion-Polariton Formation in Single-Walled Carbon Nanotube Microcavities", ACS Photonics, May 8, 2018, pp. 2074-2080, vol. 5, Issue 6, American Chemical Society.

* cited by examiner

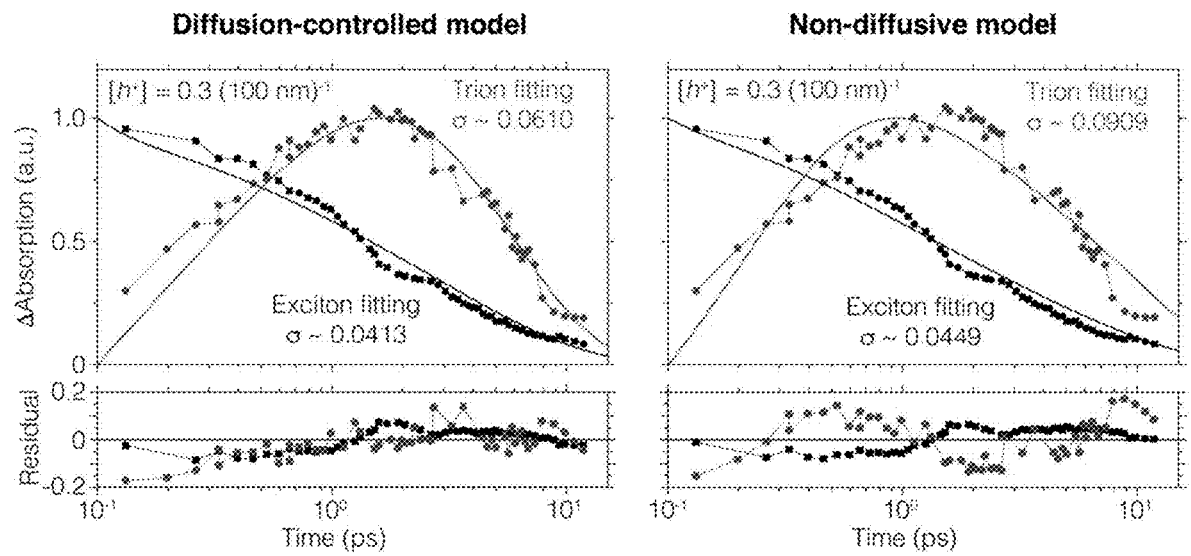
Figure 31A  Figure 31B
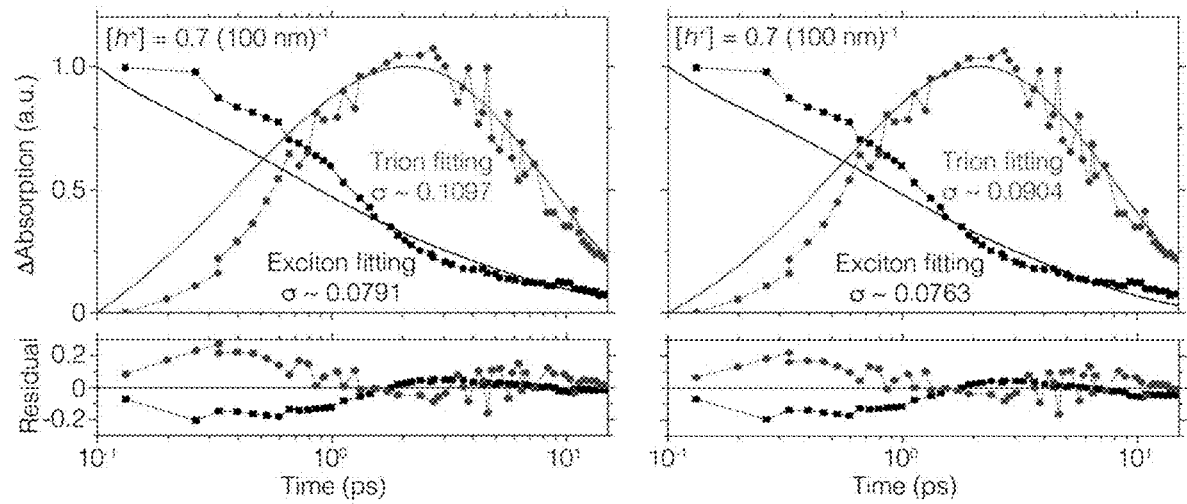
Figure 31C  Figure 31D

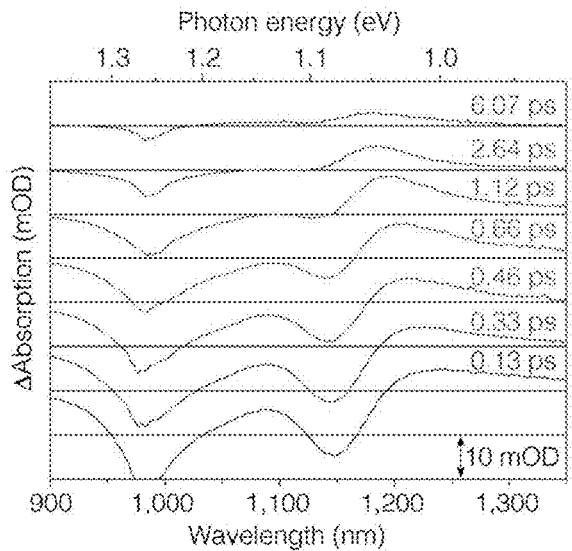 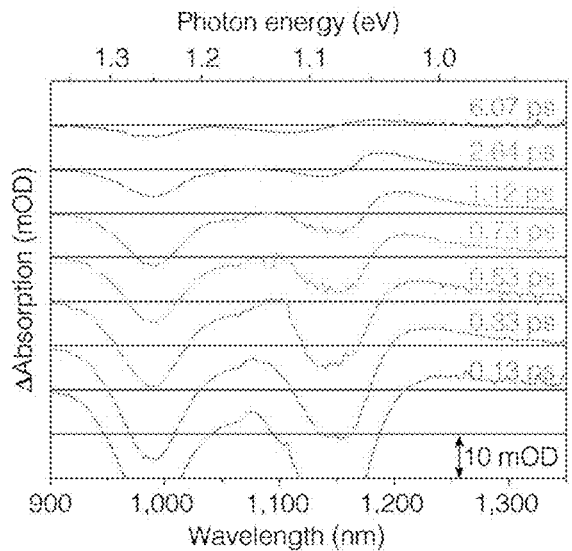
Figure 34A  Figure 34B
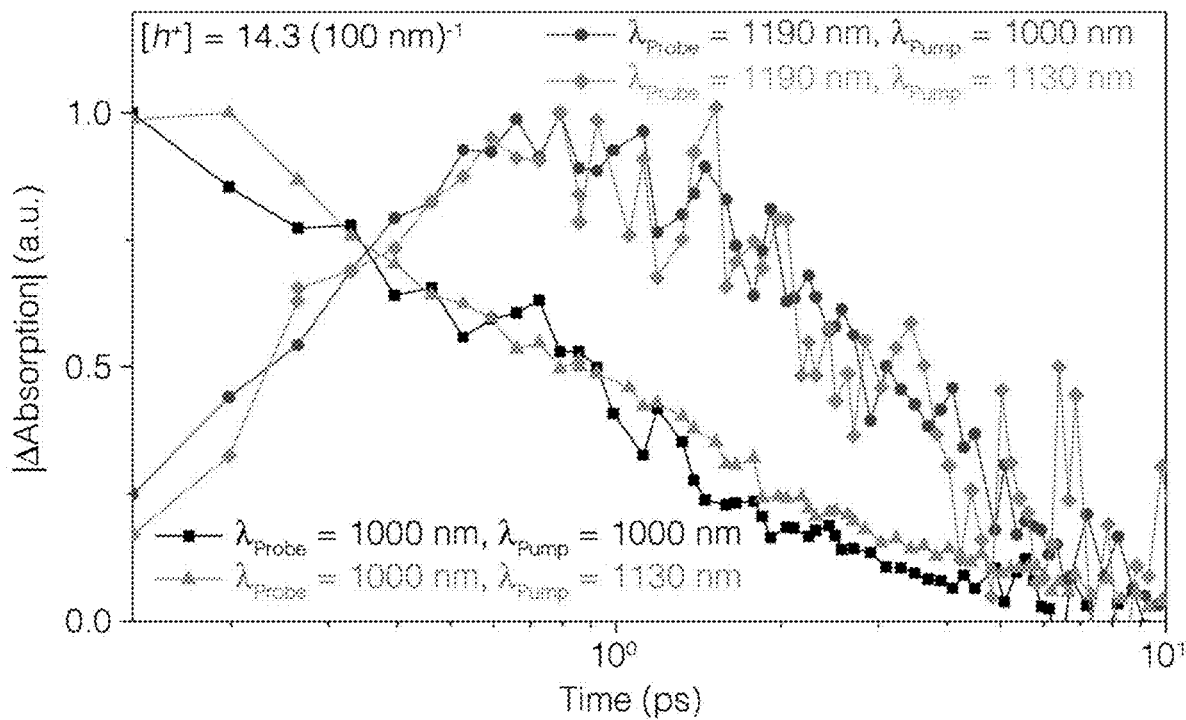
Figure 35

CONTROL OF TRION DENSITY IN CARBON NANOTUBES FOR ELECTRO-OPTICAL AND OPTO-ELECTRIC DEVICES

CROSS REFERENCE TO RELATED APPLICATION(S)

This application claims the benefit of U.S. Provisional Patent Application Ser. No. 62/599,188, which was filed Dec. 15, 2017.

GOVERNMENT SUPPORT

This invention was made with government support under Federal Grant No. DE-SC0001517 awarded by the U.S. Department of Energy. The U.S. Government has certain rights in this invention.

BACKGROUND

Formation of quasiparticles, such as excitons, polarons, and trions in semiconductors are the foundation for modern optoelectronics. Single walled carbon nanotubes (SWNTs), as nearly ideal one-dimensional (1D) systems with unique band structures, display outstanding electronic and optical properties. Because SWNTs are direct band gap materials wherein the band gap progressively varies as a function of nanotube diameter (or chirality), they are particularly attractive for light-emitting, photon-sensing, and photovoltaic applications.

With extraordinary 1D confinement, SWNTs are known to produce strongly bound excitons following optical excitation; nonetheless, a non-negligible portion of optically produced excitons is known to dissociate into free carriers. Quantitative evaluation of such free-carrier generation (FCG) and elucidating how optically triggered FCG quantum yields may be manipulated are critical for exploiting SWNTs in photon sensing, photovoltaic, and many other optoelectronic applications.

Further, unlike the widely investigated exciton and polaron, the trion, a three-body charge-exciton bound state, is less familiar due to its small binding energy in conventional inorganic semiconductors.

The trion offers unique opportunities to simultaneously manipulate charge, spin and excitation in 1D SWNTs at room temperature. Effective exploitation of trion quasiparticles requires fundamental insight into their creation and decay dynamics. Such knowledge, however, remains elusive for SWNT trion states, due to the electronic and morphological heterogeneity of commonly interrogated SWNT samples, and the fact that transient spectroscopic signals uniquely associated with the trion state have not been identified.

BRIEF SUMMARY

Control of trion density in carbon nanotubes for electro-optical and opto-electric devices is provided. Trion-density controlled nanotube devices and the techniques and systems for designing such devices are described.

An optoelectronic system can include a single walled carbon nanotube (SWNT) device. The SWNT can include a carrier-doping density with optical conditions that control trion formation that respond via optical, electrical, or magnetic stimuli. The carrier-doping density can include a hole-polaron or electron-polaron concentration.

Trions transmit spin, charge, and excitation. In some cases, the trion formation is characterized by a trion response to a magnetic field. In some cases, the trion formation is characterized by a trion response to an electrical input. In some cases, the trion formation is characterized by a trion response to an optical input. In some cases, the trion formation is characterized by a trion migration rate to an electrode.

A computer program product such as in the form of one or more computer-readable storage media can be provided having instructions stored thereon, that when executed by a processor, direct the processor to at least generate a model of trion formation and decay dynamics for a single walled carbon nanotube (SWNT) device. The model can include a set of differential equations. The media can further include instructions to quantify free carrier generation in a SWNT of the SWNT device. For example, determining quantum yields of optically driven free carrier formation in single walled carbon nanotube (SWNT) devices can be accomplished by: monitoring an increase of the $Tr^{+/-}_{11} \rightarrow Tr^{+/-}_{nm}$ transition amplitude for a single walled carbon nanotube (SWNT); and determining a trion absorption cross section ($\sigma_{Tr}$) associated with the $Tr^{+/-}_{11} \rightarrow Tr^{+/-}_{nm}$ transition manifold. In some cases, the instructions stored on the media can be integrated with a computer aided design tool.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 9A shows pump-probe spectra of neutral S-PBN(b)-Ph$_5$-[(6,5) SWNTs] following $E_{00} \rightarrow E_{11}$ excitation (hvpump~1.24 eV), pump power=180 nJ/pulse. FIG. 9B shows pump-probe spectra of neutral S-PBN(b)-Ph$_5$-[(6,5) SWNTs] following $E_{00} \rightarrow E_{22}$ excitation (hvpump~2.13 eV), pump power=310 nJ/Pulse. FIG. 9C shows pump-probe spectra of neutral S-PBN(b)-Ph5-[(6, 5) SWNTs] following $E_{00} \rightarrow E_{33}$ excitation (hvpump~3.54 eV), pump power=500 nJ/pulse. General experimental conditions: ambient temperature (~293 K), magic angle polarization, solvent=D2O.

Figure 10A:
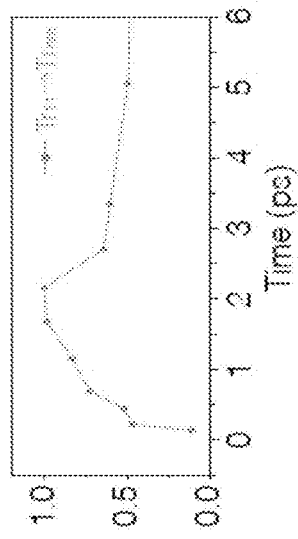
Figure 10B:
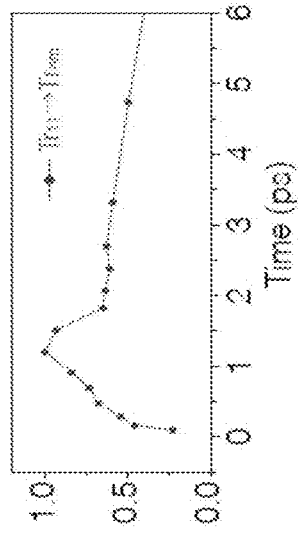
Figure 10C:
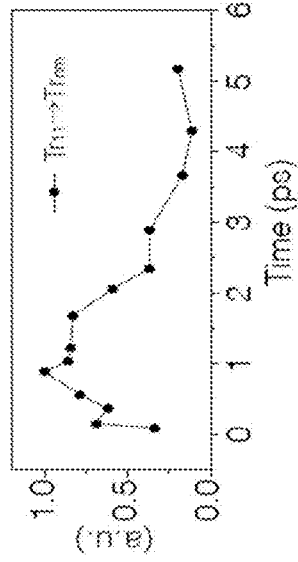
Figure 10D:
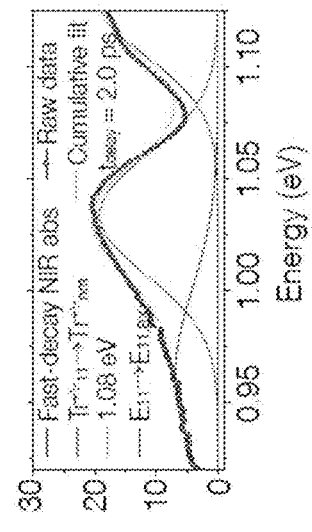
Figure 10E:
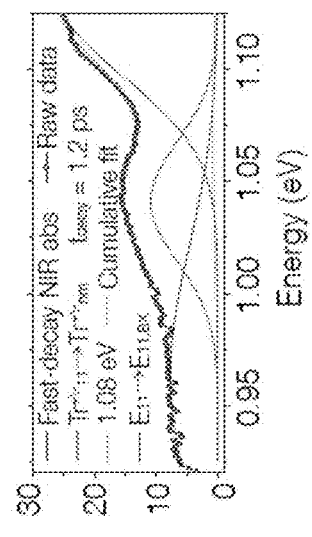
Figure 10F:
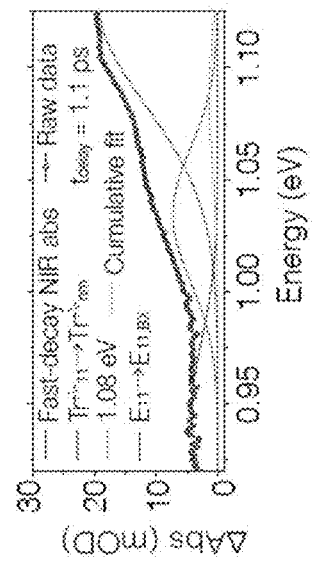

FIGS. 10A-10F show trion formation dynamics and spectral deconvolution of pump-probe spectra in the NIR regime for neutral S-PBN(b)-Ph5-[(6,5) SWNTs]. FIG. 10A shows trion formation dynamics characterized by the changes of oscillator strength corresponding to the $Tr^+_{11} \rightarrow Tr^+_{nm}$ transition (acquired following optical excitation at 1.24 eV; $E_{00} \rightarrow E_{11}$ excitation). FIG. 10B shows trion formation dynamics similar to FIG. 10A except for excitation energy (hvpump=2.13 eV; $E_{00} \rightarrow E_{22}$ excitation). FIG. 10C shows trion formation dynamics similar to FIG. 10A except for excitation energy (hvpump=3.54 eV; $E_{00} \rightarrow E_{33}$ excitation). FIG. 10D shows Gaussian deconvolution of pump-probe spectra at tdelay~1.1 ps, hvpump=1.24 eV. FIG. 10E shows Gaussian deconvolution of pump-probe spectra at tdelay~1.2 ps, hvpump=2.13 eV. FIG. 10F shows Gaussian deconvolution of pump-probe spectra at tdelay~2.0 ps, hvpump=3.54 eV.

Figure 11:
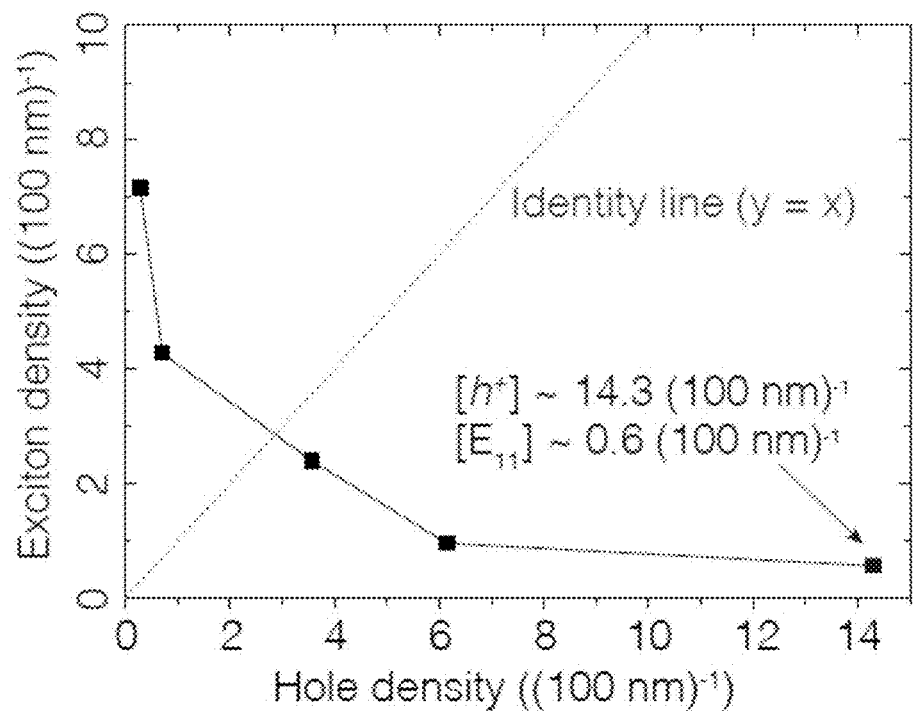

FIG. 11 shows a plot of exciton density vs. hole doping density for S-PBN(b)-Ph$_5$-[(6,5) SWNTs].

Figure 12:
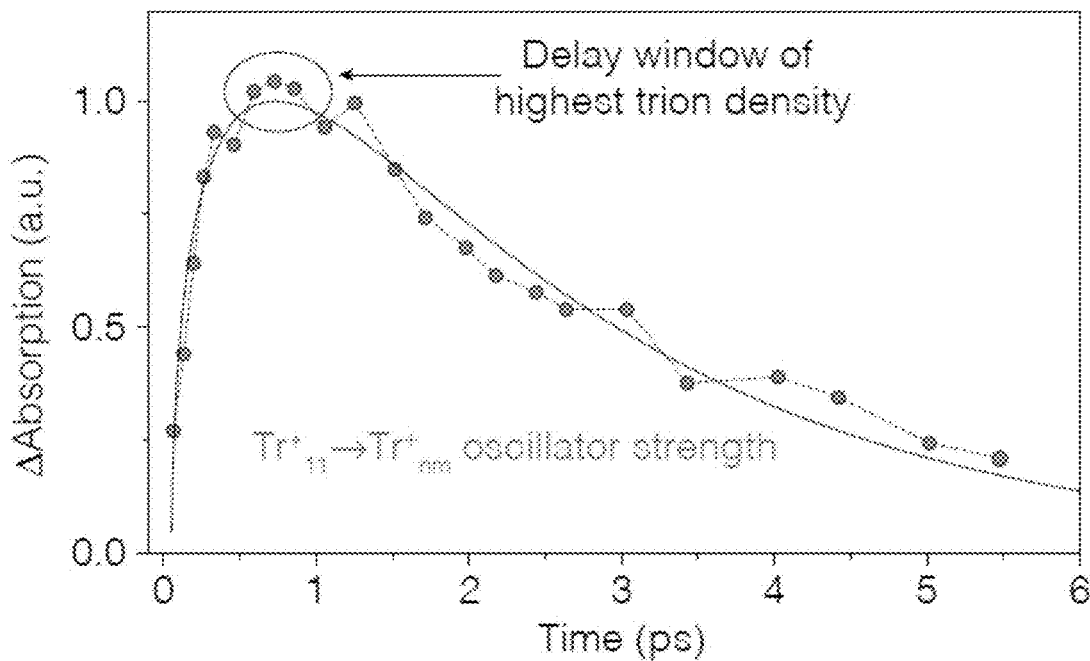

FIG. 12 shows a kinetic trace representing trion formation dynamics in hole-doped S-PBN(b)-Ph5-[(6,5) SWNTs].

Figure 13:
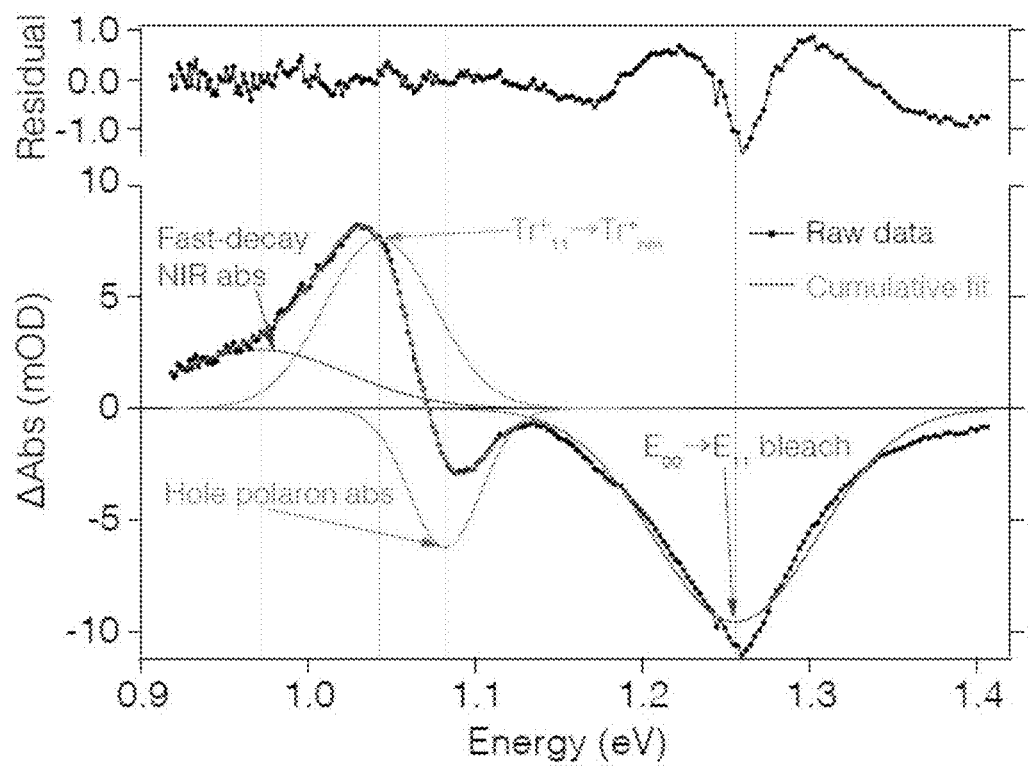

FIG. 13 shows a deconvoluted pump-probe transient spectrum at tdelay~0.9 ps for hole-doped S-PBN(b)-Ph5-[(6,5) SWNTs]. The absorbance contribution at 1.04 eV from the $Tr^+_{11} \rightarrow Tr^+_{nm}$ transition (orange) is determined as ~7.66 mOD.

Figure 14:
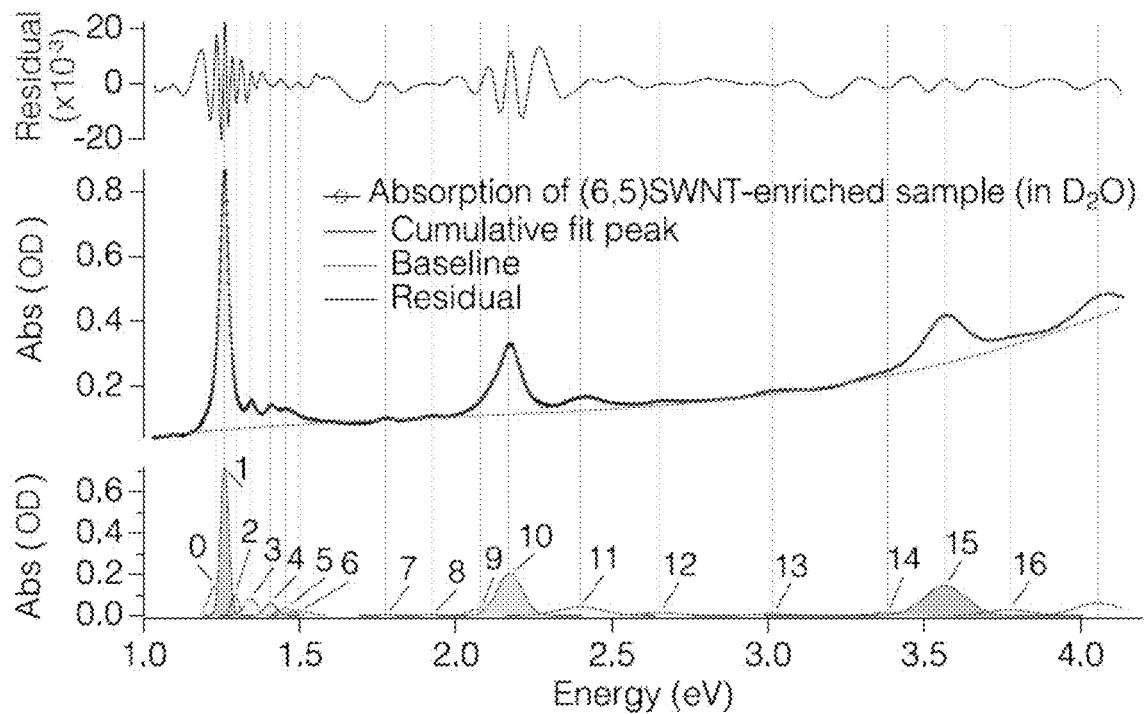

FIG. 14 shows a deconvolution of a linear absorption spectrum of SWNTs.

Figure 15A:
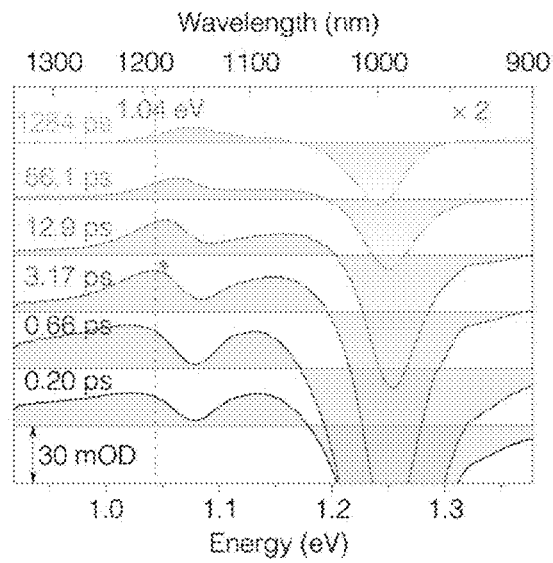
Figure 15B:
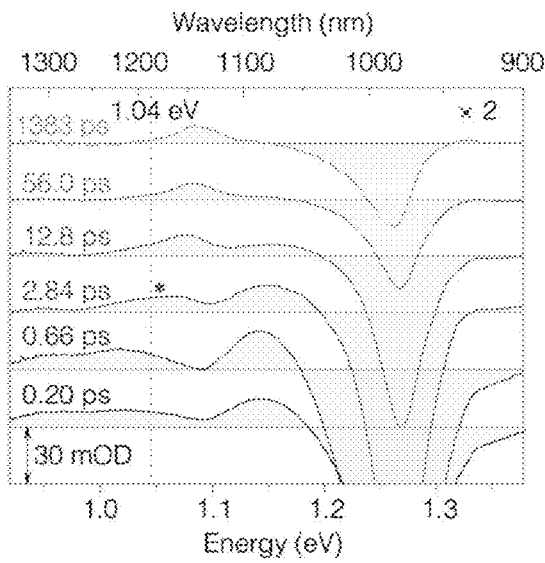

FIGS. 15A and 15B show trion signal in transient (pump-probe) spectra of neutral polymer-SWNTs and SC-SWNTs, respectively.

Figure 3:
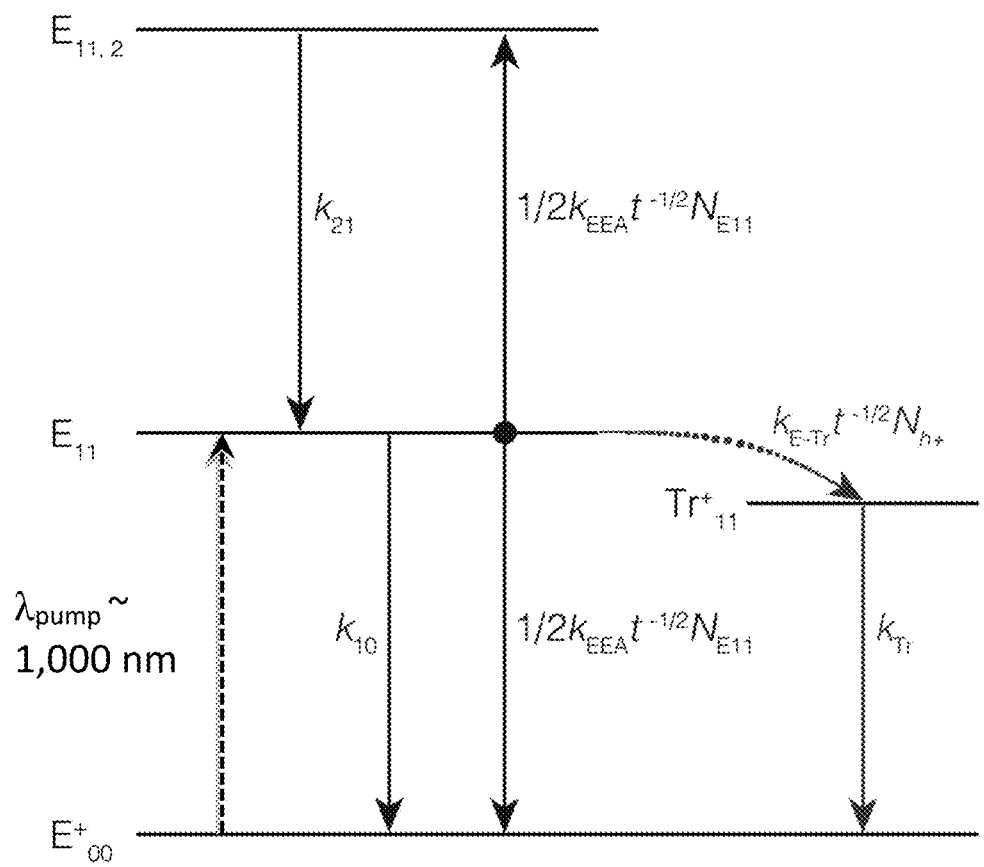
FIG. 3 shows an energy band diagram depicting a 1D diffusion kinetic model of trion formation and decay dynamics.
Figure 16A:
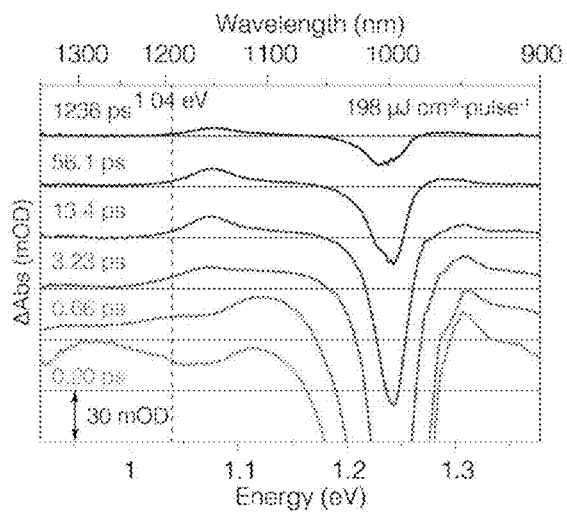
Figure 16B:
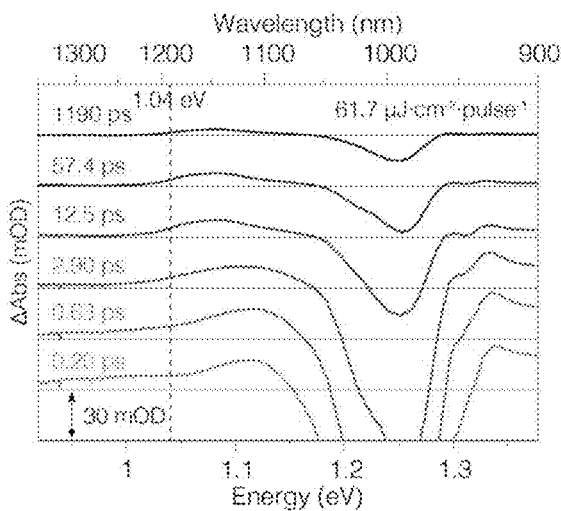
Figure 16C:
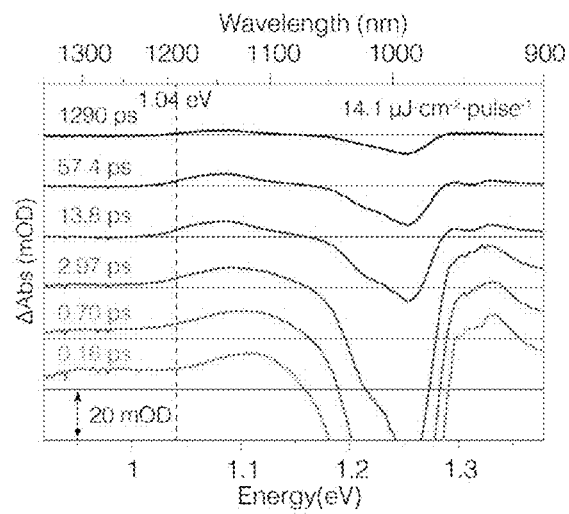
Figure 16D:
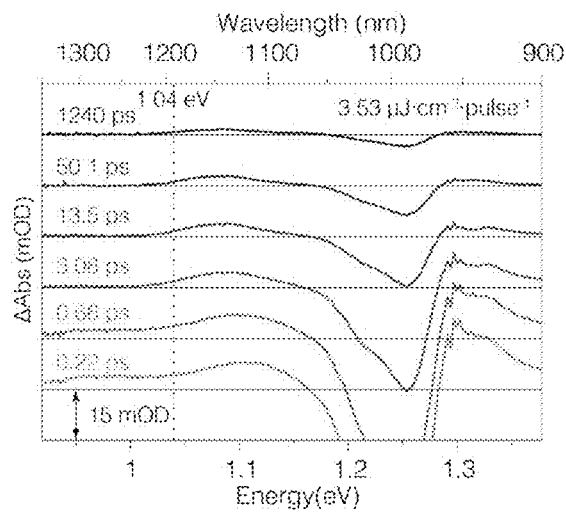
Figure 16E:
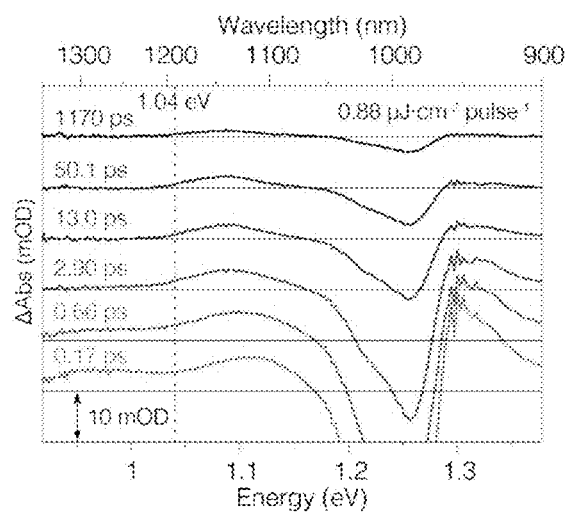
Figure 16F:
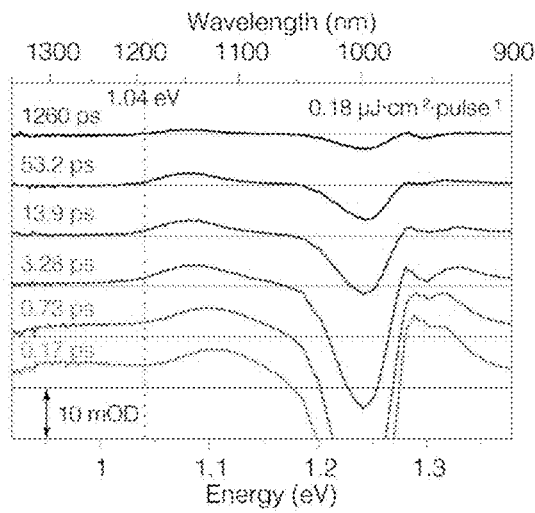

FIGS. 16A-16F show fluence-dependent transient absorption spectra with $E_{00} \rightarrow E_{11}$ optical excitation from pump-probe spectra recorded for neutral S-PBN(b)-Ph5-[(6,5) SWNTs] with a broad range of pump fluences: FIG. 16A: 198 $\mu J \cdot cm^{-2} \cdot pulse^{-1}$; FIG. 16B: 61.7 $\mu J \cdot cm^{-2} \cdot pulse^{-1}$; FIG. 16C: 14.1 $\mu J \cdot cm^{-2} \cdot pulse^{-1}$; FIG. 16D 3.53 $\mu J \cdot cm^{-2} \cdot pulse^{-1}$; FIG. 16E: 0.88 $\mu J \cdot cm^{-2} \cdot pulse^{-1}$; FIG. 16F: 0.18 $\mu J \cdot cm^{-2} \cdot pulse^{-1}$.

Figure 17A:
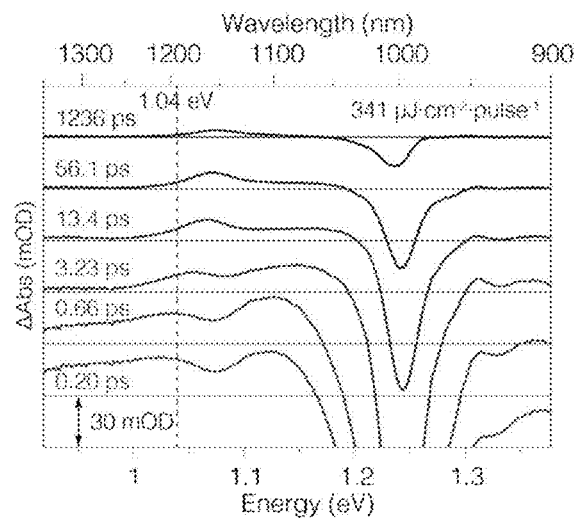
Figure 17B:
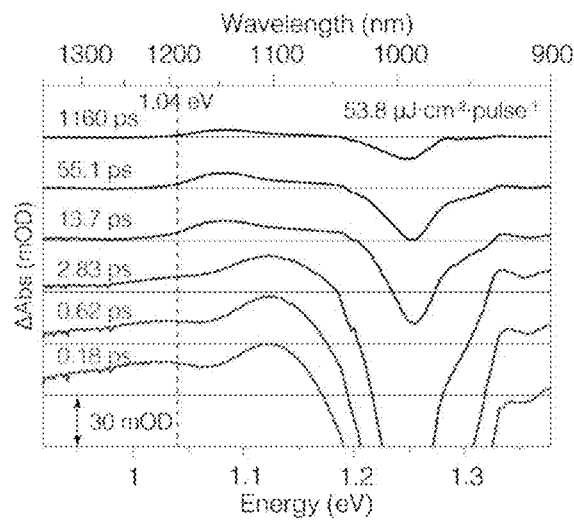
Figure 17C:
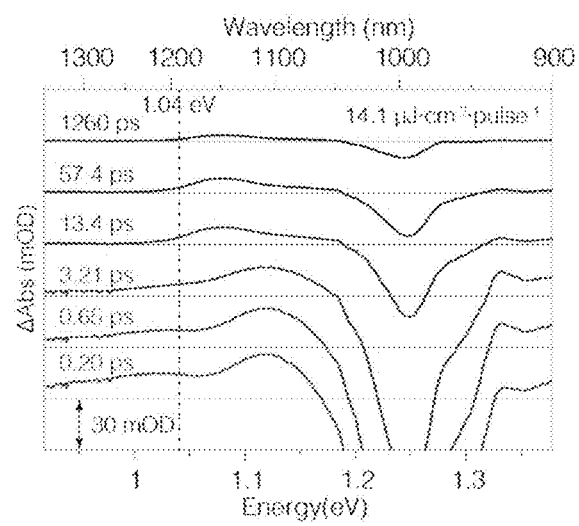
Figure 17D:
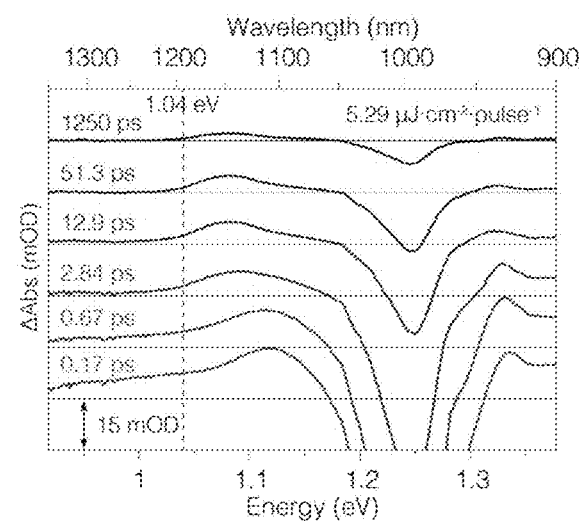
Figure 17E:
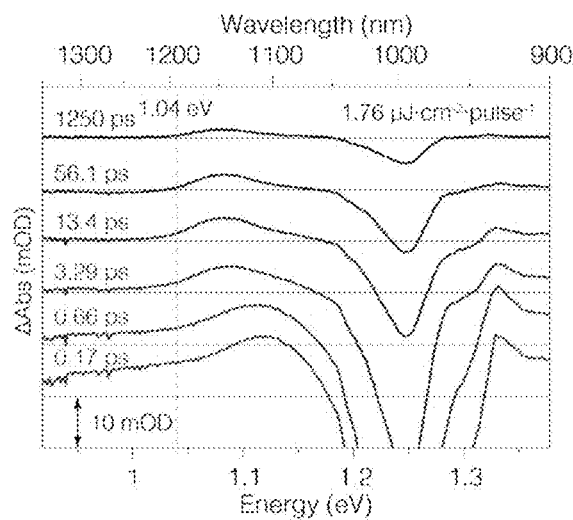
Figure 17F:
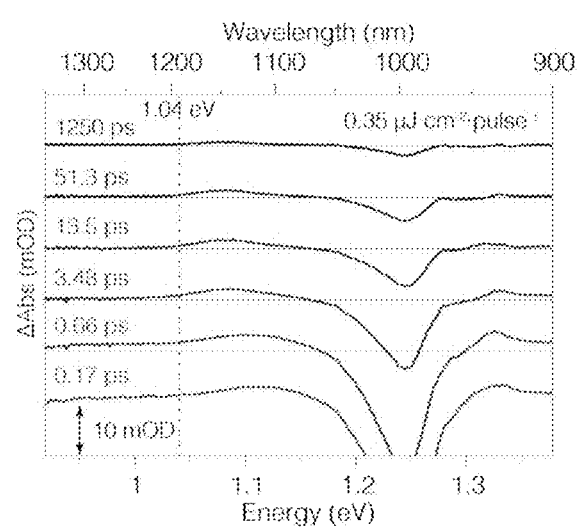

FIGS. 17A-17F show fluence-dependent transient absorption spectra with $E_{00} \rightarrow E_{22}$ optical excitation from pump-probe spectra recorded for neutral S-PBN(b)-Ph5-[(6,5) SWNTs] with a broad range of pump fluences: FIG. 17A: 341 $\mu J \cdot cm^{-2} \cdot pulse^{-1}$; FIG. 17B: 53.8 $\mu J \cdot cm^{-2} \cdot pulse^{-1}$; FIG. 17C: 14.1 $\mu J \cdot cm^{-2} \cdot pulse^{-1}$; FIG. 17D: 5.29 $\mu J \cdot cm^{-2} \cdot pulse^{-1}$; FIG. 17E: 1.76 $\mu J \cdot cm^{-2} \cdot pulse^{-1}$; FIG. 17F: 0.35 $\mu J \cdot cm^{-2} \cdot pulse^{-1}$.

Figure 18A:
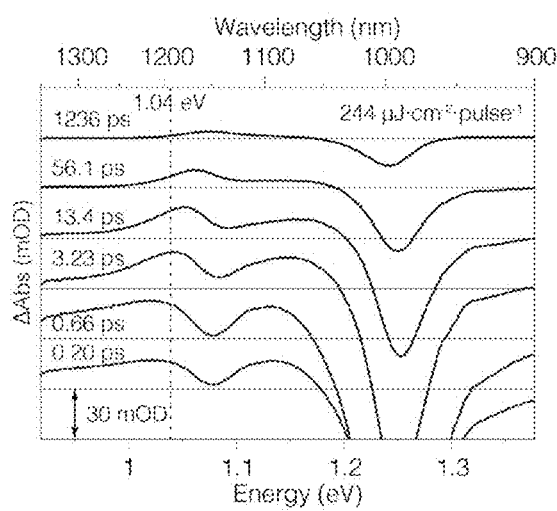
Figure 18B:
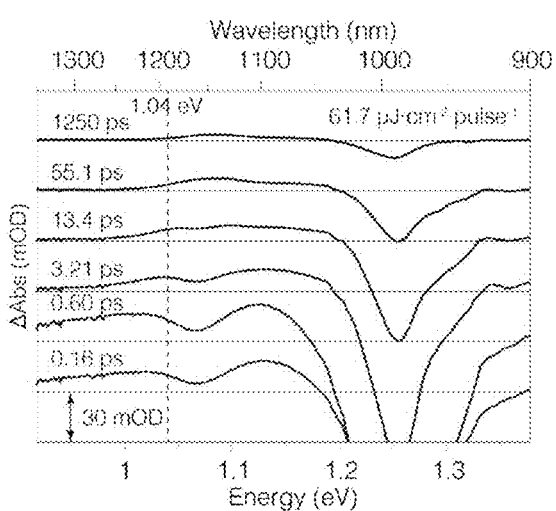
Figure 18C:
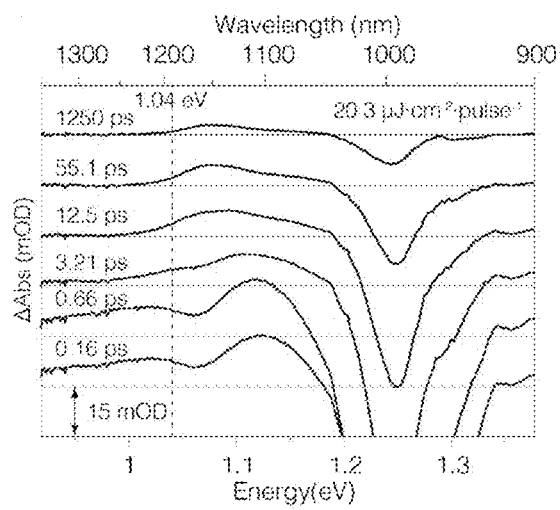
Figure 18D:
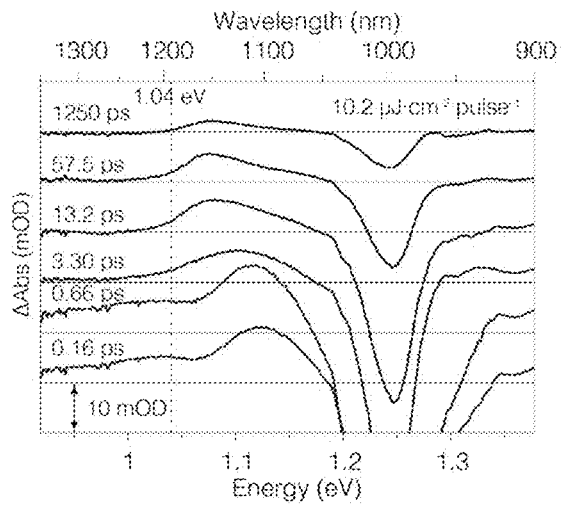
Figure 18E:
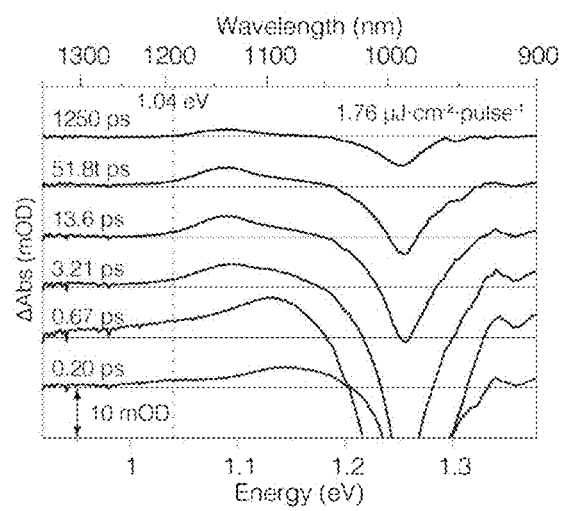

FIGS. 18A-18E show fluence-dependent transient absorption spectra with $E_{00} \rightarrow E_{33}$ optical excitation from pump-probe spectra recorded for neutral S-PBN(b)-Ph5-[(6,5) SWNTs] with a broad range of pump fluences: FIG. 18A 244 $\mu J \cdot cm^{-2} \cdot pulse^{-1}$; FIG. 18B: 61.7 $\mu J \cdot cm^{-2} \cdot pulse^{-1}$; FIG. 18C: 20.3 $\mu J \cdot cm^{-2} \cdot pulse^{-1}$; FIG. 18D: 10.2 $\mu J \cdot cm^{-2} \cdot pulse^{-1}$; FIG. 18E: 1.76 $\mu J \cdot cm^{-2} \cdot pulse^{-1}$.

Figure 19A:
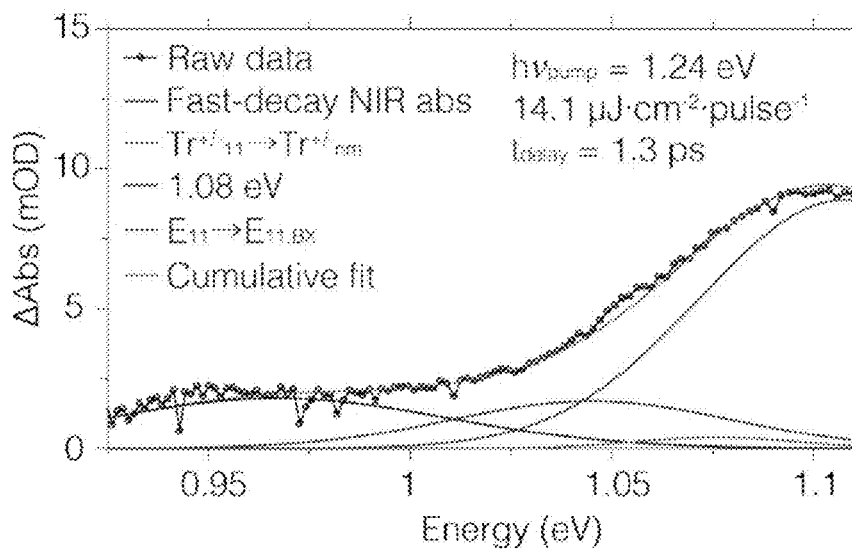
Figure 19B:
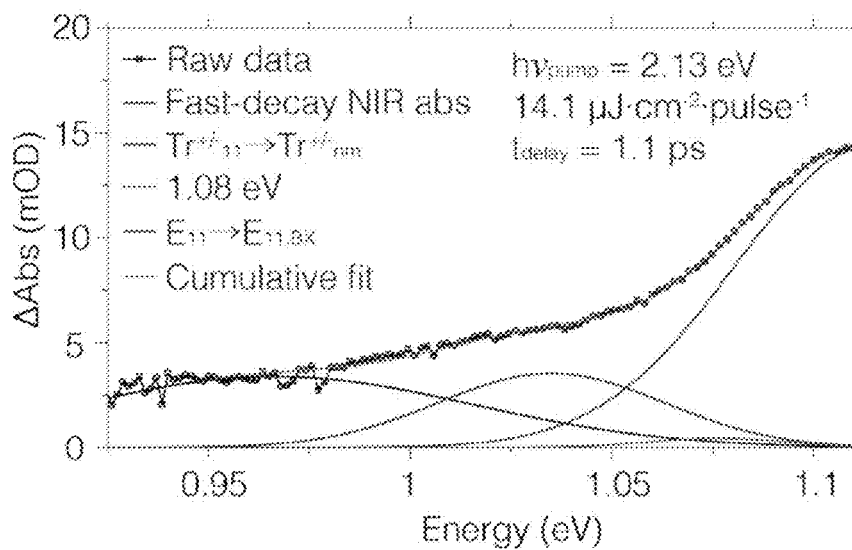
Figure 19C:
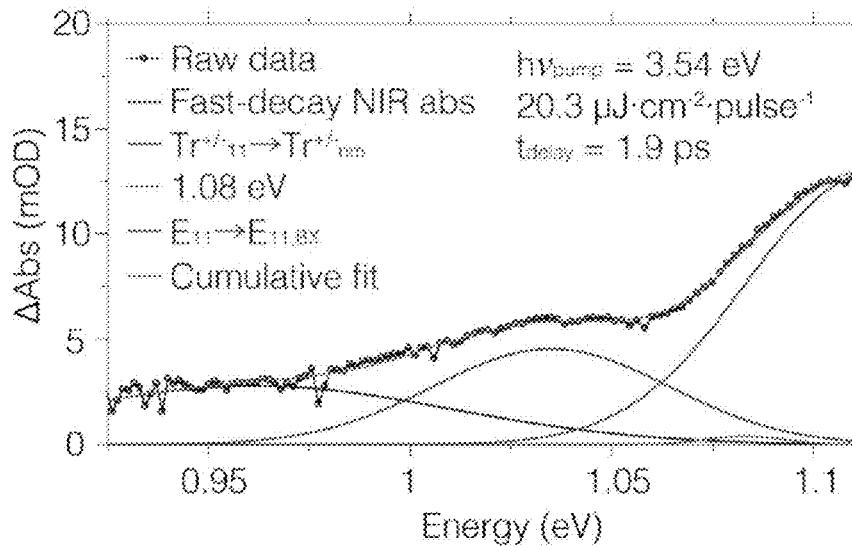

FIGS. 19A-19C show spectral deconvolution of pump-probe spectra in the NIR regime for neutral SPBN(b)-Ph5-[(6,5) SWNTs]. FIG. 19A shows Gaussian deconvolution of pump-probe spectra at tdelay~1.3 ps, hvpump=1.24 eV. FIG. 19B shows Gaussian deconvolution of pump-probe spectra at tdelay~1.1 ps, hvpump=2.13 eV. FIG. 19C shows Gaussian deconvolution of pump-probe spectra at tdelay~1.9 ps, hvpump=3.54 eV.

Figure 20:
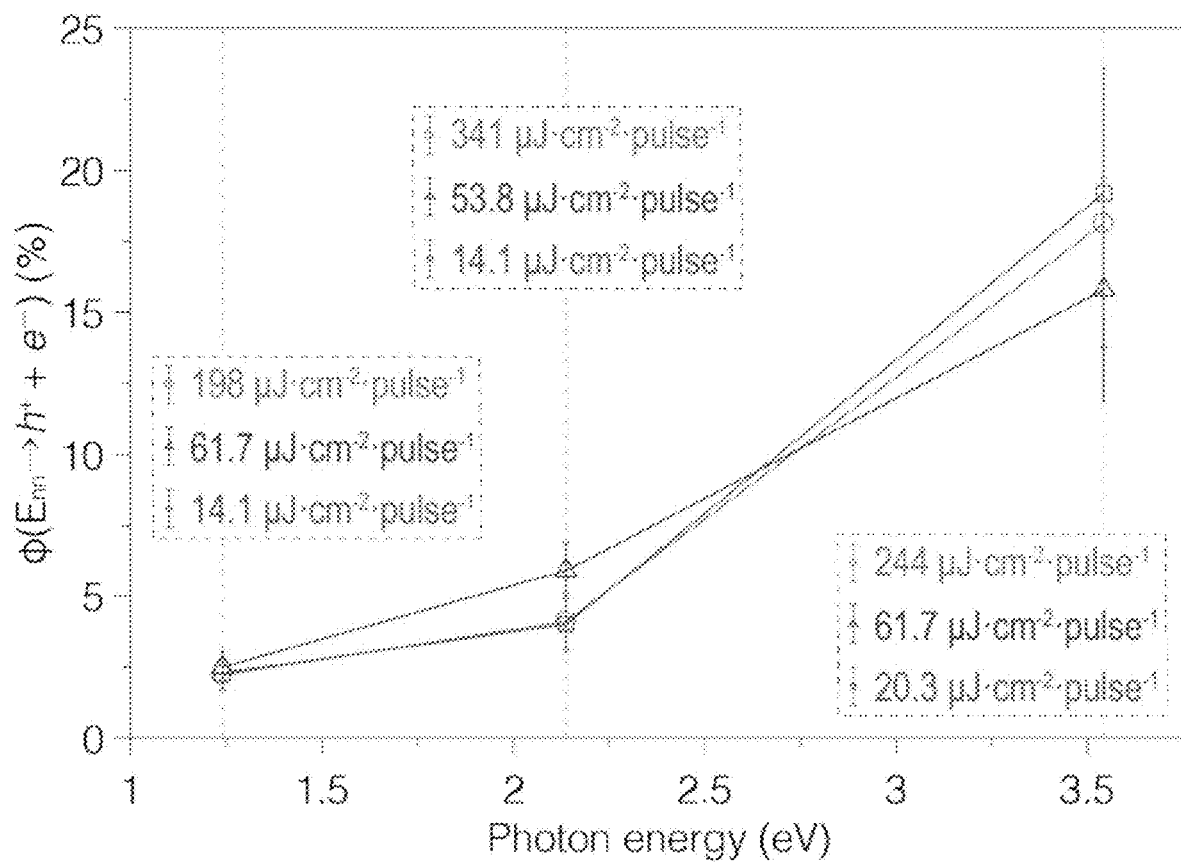

FIG. 20 shows a plot of excitation-energy- and fluence-dependent FCG quantum yields.

Figure 21A:
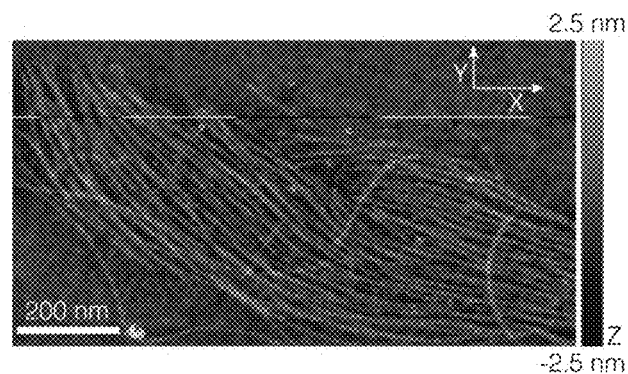
Figure 21B:
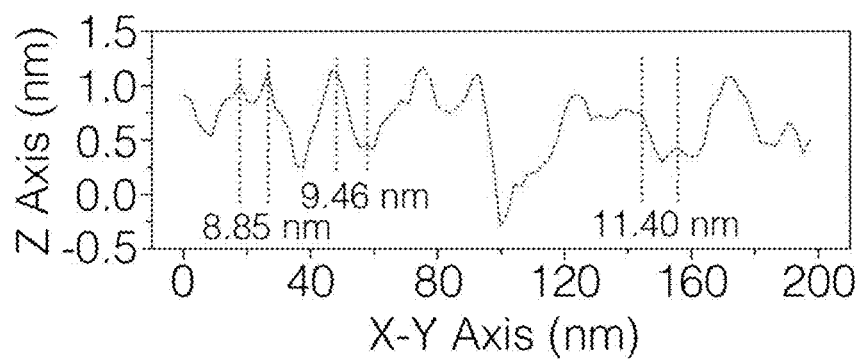
Figure 21C:
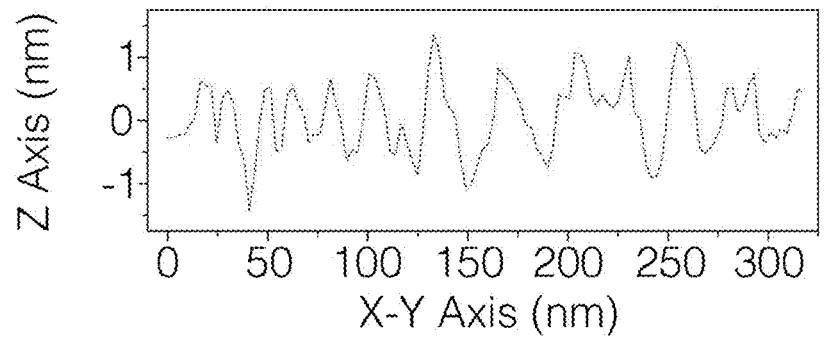

FIGS. 21A-21C show AFM characterization of S-PBN (b)-Ph5-[(6,5) SWNT] samples. FIG. 21A is a topographic intermittent contact AFM image of S-PBN(b)-Ph5-[(6,5) SWNT] from an aqueous suspension on a Si surface. FIG. 21B shows a height profile along the x direction of FIG. 21A; and FIG. 21C shows a height profile along the z direction (out of page) of FIG. 21A.

Figure 22A:
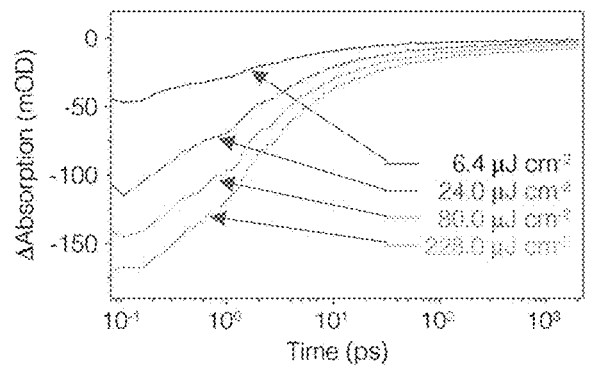
Figure 22B:
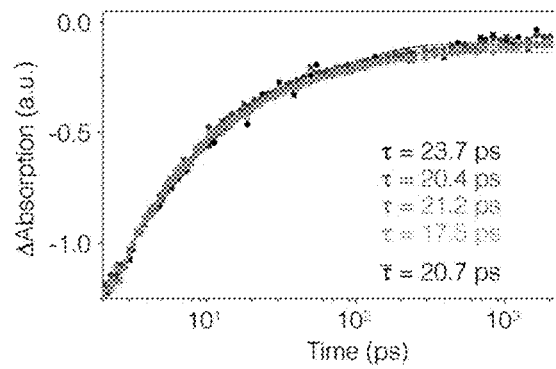

FIGS. 22A and 22B show $E_{11}$ exciton dynamics in neutral S-PBN(b)-Ph5-[(6,5) SWNT]. FIG. 22A shows excitation fluence-dependence of $E_{00} \rightarrow E_{11}$ bleaching signal intensity at 1010 nm. FIG. 22B shows $E_{00} \rightarrow E_{11}$ bleach kinetics (same data as that displayed in a) normalized at tdelay=3 ps, and the exponential function fitting of the kinetic traces (fitting range: 3-2500 ps).

Figure 23:
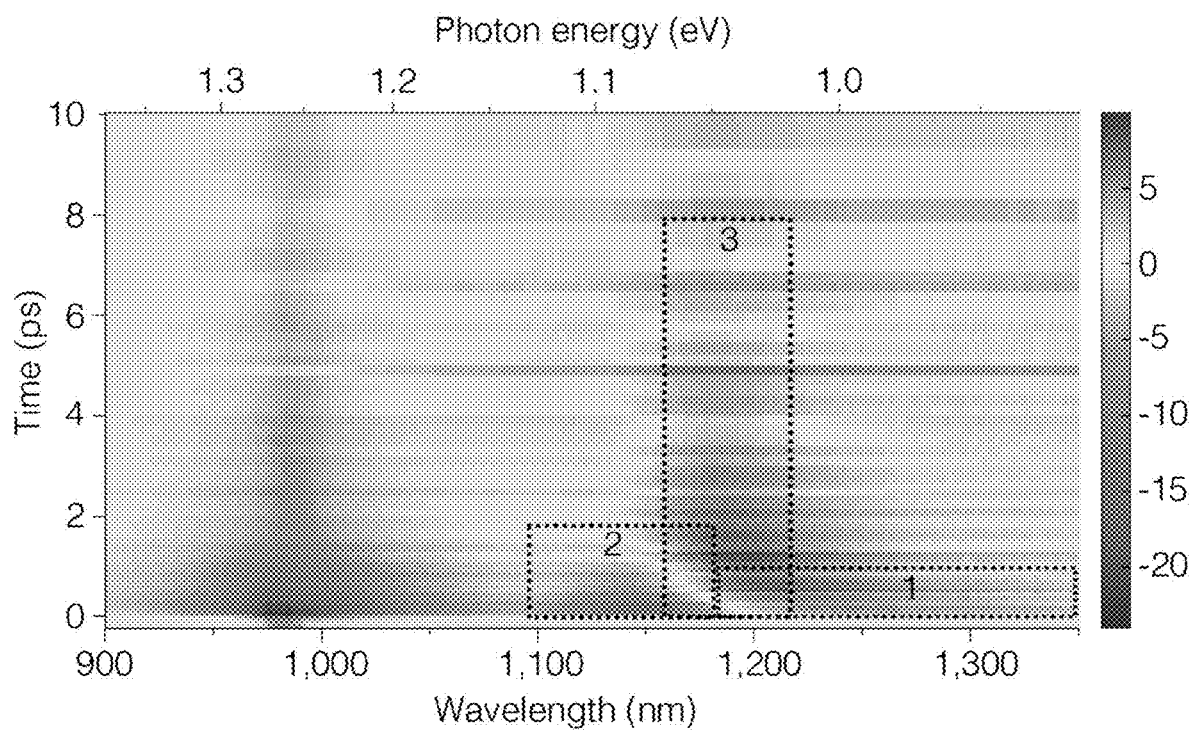

FIG. 23 shows two-dimensional pump-probe spectral data for hole-doped S-PBN(b)-Ph5-[(6,5) SWNT].

Figure 24:
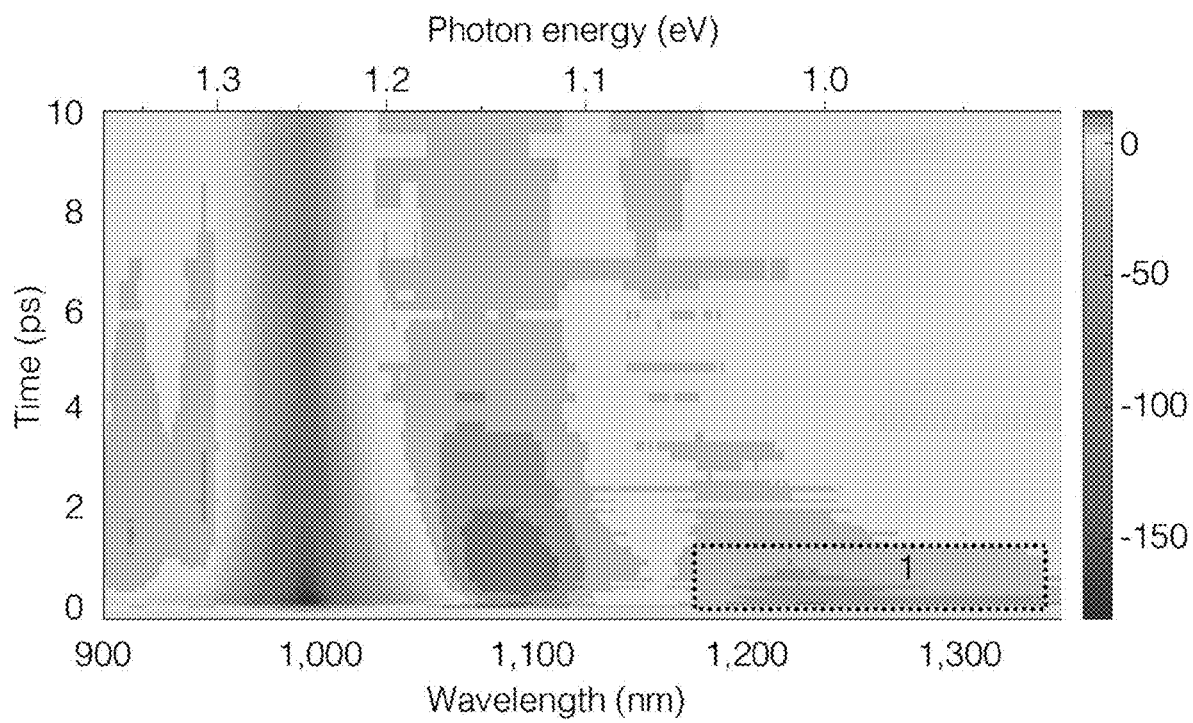

FIG. 24 shows two-dimensional pump-probe spectral data for neutral S-PBN(b)-Ph5-[(6,5) SWNTs].

Figure 25:
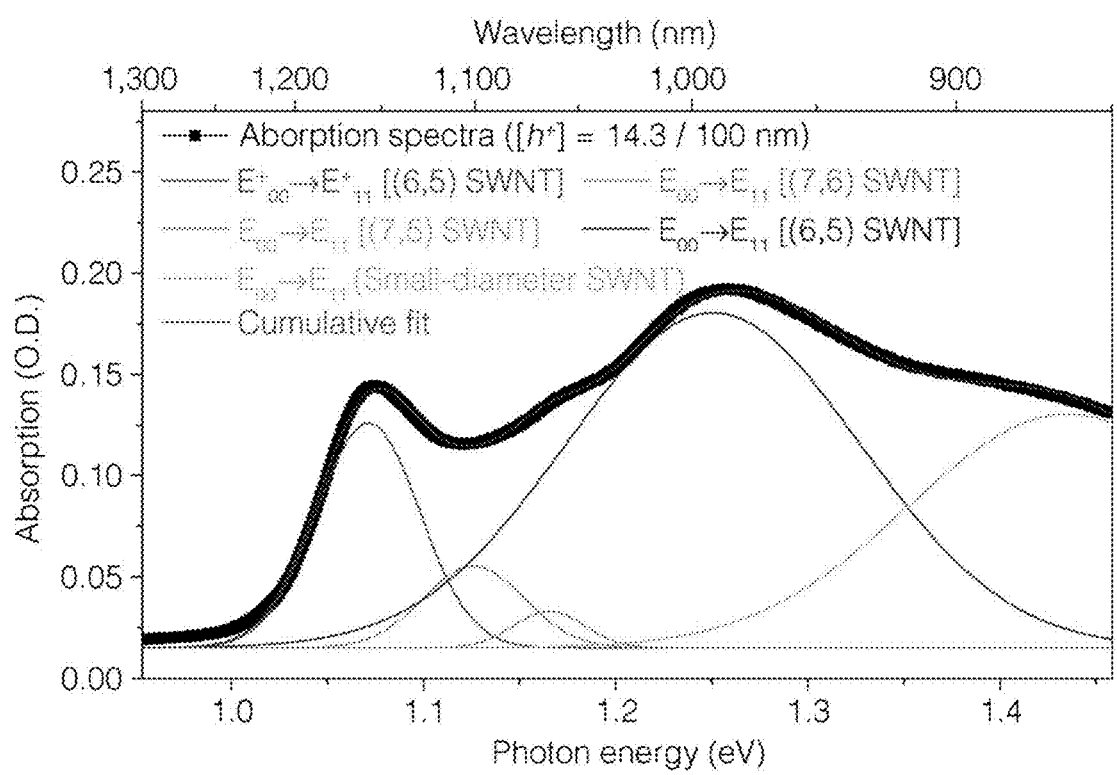

FIG. 25 shows a linear absorption spectrum for hole-doped S-PBN(b)-Ph5-[(6,5) SWNTs].

Figure 26A:
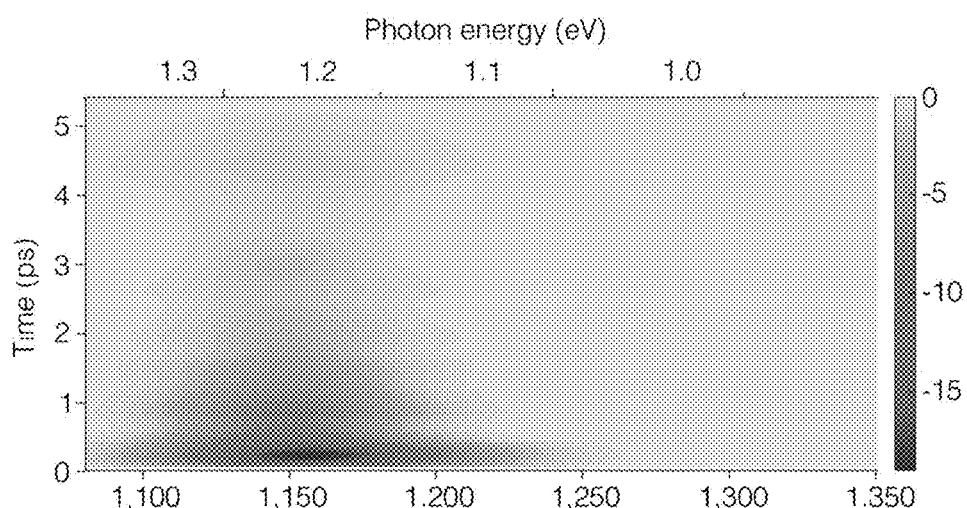
Figure 26B:
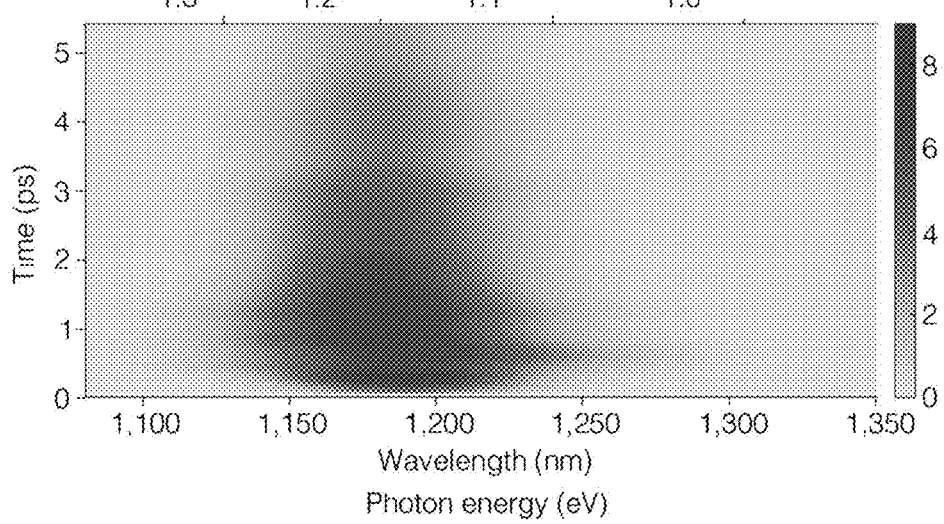
Figure 26C:
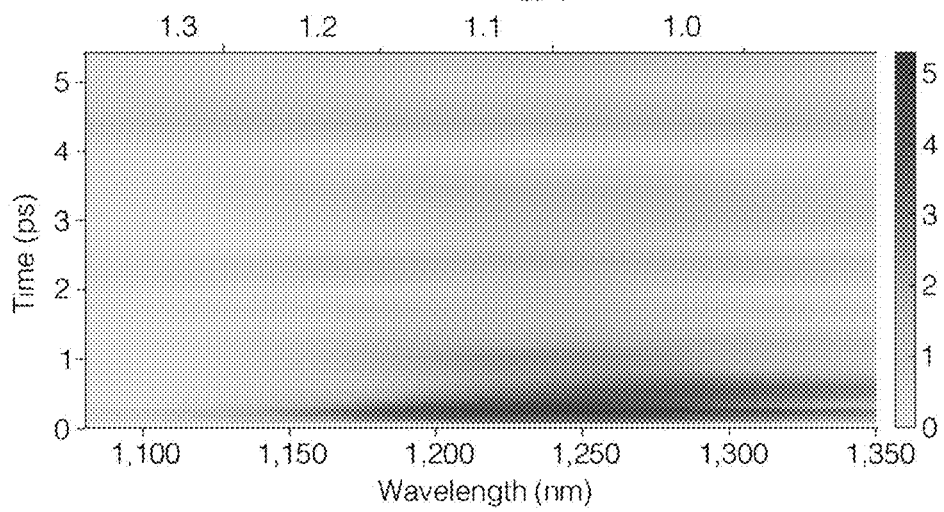

FIGS. 26A-26C show two-dimensional mapping of separated transient signals in the NIR domain. FIG. 26A shows extracted transient signals for $E^+_{00} \rightarrow E^+_{11}$ bleach. FIG. 26B shows extracted transient signals for $Tr^+_{11} \rightarrow Tr^+_{nm}$ absorption. FIG. 26C shows extracted transient signals for the fast-decay NIR absorption as highlighted in FIG. 25.

Figure 27A:
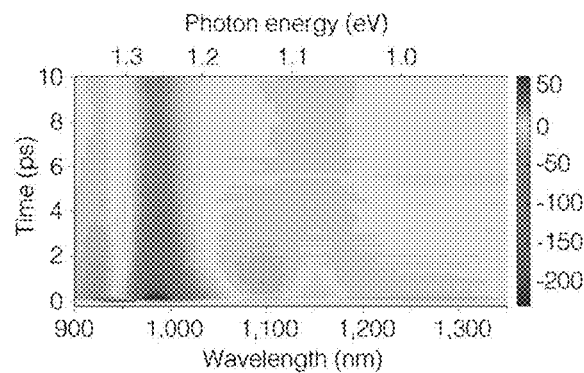
Figure 27B:
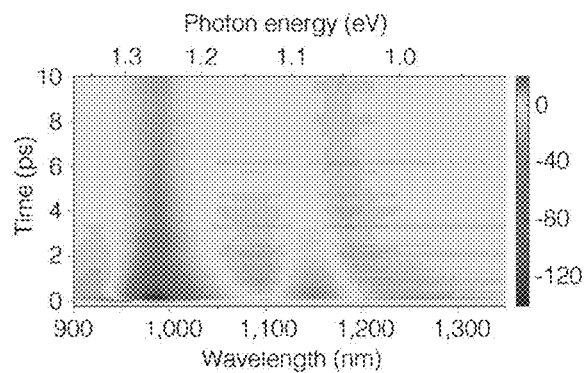
Figure 27C:
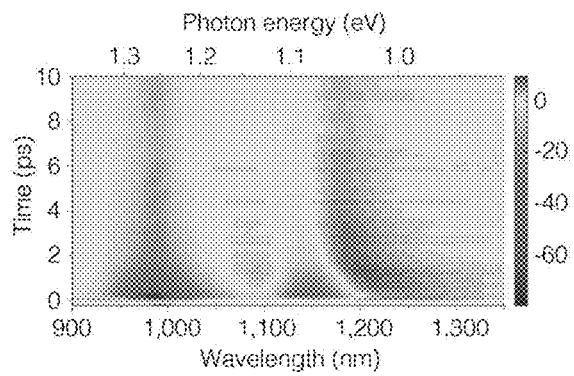
Figure 27D:
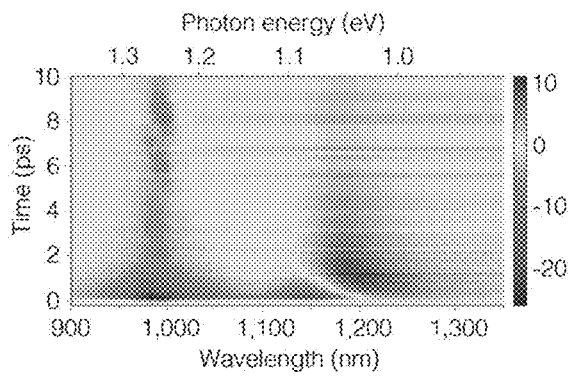

FIGS. 27A-27D show two-dimensional pump-probe spectra for S-PBN(b)-Ph5-[(6,5) SWNT] having varying [h+]. FIG. 27A shows two-dimensional pump-probe spectra of hole-doped SWNTs with [h+]=0.3 $(100 \text{ nm})^{-1}$. FIG. 27B shows two-dimensional pump-probe spectra of hole-doped SWNTs with [h+]=0.7 $(100 \text{ nm})^{-1}$. FIG. 27C shows two-dimensional pump-probe spectra of hole-doped SWNTs with [h+]=3.5 $(100 \text{ nm})^{-1}$. FIG. 27D shows two-dimensional pump-probe spectra of hole-doped SWNTs with [h+]= 6.1 $(100 \text{ nm})^{-1}$.

Figure 28A:
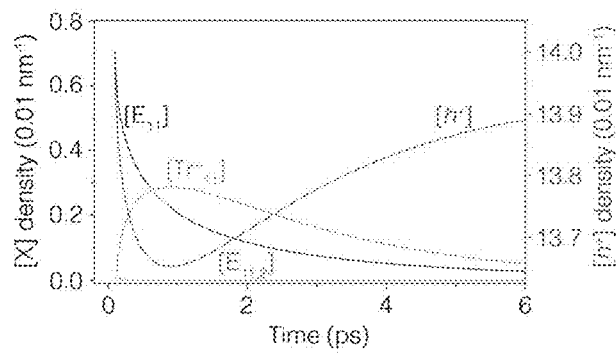
Figure 28B:
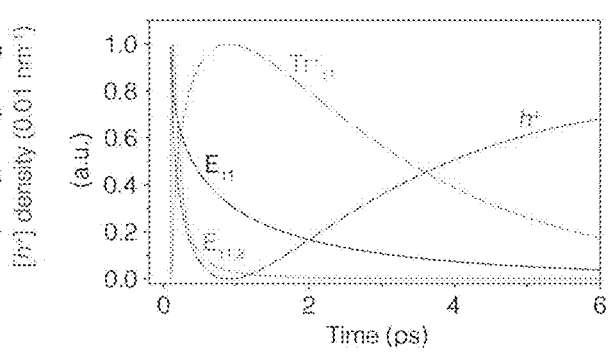

FIGS. 28A and 28B show numerical solutions for $[E_{11}]$, $[E_{11,2}]$, $[Tr^+_{11}]$, and [h+]. FIG. 28A shows numerical solutions for $[E_{11}]$, $[E_{11,2}]$, $[Tr^+_{11}]$, and [h+] obtained by fitting hole-doped S-PBN(b)-Ph5-[(6,5) SWNT] ([h+]~14.0 $(100 \text{ nm})^{-1}$) using equations (1)-(4). Initial values are provided as following: $[E_{11}]$=0.7 $(100 \text{ nm})^{-1}$, $[E_{11,2}]$=0.0 $(100 \text{ nm})^{-1}$, $[Tr^+_{11}]$=0.0 $(100 \text{ nm})^{-1}$, [h+]=14.0 $(100 \text{ nm})^{-1}$. FIG. 28B shows the same data plot as FIG. 28A but with population densities of the corresponding species being normalized.

Figure 29:
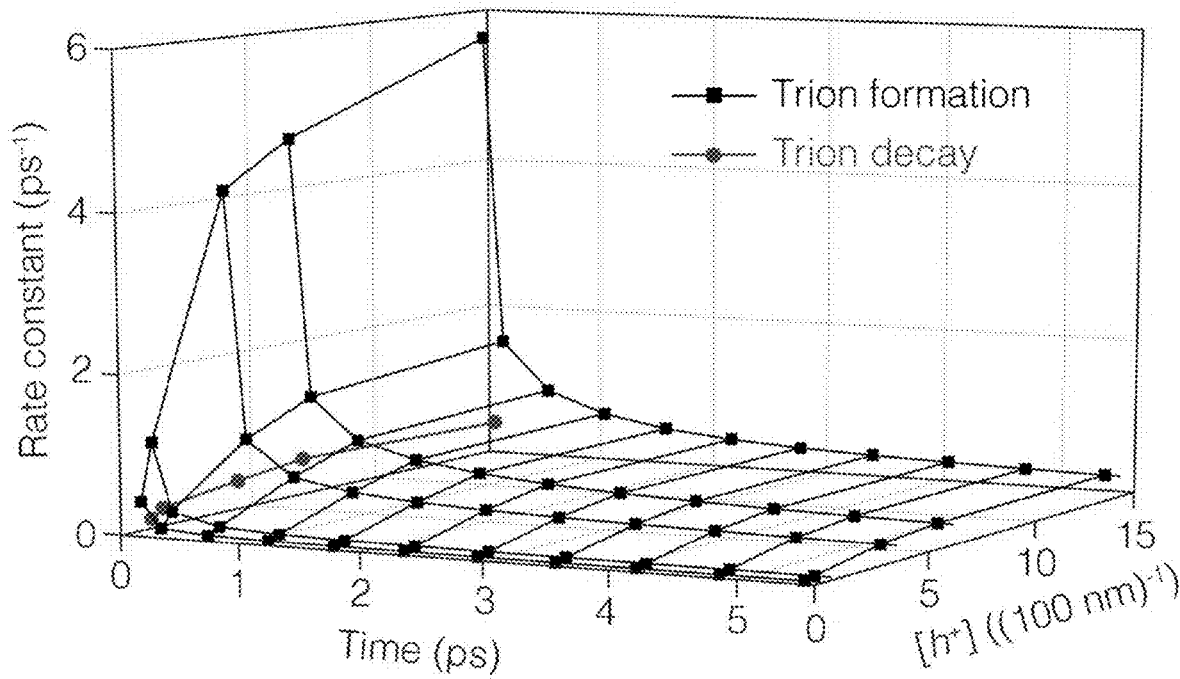

FIG. 29 shows hole trion formation and decay rate constants as a function of both [h+] and t.

Figure 30A:
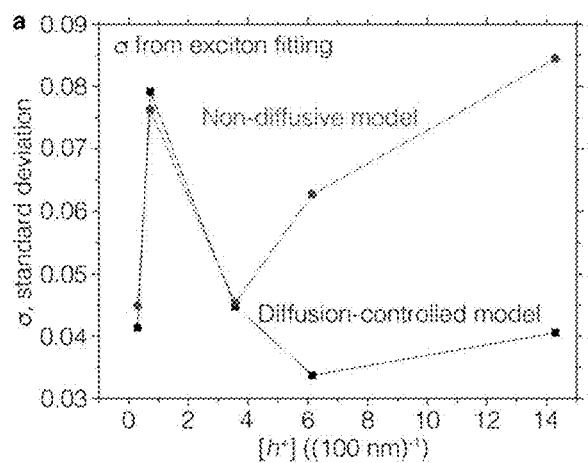
Figure 30B:
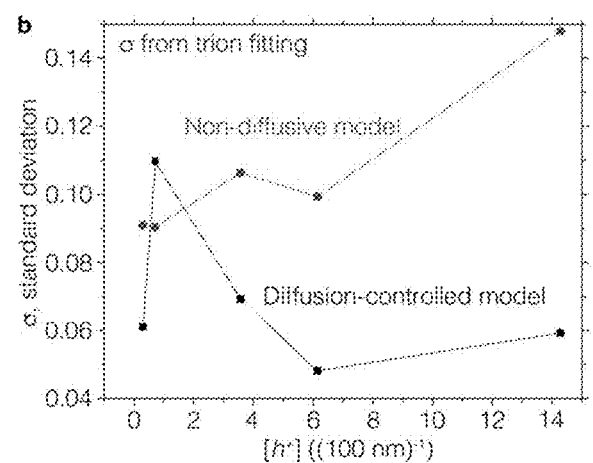

FIGS. 30A and 30B show plots of standard deviations of diffusion-controlled vs non-diffusive models as a function of hole polaron density. FIG. 30A shows standard deviations of exciton dynamical data fitting based on a diffusion-controlled trion formation model and a non-diffusive trion formation model. FIG. 30B shows standard deviations from trion dynamical data fitting based on a diffusion-controlled trion formation model and a non-diffusive trion formation model.

FIGS. 31A-31D show numerical fitting of the diffusion-controlled vs non-diffusive models in the low hole density regime. FIGS. 31A and 31B show diffusion-controlled vs non-diffusive model fitting of exciton and trion dynamical data at [h+]~0.3 $(100 \text{ nm})^{-1}$. FIGS. 31C and 31D show diffusion-controlled vs non-diffusive model fitting of exciton and trion dynamical data at [h+]~0.7 $(100 \text{ nm})^{-1}$.

Figure 32A:
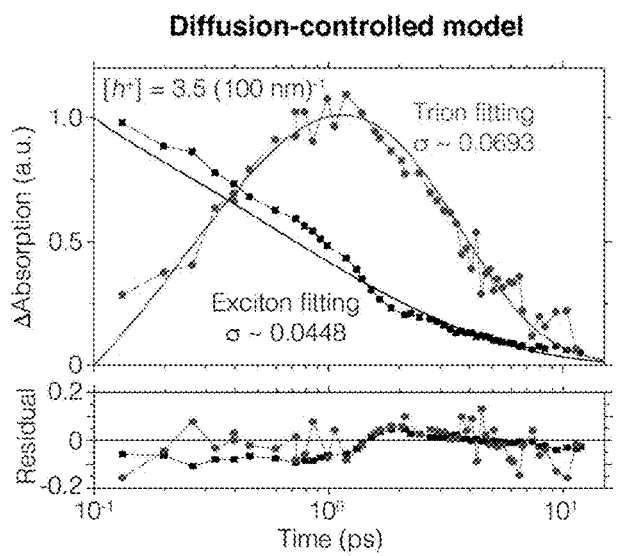
Figure 32B:
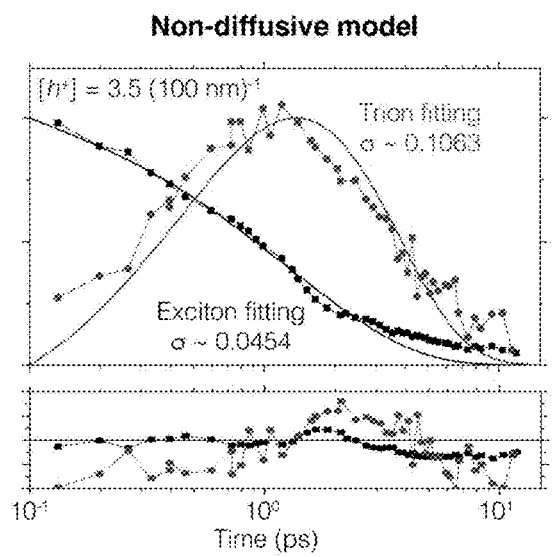
Figure 32C:
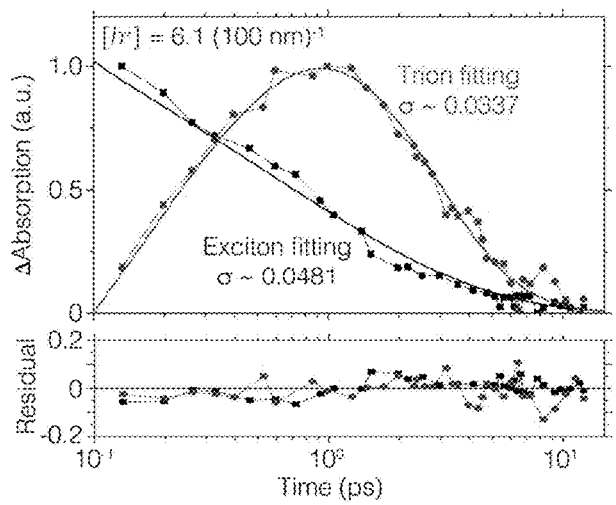
Figure 32D:
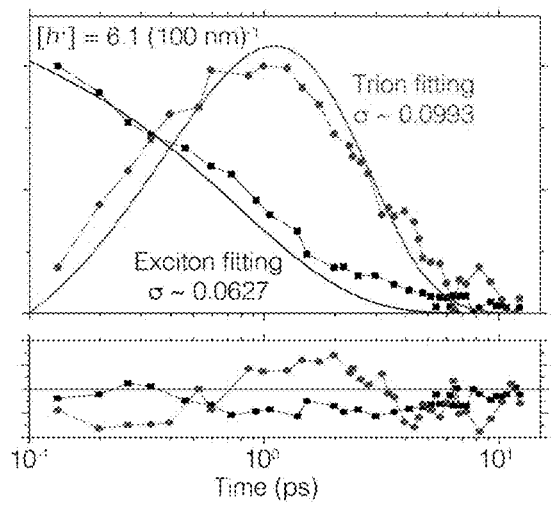
Figure 32E:
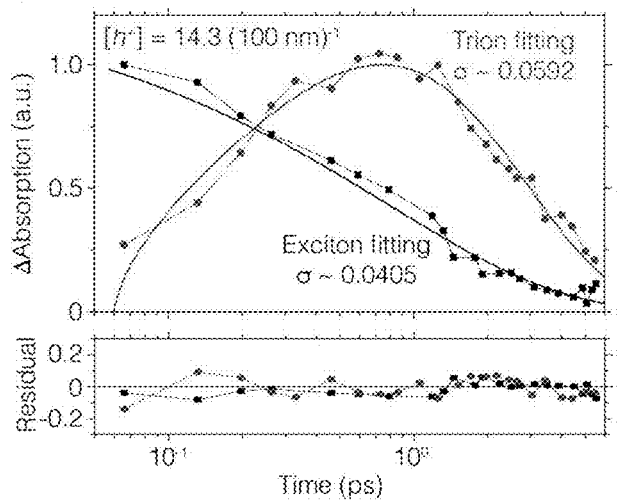
Figure 32F:
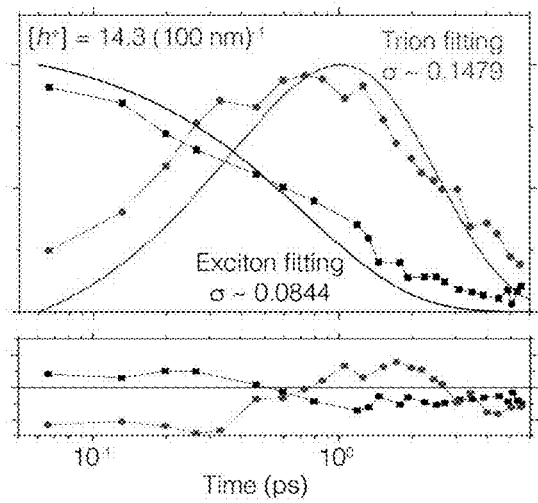

FIGS. 32A-32F show numerical fitting of diffusion-controlled vs non-diffusive models in the medium-to-high hole density regime. FIGS. 32A and 32B show diffusion-controlled vs non-diffusive model fitting of exciton and trion dynamical data at [h+]~3.5 (100 nm)$^{-1}$. FIGS. 32C and 32D show diffusion-controlled model vs non-diffusive model fitting of exciton and trion dynamical data at [h+]~6.1 (100 nm)$^{-1}$. FIGS. 32E and 32F show diffusion-controlled model vs non-diffusive model fitting of exciton and trion dynamical data at [h+]~14.3 (100 nm)$^{-1}$.

Figure 33A:
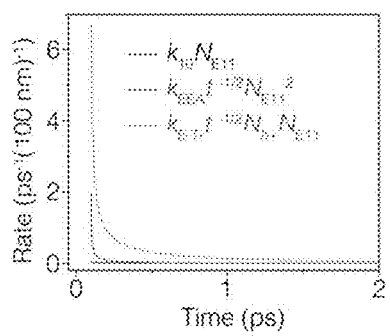
Figure 33B:
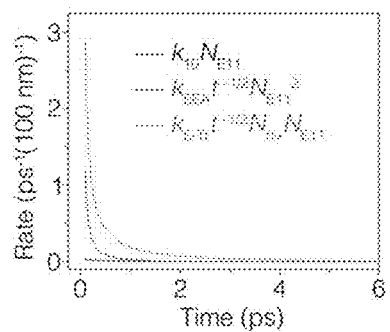
Figure 33C:
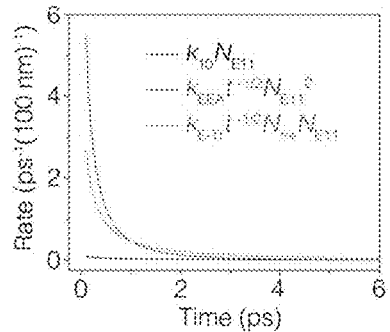

FIGS. 33A-33C show plots of exciton decay rate evaluated as a function of exciton intrinsic decay, EEA, and trion formation decay channels. FIG. 33A shows excitons intrinsic decay rate, EEA rate, and trions formation rate as a function of time, initial [h+]=14.3 (100 nm)$^{-1}$. FIG. 33B shows excitons intrinsic decay rate, EEA rate, and trions formation rate as a function of time, initial [h+]=6.1 (100 nm)$^{-1}$. FIG. 33C shows excitons intrinsic decay rate, EEA rate, and trions formation rate as a function of time, initial [h+]=3.5 (100 nm)$^{-1}$.

FIGS. 34A and 34B show representative transient absorption spectra obtained for heavily hole-doped S-PBN(b)-Ph5-[(6,5) SWNTs] following excitation at 1000 nm (excitation photon flux: 9.1×1011 pulse$^{-1}$). FIG. 34A shows transient absorption spectra at selected time delays for heavily hole-doped S-PBN(b)-Ph5-[(6,5) SWNTs] following excitation at 1000 nm (excitation photon flux: 9.1×1011 pulse-1). FIG. 34B shows transient absorption spectra at selected time delays for heavily hole-doped S-PBN(b)-Ph5-[(6,5) SWNTs] following excitation at 1130 nm (excitation photon flux: 1.1×1012 pulse$^{-1}$).

FIG. 35 shows kinetic traces representative of dynamics for $E_{11}$ excitons and hole trions in heavily hole-doped S-PBN(b)-Ph5-[(6,5) SWNTs].

Figure 36A:
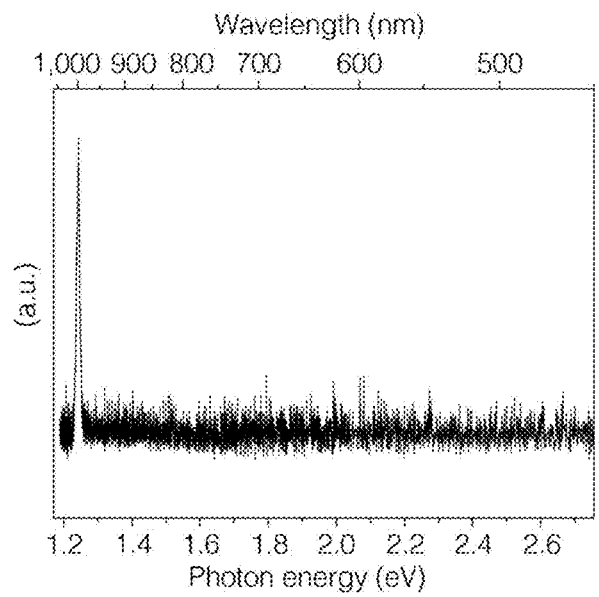
Figure 36B:
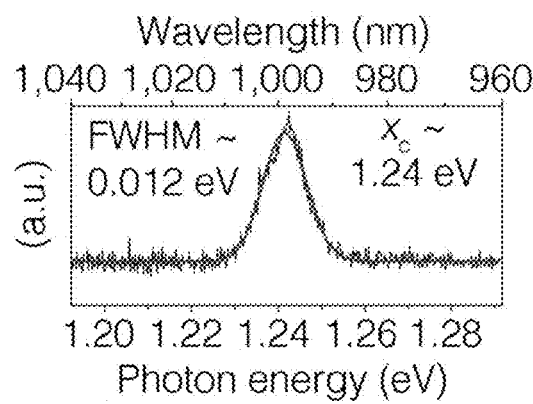
Figure 36C:
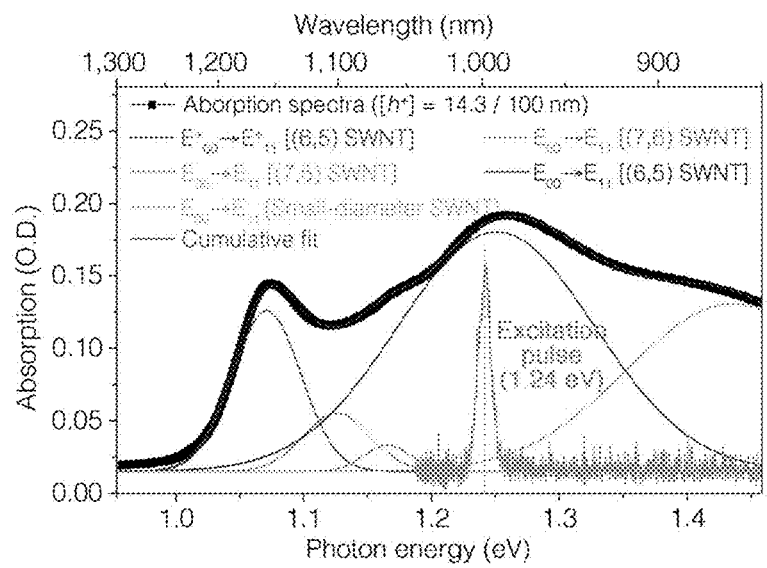

FIGS. 36A-36C show characterizations of excitation laser pulse. FIG. 36A shows 1.24 eV energy laser pulse characterized using a fiber optic path cable (Ocean Optics); FIG. 36B shows a plot at; the FWHM (0.012 eV) and center energy (Xc~1.24 eV) of the laser pulse, fitted by a Gaussian function. FIG. 36C shows overlap of the 1.24 eV laser pulse with the deconvoluted steady-state absorption spectra of hole-doped SWNTs as shown in FIG. 25.

DETAILED DESCRIPTION

Control of trion density in carbon nanotubes for electro-optical and opto-electric devices is provided. Trion-density controlled nanotube devices and the techniques and systems for designing such devices are described. An optoelectronic system can include a single walled carbon nanotube (SWNT) device. The SWNT can include a carrier-doping density with optical conditions that control trion formation that respond via optical, electrical, or magnetic stimuli. The carrier-doping density can include a hole-polaron or electron-polaron concentration.

A graphical computer-aided design environment or tool for the design, analysis, and layout of carbon nanotube-based devices can incorporate the described modeling feature for control of trion density. Such a modeling feature can include a one dimensional (1D) kinetic model of trion formation and decay dynamics. A computer program product such as in the form of one or more computer-readable storage media can be provided having instructions stored thereon, that when executed by a processor, direct the processor to at least generate a model of trion formation and decay dynamics for a single walled carbon nanotube (SWNT) device. The model can include a set of differential equations. The media can further include instructions to quantify free carrier generation in a SWNT of the SWNT device.

Trions transmit spin, charge, and excitation. Optical excitation of the semiconducting single-walled carbon nanotube (SWNT) charged ground state ($E^+_{00}$) gives rise to trions even at room temperature due to the drastically increased $\Delta E_{Tr}$ (change in trion energy level) of ~100 meV in 1D SWNTs that arises from reduced dielectric screening. However, charge-doped 1D SWNTs do not possess a direct $E^+_{00} \rightarrow Tr^+_{11}$ (ground level to excited trion level) optical transition.

Owing to the substantial $\Delta E_{Tr}$, the tightly bound trion quasi-particles in SWNTs offer new opportunities to manipulate charge, spin, and excitonic energy at room temperature. To fully understand and exploit the exceptional potential of SWNT trion species, the dynamics and mechanisms that characterize their creation and decay are provided.

Through the methods described herein (see sections entitled Experimental Data), the trion transient absorptive hallmark was identified at 1,190-nm. The experiments included obtaining ground-state absorption and pump-probe transient absorptive dynamical data for hole-doped SWNTs. From the data, the representative transient absorption spectra of heavily hole-doped S-PBN(b)-Ph$_5$-[(6,5) SWNT] superstructures ([h$^+$]~14.3 (100 nm)$^{-1}$) manifest $E_{00} \rightarrow E_{11}$ (~1,000 nm) and $E^+_{00} \rightarrow E^+_{11}$ (~1,150 nm) bleaches, as well as a signal having an absorption maximum near 1,190 nm were identified. Importantly, this transient absorption manifold centered at 1,190 nm is absent in undoped, neutral S-PBN(b)-Ph$_5$-[(6,5) SWNTs], suggesting its correlation with nanotube polarons.

Given the excess of polarons relative to excitons in SWNTs for the above-mentioned pump-probe experiment ([$E_{11}$]~0.6 (100 nm)$^{-1}$; [h$^+$]~14.3 (100 nm)$^{-1}$), it was hypothesized that before EEA events, optically generated $E_{11}$ excitons diffuse to nearby hole-polaron sites and are trapped, forming hole trions. Furthermore, $E_{11}$ exciton decay in hole-doped SWNTs clearly correlates with the rise of the nascent transient absorption signal at 1,190 nm within ~0.5 ps. As such, the correspondingly evolved transient absorption manifold centered at 1,190 nm is attributed to a trion transient absorptive hallmark ($Tr^+_{11} \rightarrow Tr^+_{nm}$, where $Tr^+_{nm}$ denotes a higher-lying hole-trion electronically excited state of the hole-trion kinetic state) based on dynamics analysis. Accordingly, in some cases, trion formation can be characterized by a SWNT trion transient absorptive signature ($Tr^+_{11} \rightarrow Tr^+_{nm}$ for hole-polaron based or $Tr^-_{11} \rightarrow Tr^-_{nm}$ for electron-polaron based).

It was found that trions (i) derive from a precursor excitonic state, (ii) are produced via migration of excitons to stationary hole-polaron sites, and (iii) decay in a first-order manner.

Importantly, under appropriate carrier-doping densities, exciton-to-trion conversion (e.g., via optical stimuli) in SWNTs can approach 100% at ambient temperature. These findings can be used to exploit trions in SWNT optoelectronics, ranging from photovoltaics and photodetectors to spintronics—effectively any optoelectronic device that relies upon manipulating spin, energy, and charge.

Figure 1:
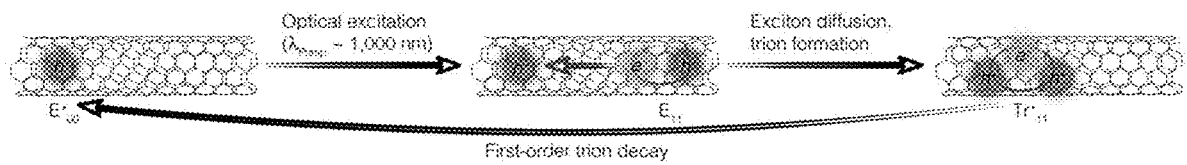
FIG. 1 shows a schematic description of hole-trion formation in hold-doped, optically excited semiconducting SWNTs.
Figure 2:
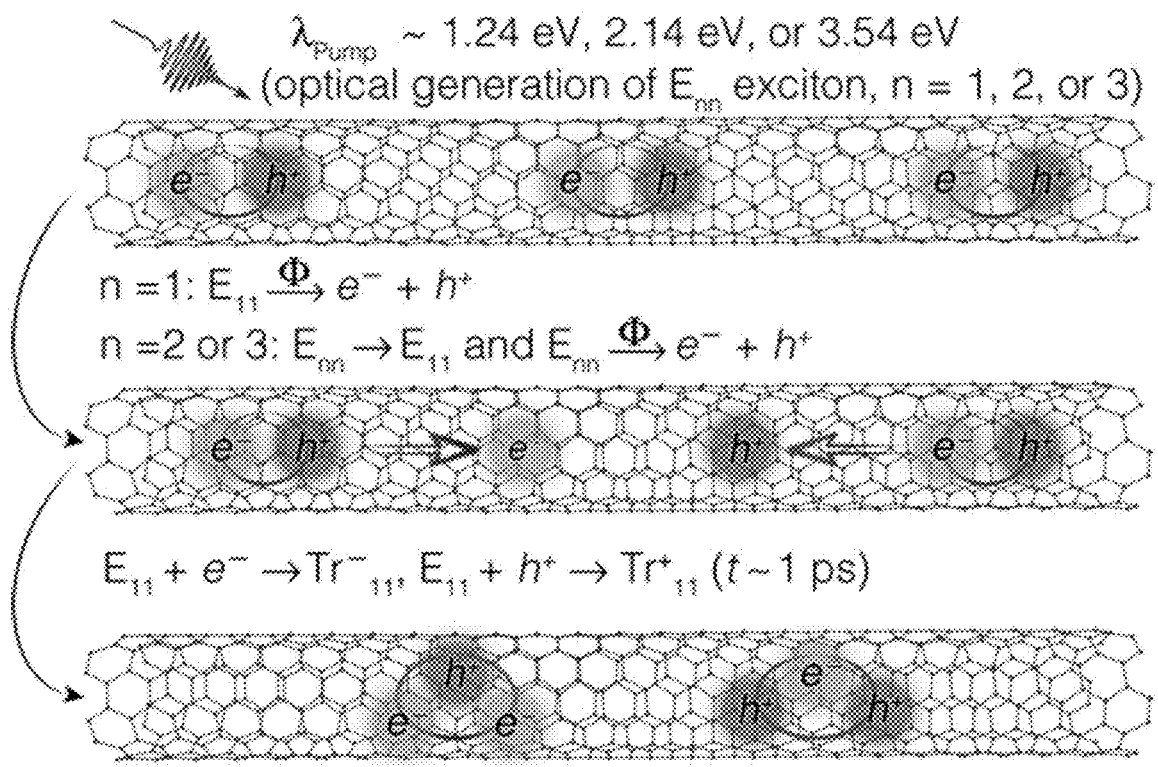
FIG. 2 shows a schematic illustration of trion formation in neutral, optically pumped SWNTs.

FIG. 1 shows a schematic description of hole-trion formation in hole-doped, optically excited semiconducting SWNTs. FIG. 2 shows a schematic illustration of trion formation in neutral, optically pumped SWNTs. In FIG. 2, ultrafast trion formation in neutral SWNTs is shown following (i) optical production of $E_{nn}$ excitons (n=1, 2, or 3, depending on excitation energy), (ii) exciton dissociation into unbound h+ and e−, and (iii) exciton migration to hole (h+) or electron (e−) polaron sites and trion formation.

Kinetic modeling of exciton and trion signals reveals that trions form via the diffusion of excitons to hole polaron (or electron polaron) sites; once formed, these quasi-particles decay in a first-order manner.

FIG. 3 shows an energy band diagram depicting a 1D diffusion kinetic model of trion formation and decay dynamics. FIG. 3 is the diagrammatic representation of the four-state model used to fit the $E_{00} \rightarrow E_{11}$ and $Tr^+_{11} \rightarrow Tr^+_{nm}$ kinetic traces, where the $N_X(t)$ (X=$E_{11}$, $E_{11,2}$, $Tr^+_{11}$, or $h^+$) corresponds to the densities [$(100 \text{ nm})^{-1}$] of these quasi-particles at a certain time t, $k_{10}$ is the intrinsic first-order decay rate constant for bright singlet excitons in (6,5) SWNTs, $k_{21}$ is the rate constant for the first-order decay from the second to the first exciton subband, $k_{Tr}$ is the first-order decay rate constant of trions, $k_{EEA}t^{-1/2}N_{E11}$ is the EEA rate constant, and $k_{E-Tr}t^{-1/2}N_{h+}$ is the trion formation rate. Note that all rate constants are in units of $ps^{-1}$.

As can be seen, the 1D diffusion kinetic model depicted in FIG. 3 also takes into account 1D diffusion-controlled EEA processes explicitly described by Lüer et al. ("Size and mobility of excitons in (6,5) carbon nanotubes," Nat Phys. 2009; 5:54-58). In the illustrated 1D diffusion kinetic model, it is assumed that hole- or electron-polarons in 1D SWNTs in $D_2O$ are stationary sites on the timescale of these experiments (akin to a 1D Wigner crystal such as described by Deshpande V V, Bockrath M. "The one-dimensional Wigner crystal in carbon nanotubes," Nat Phys. 2008; 4:314-318), contrasting the mobile nature of excitons. This assumption is justified by considering the long-range Coulomb repulsion among positively charged quasi-particles, and the fact that migration of such species is accompanied with significant outer-sphere reorganization energy in the condensed phase.

Based on the 1D diffusion kinetic model shown in FIG. 3, the relevant rate equations/ordinary differential equations (ODEs) are given as follows.

$$\frac{dN_{E_{11}}}{dt} = -k_{10}N_{E_{11}} - k_{EEA}(t-t_0)^{-\frac{1}{2}}N_{E_{11}}^2 + k_{21}N_{E_{11,2}} - k_{E-Tr}(t-t_0)^{-\frac{1}{2}}N_{h^+}N_{E_{11}}. \quad \text{ODE [1]}$$

$$\frac{dN_{E_{11,2}}}{dt} = \frac{1}{2}k_{EEA}(t-t_0)^{-\frac{1}{2}}N_{E_{11}}^2 - k_{21}N_{E_{11,2}}. \quad \text{ODE [2]}$$

$$\frac{dN_{Tr_{11}^+}}{dt} = k_{E-Tr}(t-t_0)^{-\frac{1}{2}}N_{h^+}N_{E_{11}}^2 - k_{Tr}N_{Tr_{11}^+}. \quad \text{ODE [3]}$$

$$\frac{dN_{h^+}}{dt} = -k_{E-Tr}(t-t_0)^{-\frac{1}{2}}N_{h^+}N_{E_{11}} + k_{Tr}N_{Tr_{11}^+}. \quad \text{ODE [4]}$$

In the above ODEs, $N_X$ (X=$E_{11}$, $E_{11,2}$, $Tr^+_{11}$, or $h^+$) is the density (/100 nm) for the corresponding quasi-particles, $k_{10}$=0.048 $ps^{-1}$ is the intrinsic first-order decay rate constant for bright singlet excitons in (6,5) SWNTs, $k_{21}$=23 $ps^{-1}$ is the rate constant for the first-order decay from the second to the first exciton subband, $k_{Tr}$ is the first-order decay rate constant of trions, $k_{EEA}(t-t_0)^{-1/2}$ is the EEA rate constant, and $k_{E-Tr}(t-t_0)^{-1/2}$ is the trion formation rate constant.

Note that (i) $t_0$ is a fitting parameter; (ii) the $(t-t_0)^{-1/2}$ dependence of EEA and hole trion formation processes originate from 1D diffusion; and (iii) $k_{E-Tr}=k_{EEA}/2\sqrt{2}$.

Providing initial values for Nx, the optimal numerical solutions of the four above described ODEs can be solved in the process of fitting the experimentally acquired $E_{11}$ and $Tr^+_{11}$ kinetics. A more detailed description regarding kinetic modeling is provided in the sections entitled Experimental Data.

Figure 4:
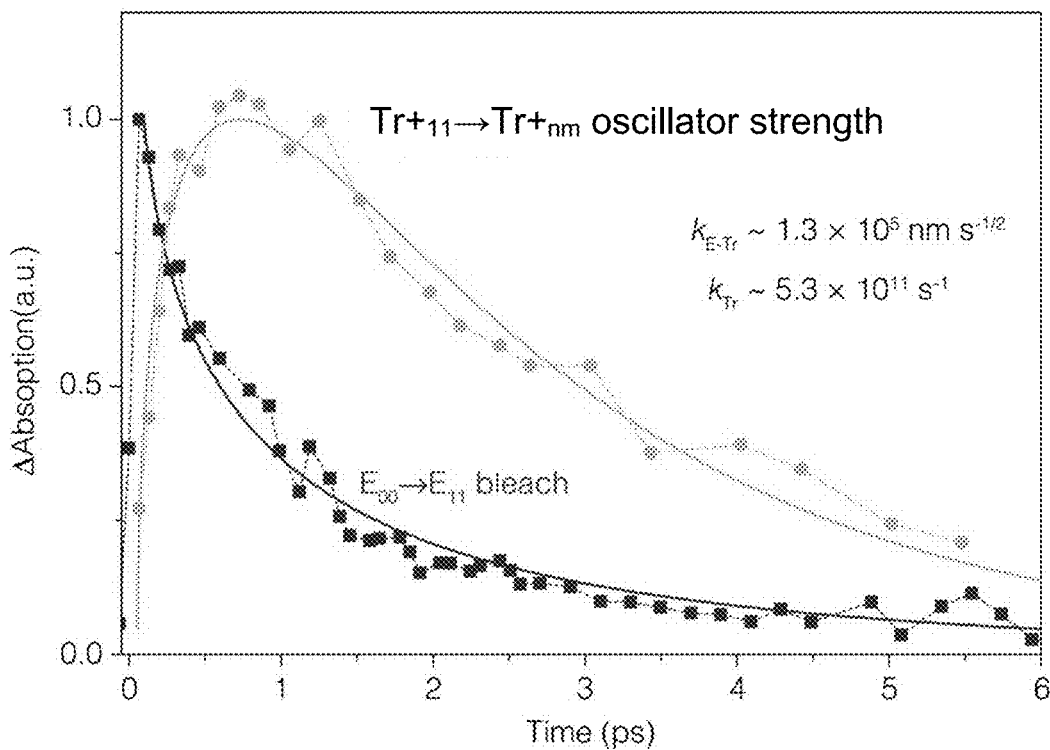
FIG. 4 shows Kinetic traces for $E_{00} \rightarrow E_{11}$ bleaching oscillator strength (scattered square), $Tr^+_{11} \rightarrow Tr^+_{nm}$ transient absorption oscillator strength (scattered circle), and corresponding numerical fits (solid curves) obtained using the kinetic model depicted in FIG. 3.

FIG. 4 shows Kinetic traces for $E_{00} \rightarrow E_{11}$ bleaching oscillator strength (scattered square), $Tr^+_{11} \rightarrow Tr^+_{nm}$ transient absorption oscillator strength (scattered circle), and corresponding numerical fits (solid curves) obtained using the kinetic model depicted in FIG. 3. Note that data represented in FIG. 4 do not correspond to single-wavelength kinetics, as they are acquired from integrated Gaussian functions fitted to the corresponding spectral signals.

As shown in FIG. 4, the agreement between the kinetic model and the experimental data provides compelling proof of a diffusion-controlled trion formation mechanism, and determines directly SWNT hole trion formation and decay constants ($k_{Tr} \sim 5.4 \times 10^{11}$ $s^{-1}$, and $k_{E-Tr} \sim 4.5 \times 10^6$ nm $s^{-1/2}$).

Figure 5:
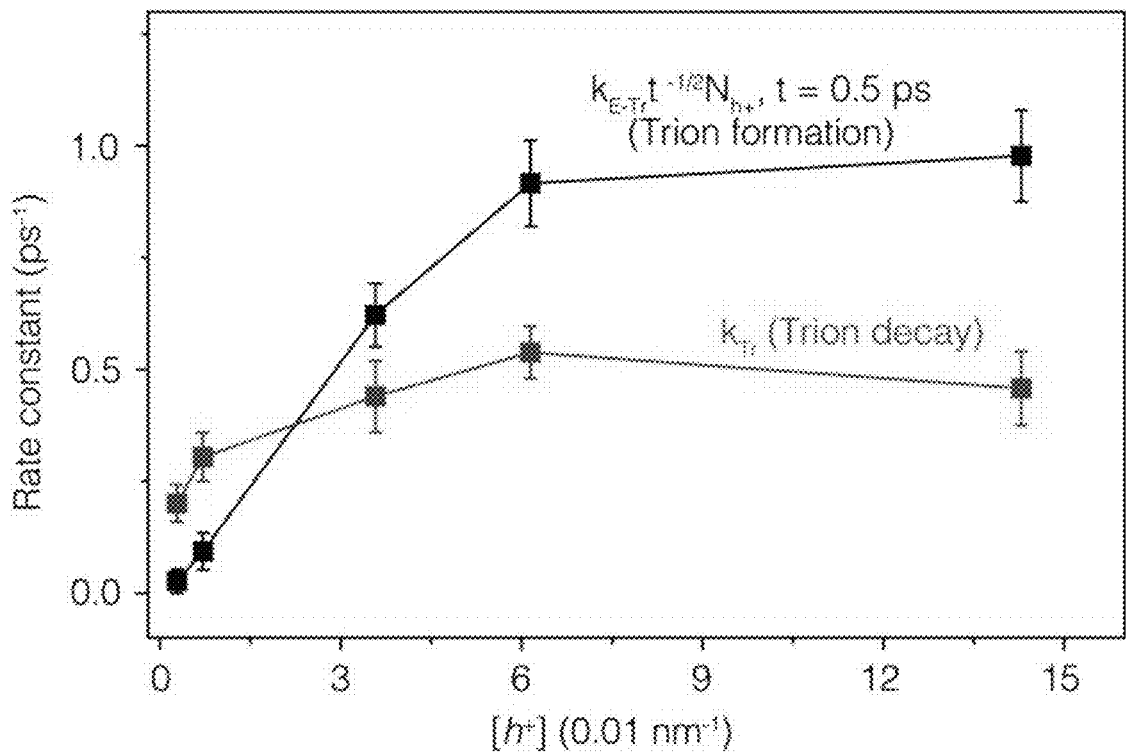
FIG. 5 shows a summary plot of hole trion formation and decay rate constants as a function of hole polaron concentration [$h^+$].

FIG. 5 shows a summary plot of hole trion formation and decay rate constants as a function of hole polaron concentration [$h^+$]. Note that the hole trion formation rate constant is determined from the expression $k_{E-Tr}t^{-1/2}N_{h+}$ (as both exciton and hole polaron concentrations vary as a function of time); here t is selected at 0.5 ps; as [$h^+$] is a function of time, this value is acquired from numerical simulation based on rate equations derived from the kinetic model shown in FIG. 3; hole trion decay rate constants are directly represented by $k_{Tr}$, as trion decay is a first-order process (a 3D plot describing hole trion formation and decay dynamics as functions of time and [$h^+$] is shown in FIGS. 16A-16F). Error bars represent the uncertainty from fitting the exciton and trion kinetic traces.

As can be seen from the dynamical data in FIG. 4, the trion formation rate constant, $k_{E-Tr}*=k_{E-Tr}t^{-1/2}N_h^+$, depends on initial [$h^+$], with $k_{E-Tr}*$ increasing monotonically from $3 \times 10^{11}$ to $1 \times 10^{12}$ $s^{-1}$ as [$h^+$] increases from 0.3 to 14.3 (100 nm)$^{-1}$, while $k_{Tr}$ does not ($\overline{k_{Tr}}$=3.9×10$^{11}$ $s^{-1}$, $\sigma_{SD} \sim 1.3 \times 10^{11}$ $s^{-1}$, where $\overline{k_{Tr}}$ is the average value for $k_{Tr}$, and $\sigma_{SD}$ is the SD of $k_{Tr}$) (See sections entitled Experimental Data). These observations are congruent with the 1D diffusion-controlled trion formation/decay picture highlighted in FIG. 1.

Additionally, as $k_{EEA} \sim \sqrt{32D_{E11}/\pi}$, where $D_{E11}$ represents the exciton diffusion constant, a $D_{E11}$ value of $\sim 0.9$ cm$^2$ $s^{-1}$ was obtained for S-PBN(b)-Ph$_5$-[(6,5) SWNTs] dispersed in $D_2O$; note that this value is of the same order of magnitude compared with exciton diffusion constants derived from pump-probe measurements of xerogel-dispersed SWNTs and fluorescence quenching studies of SWNTs suspended in agarose gels. Furthermore, an exciton diffusion length may be determined from the relation $L_{E11}=\sqrt{D_{E11}\tau_{E11}}$ (where $\tau_{E11}$ is the exciton decay time constant). For [$h^+$]~14.3 (100 nm)$^{-1}$ SWNTs, $\tau_{E11}$ is ~0.5 ps, indicating that $L_{E11}$ is ~6 nm, which matches closely the half spatial separation between hole polarons ($d_{h+}/2 \sim 3.5$ nm). This correlation between $L_{E11}$ and $d_{h+}/2$ is consistent with the notion that trion formation in optically excited hole-doped SWNTs derives from an exciton diffusion process that occurs on a timescale over which hole polarons are effectively stationary.

The experimental data and the corresponding numerical simulation of these results indicate that exciton-to-trion conversion can approach unity under hole-doping levels that range from 6.1 to 14.3 (100 nm)$^{-1}$. Based on the kinetic model in FIG. 3, the exciton decay rate in hole-doped SWNTs is determined by:

$$\left(\frac{dN_{E_{11}}}{dt}\right)_{decay} = (-k_{10}N_{E_{11}}) + \left(-k_{EEA}t^{-\frac{1}{2}}N_{E_{11}}^2\right) + \left(-k_{E-Tr}t^{-\frac{1}{2}}N_{h^+}N_{E_{11}}\right),$$

wherein ($-k_{10}N_{E11}$), $$\left(-k_{EEA}t^{-\frac{1}{2}}N_{E11}^2\right), \text{ and } \left(-k_{E-Tr}t^{-\frac{1}{2}}N_{h^+}N_{E11}\right)$$

represent the three exciton decay channels (intrinsic first-order decay, EEA, and trion formation, respectively). Using the $k_{EEA}$ and $k_{E-Tr}$ values obtained in these studies, the numerical simulations demonstrate that trion formation defines the dominant exciton decay channel for hole-doped SWNTs in which hole-polaron concentration [h$^+$] ranges from about 6.1 to about 14.3 (100 nm)$^{-1}$ (and similarly for electron-polaron concentration).

This work further establishes a SWNT hole trion transient absorptive signature ($Tr^+_{11} \to Tr^+_{nm}$): as trion formation requires the coexistence of an exciton and a charge carrier, the $Tr^+_{11} \to Tr^+_{nm}$ transition defines an unequivocal spectroscopic fingerprint for any study that aims to investigate optically driven free-carrier generation in SWNTs. Furthermore, under appropriate charge-doping conditions ([h$^+$] ~6.1~14.3 (100 nm)$^{-1}$), exciton-to-trion conversion can approach 100% following optical stimuli. Because these tightly bound trions undergo drift in electric field, which results in simultaneous transportation of energy, charges, and spin, these trion formation and decay dynamical data may guide design of new SWNT-based optoelectronic devices important for photovoltaics, photodetectors, and spintronics.

Thus, a SWNT-based optoelectronic device can include a carrier-doping density with optical conditions that control trion formation that respond via optical, electrical, or magnetic stimuli. The carrier-doping density can include a hole-polaron or electron-polaron concentration, which in some cases can be between about 6.1 to about 14.3 (100 nm)$^{-1}$. In some cases, the trion formation is characterized by a trion response to a magnetic field. In some cases, the trion formation is characterized by a trion response to an electrical input. In some cases, the trion formation is characterized by a trion response to an optical input. In some cases, the trion formation is characterized by a trion migration rate to an electrode. In some cases, trion formation is characterized by an absorptive signature of $Tr^+_{11} \to Tr^+_{nm}$ or $Tr^-_{11} \to Tr^-_{nm}$.

Free-carrier generation can be quantified using trion transient spectroscopic signature. As trion formation requires the coexistence of an exciton and a charge carrier, the $Tr^{+/-}_{11} \to Tr^{+/-}_{nm}$ transitions can be exploited as an unequivocal spectroscopic fingerprint to quantify photogenerated free carriers, for example, in neutral S-PBN(b)-Ph$_5$-[(6,5) SWNTs]. This approach for quantifying intrinsic FCG in SWNTs is powerful for the following reasons: (i) trion formation is orders of magnitude more rapid than free carrier recombination dynamics; i.e., prior to the recombination of charge carriers, charges combine with neutral excitons to form trions.

Figure 6A:
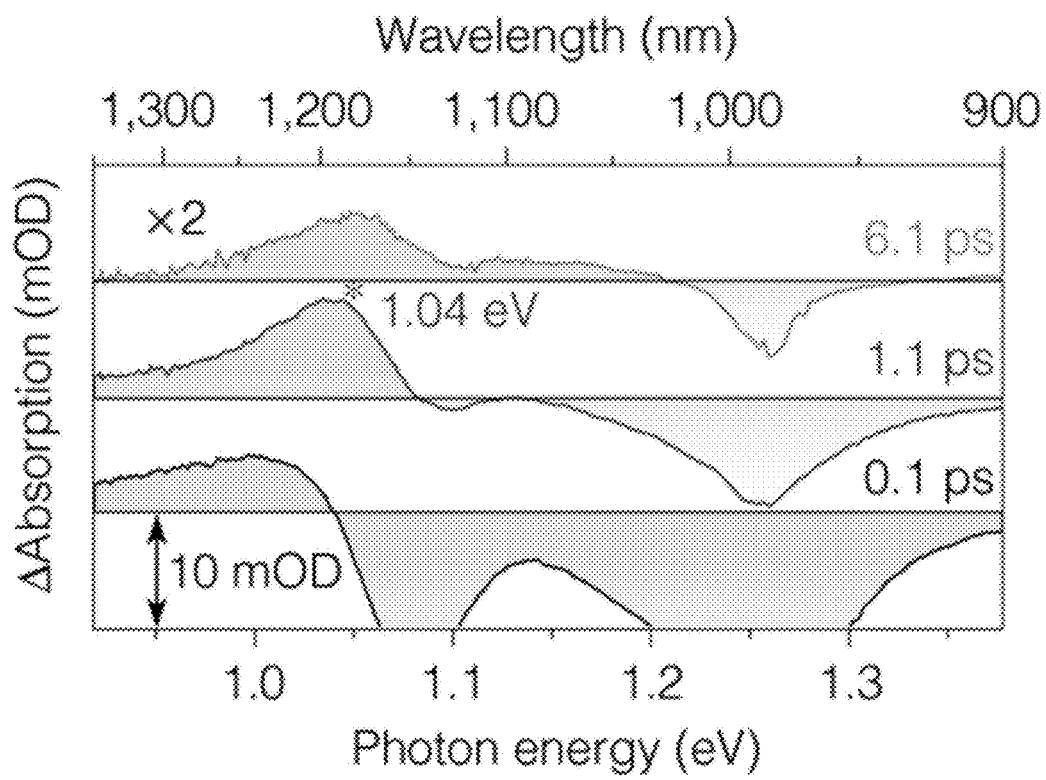
FIGS. 6A-6I show trion signals from optically pumped, charge-doped, and neutral polymer-wrapped SWNTs.
Figure 6B:
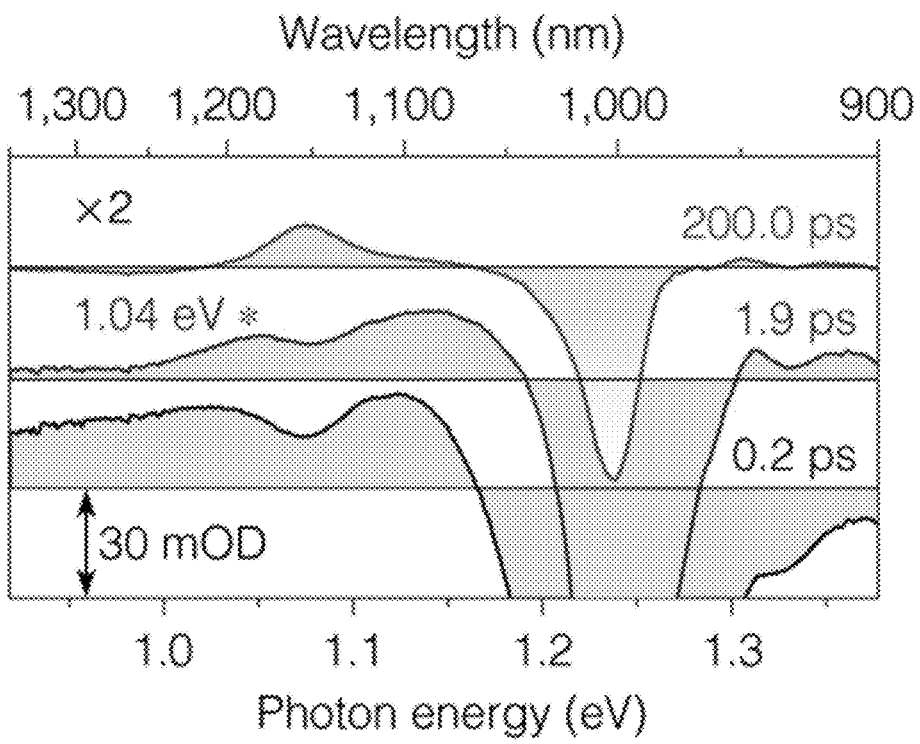
Figure 6C:
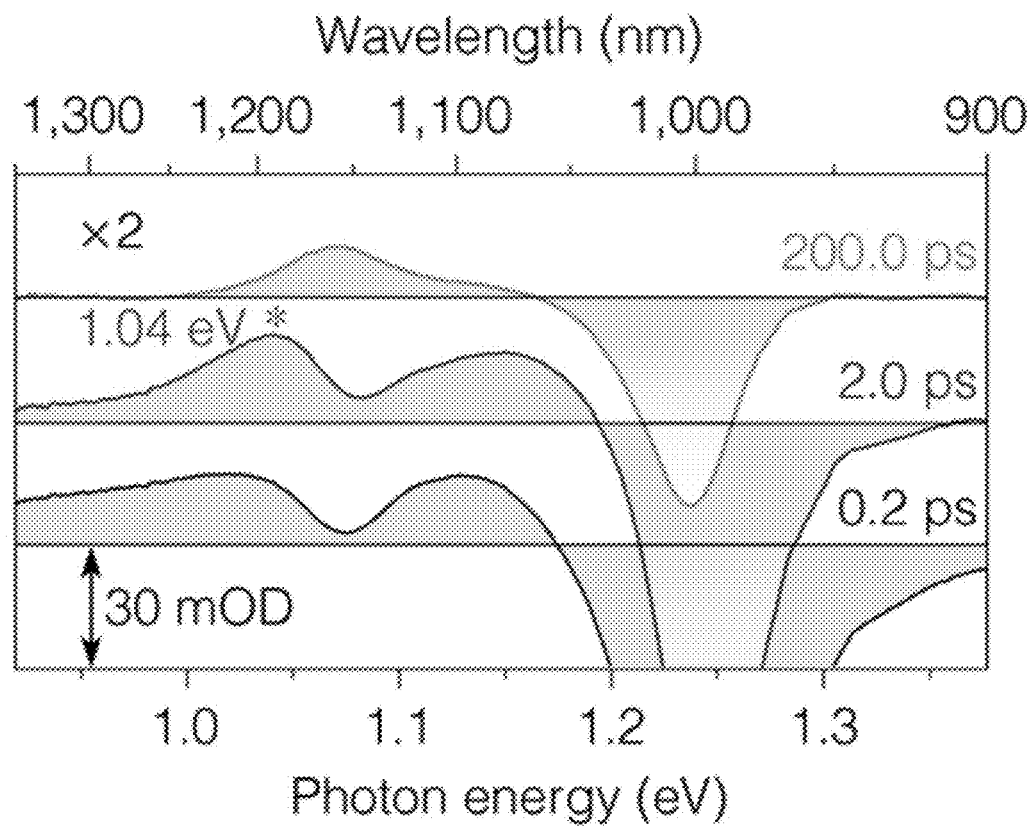
Figure 6D:
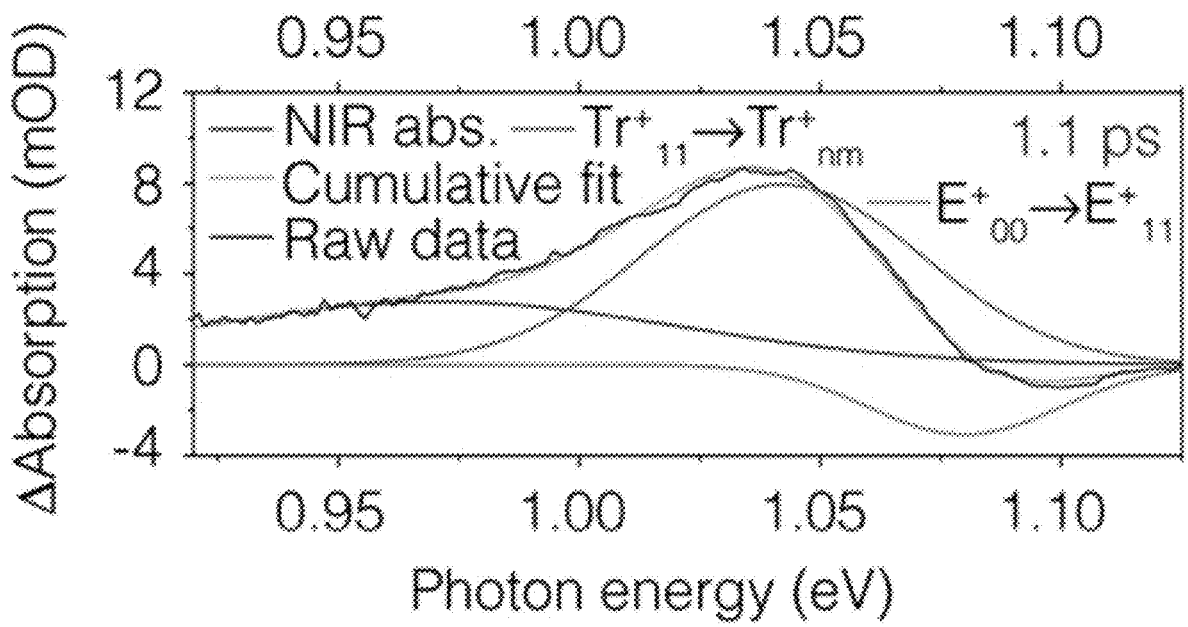
Figure 6E:
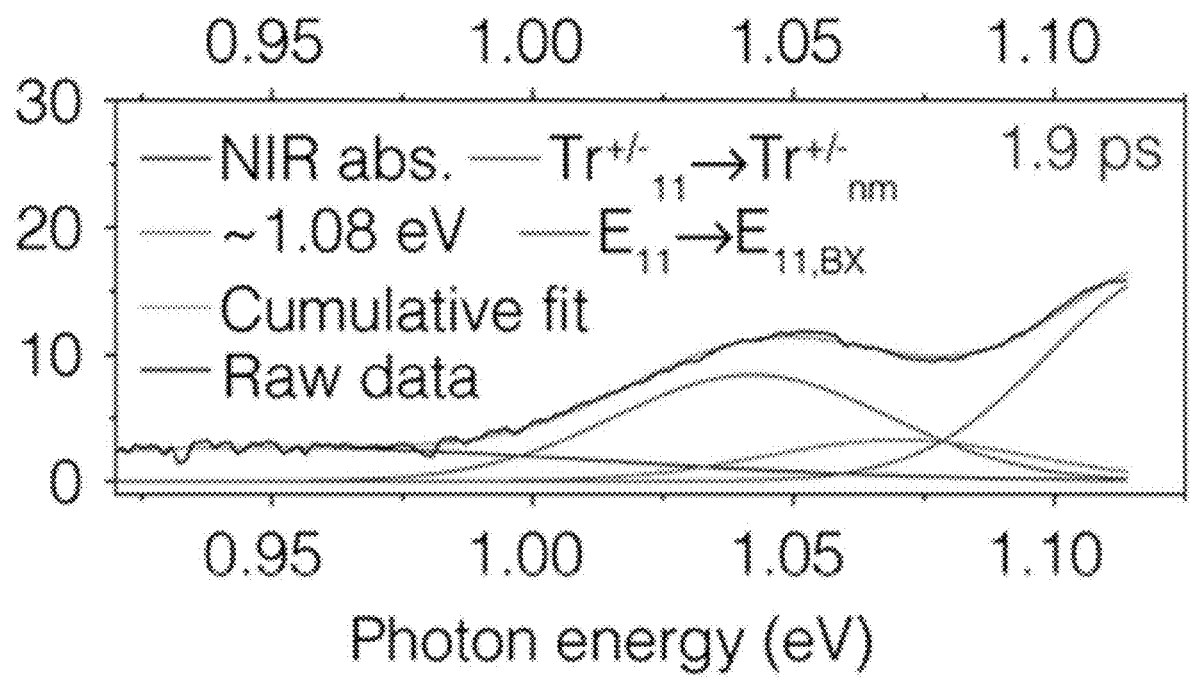
Figure 6F:
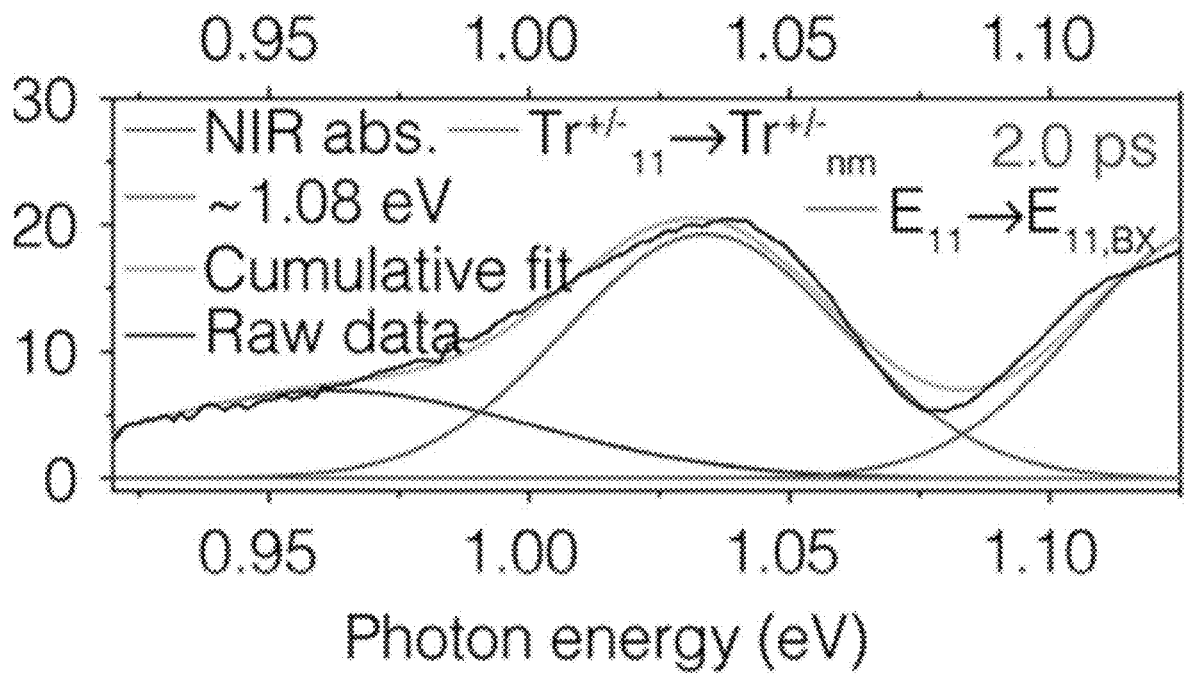
Figure 6G:
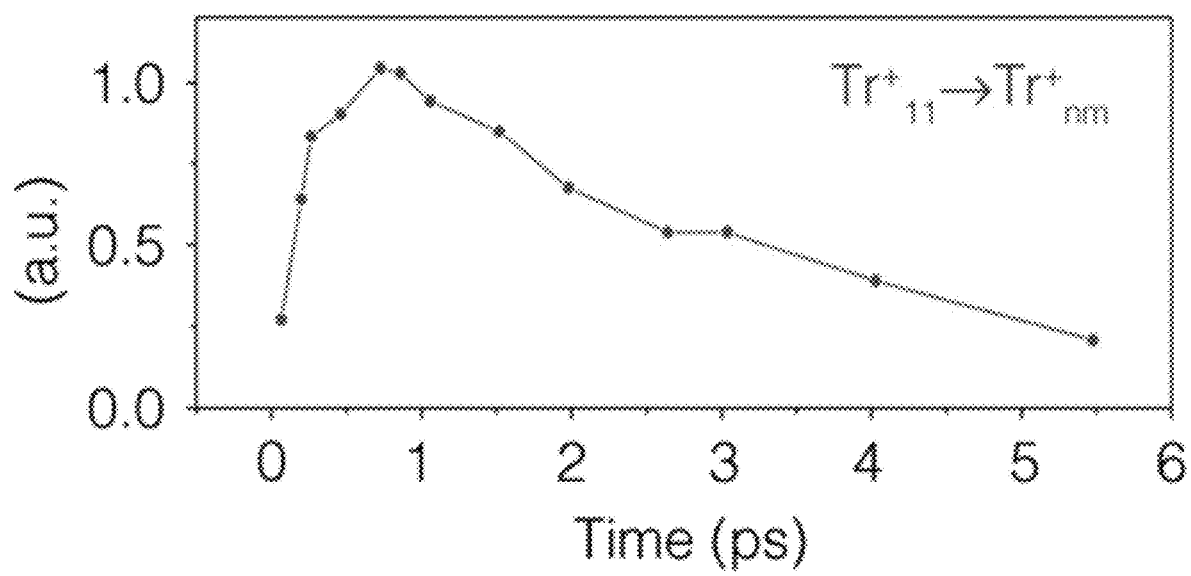
Figure 6H:
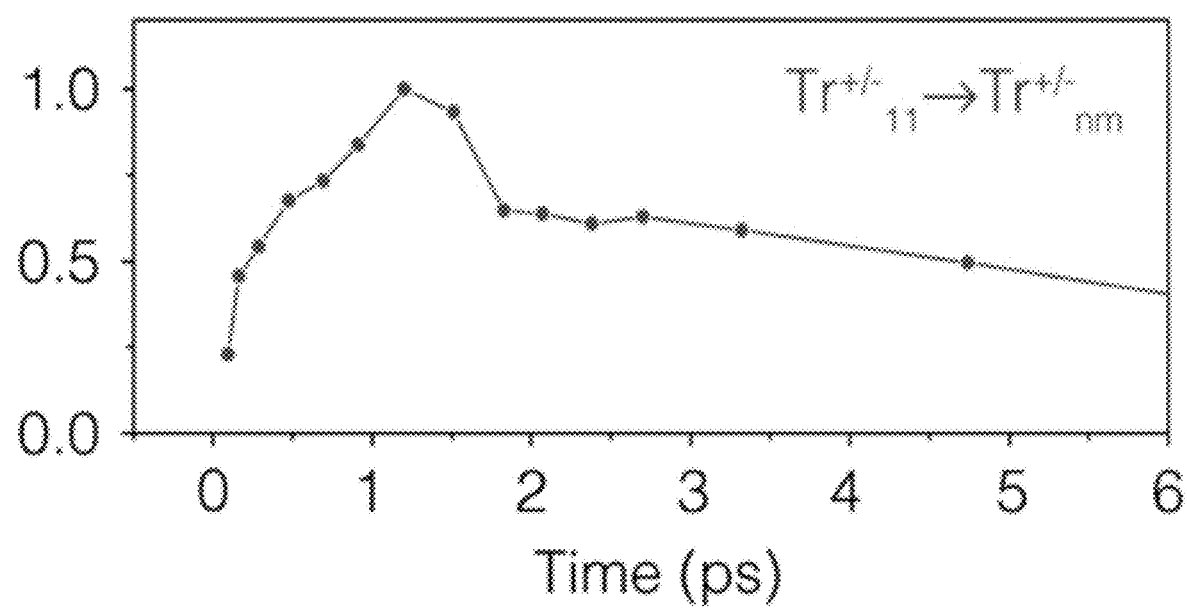
Figure 6I:
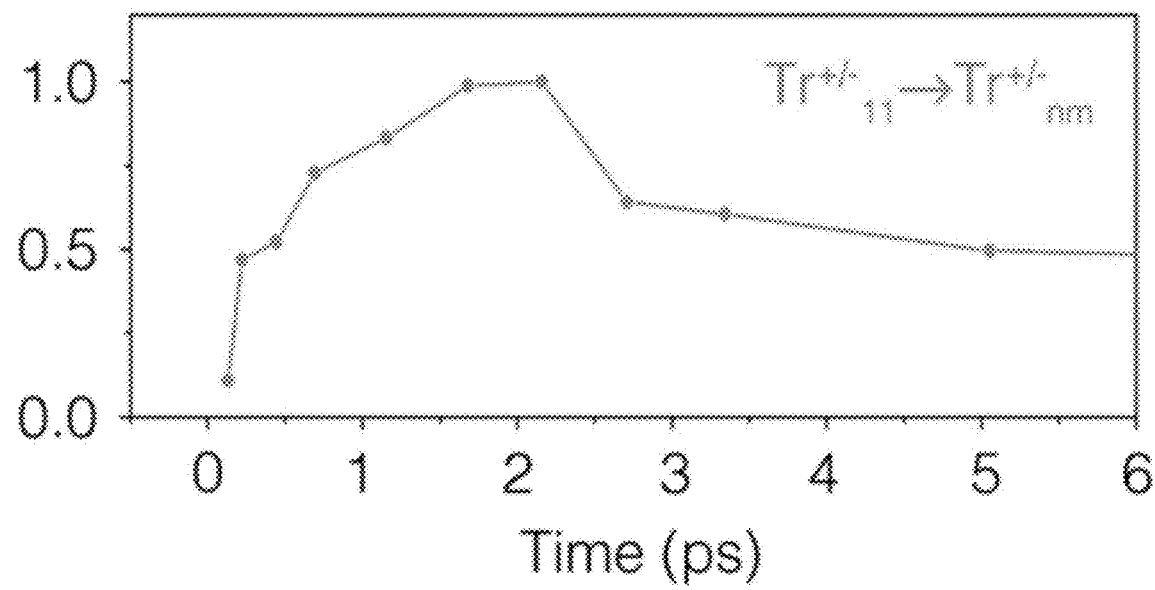

FIGS. 6A-6I show trion signals from optically pumped, charge-doped, and neutral polymer-wrapped SWNTs. FIG. 6A shows representative transient absorption spectra of hole-doped S-PBN(b)-Ph$_5$-[(6,5) SWNTs] at selected time delays (hv$_{pump}$~1.24 eV, i.e., in resonance with the $E_{00} \to E_{11}$ transition, excitation fluence=140 µJ·cm$^{-2}$·pulse$^{-1}$). FIGS. 6B and 6C show representative transient absorption spectra of neutral S-PBN(b)-Ph5-[(6,5) SWNTs] at selected time delays, where FIG. 6B has hv$_{pump}$~2.13 eV, i.e., in resonance with the $E_{00} \to E_{22}$ transition, excitation fluence=341 µcm$^{-2}$·pulse$^{-1}$; and FIG. 6C has hv$_{pump}$~3.54 eV, i.e., in resonance with the $E_{00} \to E_{33}$ transition, excitation fluence=244 µJ·cm$^{-2}$·pulse$^{-1}$). In FIGS. 6A-6C, the signal labeled at ~1.04 eV (*) denotes the trion transient absorption hallmark. FIGS. 6D-6F show Gaussian deconvolutions of pump-probe spectra at selected time delays, where FIG. 6D has $t_{delay}$~1.1 ps; FIG. 6E has $t_{delay}$~1.9 ps; and FIG. 6F has $t_{delay}$~2.0 ps), highlighting the major transitions that occur within the NIR probe spectral domain. For FIGS. 6D-6F, the cumulative fit reflects combined contributions of the noted individual transition manifolds at the time delay noted. FIG. 6G shows time-dependent evolution of $Tr^+_{11} \to Tr^+_{nm}$ transient absorption oscillator strength in hole-doped S-PBN(b)-Ph$_5$-[(6,5) SWNTs]; this kinetic trace was extracted from the data set of FIG. 6A. FIGS. 6H and 6I show time-dependent evolution of $Tr^{+/-}_{11} \to Tr^{+/-}_{nm}$ transient absorption oscillator strength in neutral S-PBN(b)-Ph$_5$-[(6,5) SWNTs]; in FIGS. 6H and 6I, kinetic traces were extracted from the respective data sets of FIGS. 6B and XC. It should be noted that the kinetic traces presented in FIGS. 6G-6I do not correspond to single-wavelength kinetics, as they are generated from the Gaussian peak areas fitted to the corresponding spectral signals.

As can be seen in FIGS. 6H and 6I, the trion formation process can be evaluated by monitoring the increase of the $Tr^{+/-}_{11} \to Tr^{+/-}_{nm}$ transition amplitude; and trion species form in ~1-2 ps, whereas optically generated free carriers recombine over a time domain greater than nanoseconds. Following $E_{00} \to E_{nm}$ excitation, optically generated free carriers in neutral SPBN(b)-Ph$_5$-[(6,5) SWNTs] are converted into trions within ~2 ps (see the section entitled Experimental Data for additional details).

As such, the quantum yield of optically driven FCG can be estimated by $$\Phi(E_{nm} \to h^+ + e^-) = \frac{N_{h+}}{N_{Ex}} = \frac{N_{e-}}{N_{Ex}} \approx \frac{N_{Tr+/-11}}{2N_{Ex}}$$

wherein $N_{h+}(N_{e-})$ is the h$^+$(e$^-$) density (per 100 nm), $N_{Ex}$ is the approximate exciton density (per 100 nm) produced following $E_{00} \to E_{nm}$ excitation, and $N_{Tr+/-11}$, which represents the maximum trion density following optical excitation, and reflects the combined $N_{Tr+11}$ and $N_{Tr-11}$ positive and negative trion densities. $N_{Ex}$ can be experimentally determined as detailed in previous investigations. Under excitation fluences above 20 µJ·cm$^{-2}$, saturable absorption occurs in the SWNT samples; as such, for these experiments, $N_{Ex}$ should be corrected for the reduced transmission of the pump pulse and calibrated using the maximum $E_{00} \to E_{11}$ bleach intensity from transient absorbance measurements using fluences less than 10 µJ·cm$^{-2}$. The remaining unknown parameter is $N_{Tr+/-11}$.

$N_{Tr+/-11}$ can be calculated on the basis of the following relationship $$A = \sigma_{Tr} l C_{SWNT} N_A L_{SWNT} N_{Tr+/-11}$$

where A is the absorbance corresponding to the $Tr^{+/-}_{11} \to Tr^{+/-}_{nm}$ transition, $\sigma_{Tr}$ is the absorption cross section associated with the $Tr^{+/-}_{11} \to Tr^{+/-}_{nm}$ transition, l is the optical path length of the spectral cuvette, $C_{SWNT}$ is the SWNT molar concentration, $N_A$ is the Avogadro constant, and $L_{SWNT}$ is the average length (~700 nm) of the SWNTs.

Among these parameters, l, $N_A$, and $L_{SWNT}$ are known, $C_{SWNT}$ can be determined following previously established protocols, $\sigma_{Tr}$ can be estimated on the basis of the results from previous spectroscopic studies of positive trion species, while a relatively accurate A can be determined via spectral deconvolution of the NIR pump-probe transient spectral data over the energy regime where the $Tr^{+/-}_{11} \rightarrow Tr^{+/-}_{nm}$ transition occurs (see sections entitled Experimental Data for details regarding the determination of $\sigma_{Tr}$ and A). Again, due to the similar effective masses of $h_+$ and $e_-$ in SWNTs, positive and negative trions should possess similar optical properties; in this regard, the $\sigma_{Tr}$ (~$2.16\times10_{-16}$ cm$_2$/trion) acquired for positive trions is also used as a constant for estimating $N_{Tr+/-11}$.

This method for quantifying optical free-carrier generation in SWNTs is suitable for a broad range of pump fluences that range from hundreds of $\mu J \cdot cm^{-2} \cdot pulse^{-1}$ to ~15 $\mu J \cdot cm^{-2} \cdot pulse^{-1}$.

Employing ultrafast pump-probe spectroscopy in conjunction with homogeneous, chiral, ionic-polymer-wrapped SWNTs, a straightforward method for quantitatively evaluating the extent of optically driven free carrier generation (FCG) in SWNTs can be conducted using the trion transient absorptive hallmark ($Tr^+_{11} \rightarrow Tr^+_{nm}$) and the rapid nature of trion formation dynamics (<1 ps) relative to the established free-carrier decay time scales (>ns) to correlate free-carrier and trion formation dynamics. This can be accomplished because ultrafast formation of the $Tr^{+/-}_{11} \rightarrow Tr^{+/-}_{nm}$ transient absorptive signal in neutral SWNTs derives from the capture of excitons by free carriers. Furthermore, determination of the trion absorption cross section ($\sigma_{Tr}$) associated with the $Tr^{+/-}_{11} \rightarrow Tr^{+/-}_{nm}$ transition manifold can be used to determine the quantum yields of optically driven free carrier formation [$\phi(E_{nn} \rightarrow h^+ + e^-)$] in carbon nanotubes.

Fluence-dependent studies of SWNT FCG underscore that this method for quantifying $\phi(E_{nn} \rightarrow h^+ + e^-)$ maintains utility over excitation conditions that span high to modest pump fluences (e.g., from a few hundreds of $\mu J \cdot cm^{-2} \cdot pulse^{-1}$ to ~15 $\mu J \cdot cm^{-2} \cdot pulse^{-1}$).

Along this line, ultrafast pump-probe studies that examine neutral S-PBN(b)-Ph$_5$-[(6,5) SWNTs] underscore that (i) $\phi(E_{nn} \rightarrow h^+ + e^-)$ varies as a function of exciton energy, with $E_{33}$ excitons driving dramatically enhanced $\phi(E_{nn} \rightarrow h^+ + e^-)$ relative to those derived from $E_{22}$ and $E_{11}$ excitons, and (ii) optically driven FCG quantum yields in SWNTs monotonically increase with increasing solvent dielectric constant due to the progressively reduced exciton binding energy that derives from enhanced medium dielectric screening. SWNT exciton binding energies should vary with the magnitude of the environmental dielectric constants, indicating a potentially powerful means to manage the quantum yields of FCG in SWNTs.

As provided in the sections entitled Experimental Data, the dependence of optically triggered SWNT FCG quantum yields are mapped onto bath dielectric strengths. As these experimental data highlight that the quantum efficiency of intrinsic FCG via exciton dissociation in SWNTs can vary substantially as a function of both exciton energy and the bath dielectric strength, this work provides new insights for engineering SWNT-based compositions for optoelectronic applications, including photodetectors and photovoltaics.

Design, analysis, and layout of carbon nanotube-based devices may be accomplished via graphical computer-aided design (CAD) environments. The physical design stage of an integrated circuit design process generally includes one or more of logic synthesis, floor planning, power planning, placement, clock tree synthesis, routing, verification, and "tapeout" (export of data in form for manufacturing). These stages may be carried out using associated tools that may individually or together form an electronic design automation (EDA) tool. The described modeling of trion behavior and quantifying of optical free-carrier generation in SWNTs can be part of a library and tool that supports schematic and layout entry, rule checking, and netlist generation (logic synthesis stage). The netlist may be generated in, for example, HSpice or VerilogA. In some cases, the netlist may then be used by automatic place and route (APR) software to automate layout of standard cells (placement stage) and then auto-routing of cells (routing stage) based on the connections inferred from the netlist.

Accordingly, a CAD tool or feature can include trion modeling in the form of instructions that can be stored on one or more storage media that when executed by a processor (such as part of a computing device on which the design is being prepared), direct the computing device to implement a one dimensional (1D) kinetic model of trion formation and decay dynamics. In some cases, the four ODEs described above are calculated.

The CAD tool or feature can alternatively or in addition include quantification of free-carrier generation in SWNTs. For example, instructions stored on one or more storage media that when executed by a processor (such as part of a computing device on which the design is being prepared), can direct the computing device to monitor the increase of the $Tr^{+/-}_{11} \rightarrow Tr^{+/-}_{nm}$ transition amplitude as a spectroscopic fingerprint and determine the trion absorption cross section ($\sigma_{Tr}$) associated with the $Tr^{+/-}_{11} \rightarrow Tr^{+/-}_{nm}$ transition manifold to determine the quantum yields of optically driven free carrier formation [$\phi(E_{nn} \rightarrow h^+ + e^-)$] in carbon nanotubes.

Using the described quantification of optically driven free-carrier generation and trion modeling, a system incorporating optoelectronics can be created with one or more devices comprising a single walled carbon nanotube device with trion formation, under stimulation, being controlled by carrier-doping densities. For example, trion formation can be controlled by a hole-polaron or electron-polaron concentration from 6.1 to 14.3 (100 nm)$^{-1}$. In addition, exciton-to-trion conversion can occur via optical, electrical, or magnetic stimuli.

Experimental Data

The following is an example implementation of a method for quantitative evaluation of optical free-carrier generation in semiconducting single-walled carbon nanotubes.

Figure 7A:
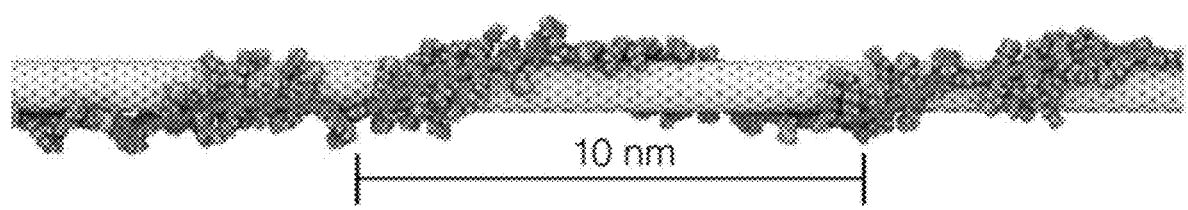
FIGS. 7A and 7B show structures of polymer-wrapped SWNTs.
Figure 7B:
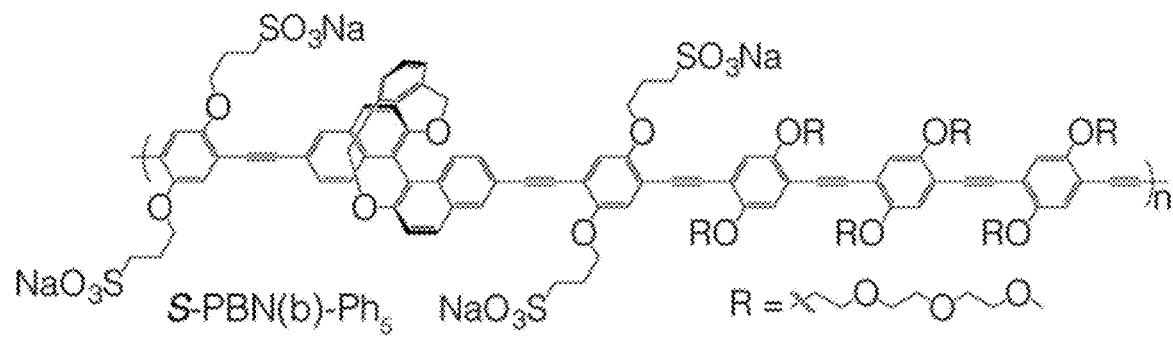

For the first experiments, as a primary task for identifying trion dynamics, SWNTs were acquired having high uniformity of electronic structure (chirality) and length. Dispersion of these SWNTs in the condensed phase by exploiting a binaphthalene-based polyanionic semiconducting polymer [S-PBN(b)-Ph$_5$] that exfoliates, individualizes, and disperses SWNTs via a single-chain helically chiral wrapping mechanism, assures morphological homogeneity of these samples (see FIGS. 7A and 7B, which show structures of polymer-wrapped SWNTs). As can be seen in the structural schematic of a chiral [arylene]ethynylene polymer-wrapped SWNT of FIG. 7A, the polymer wraps the SWNT in an exclusive left-handed helical configuration that features a constant pitch length of 10 nm. The molecular structure of the binaphthalene-based polyanionic semiconducting polymer, S-PBN(b)-Ph$_5$ is shown in FIG. 7B. These semiconducting polymer-SWNT superstructures maintain a fixed polymer helical pitch length on the SWNT surface. The robustness of the polymer-SWNT superstructures in various aqueous and organic solvents enables multiple rigorous separation procedures that permit isolation of highly enriched (purity >90%), length-sorted (700±50 nm) (6,5) SWNTs: these S-PBN(b)-Ph$_5$-[(6,5) SWNTs] thus define uniquely engineered, consistent nanoscale carbon nanotube superstructures with which to probe transient absorptive signatures and dynamics of trions.

1. Preparation and solubilizing polymer-wrapped (6,5) SWNTs in D2O and D2O:MeOH mixtures.

1.1 Preparation of Polymer-Wrapped (6,5) SWNTs.

Approximately 10 mg of nanotubes (Sigma Aldrich 704148-1G Lot #MKBJ6336V) were added to a vial containing 20 ml of aqueous 1.04% (weight/volume) sodium deoxycholate. The vial was bath sonicated for 15 minutes and then tip sonicated for 2 hours (MISONIX, Ultrasonic Liquid Processors, S-4000) at a power level of 12 Watts. The mixture was centrifuged (Optima TLX Ultracentrifuge) at 90,000 grams for 1 hour and the top 80% of the supernatant was collected. (6,5) SWNT purification was performed using an aqueous two-phase extraction (ATPE) method. Briefly, after addition of SWNTs to the ATPE system, (6,5) SWNTs were isolated in a given phase by varying sodium dodecyl sulfate concentration. Once isolated, the layer containing the desired SWNTs was collected, and an equal volume of aqueous 2% (weight/volume) sodium cholate was added. To prepare polymer-wrapped SWNTs, the previous solution was added to an aqueous mixture of the desired polymer dispersant. Surfactant and unbound polymer were removed by exchanging the solution into a buffer solution and subjecting to gel permeation chromatography (this step yielded length-sorted polymer-wrapped (6,5) SWNTs). The resulting sample was desalted via centrifugal filtration. The sample was washed with and then taken up in the desired solvent mixture. This solution was used with no further modifications.

1.2 Solubilizing Polymer-Wrapped (6,5) SWNTs in $D_2O$ and $D_2O$:MeOH Mixtures.

Figure 8:
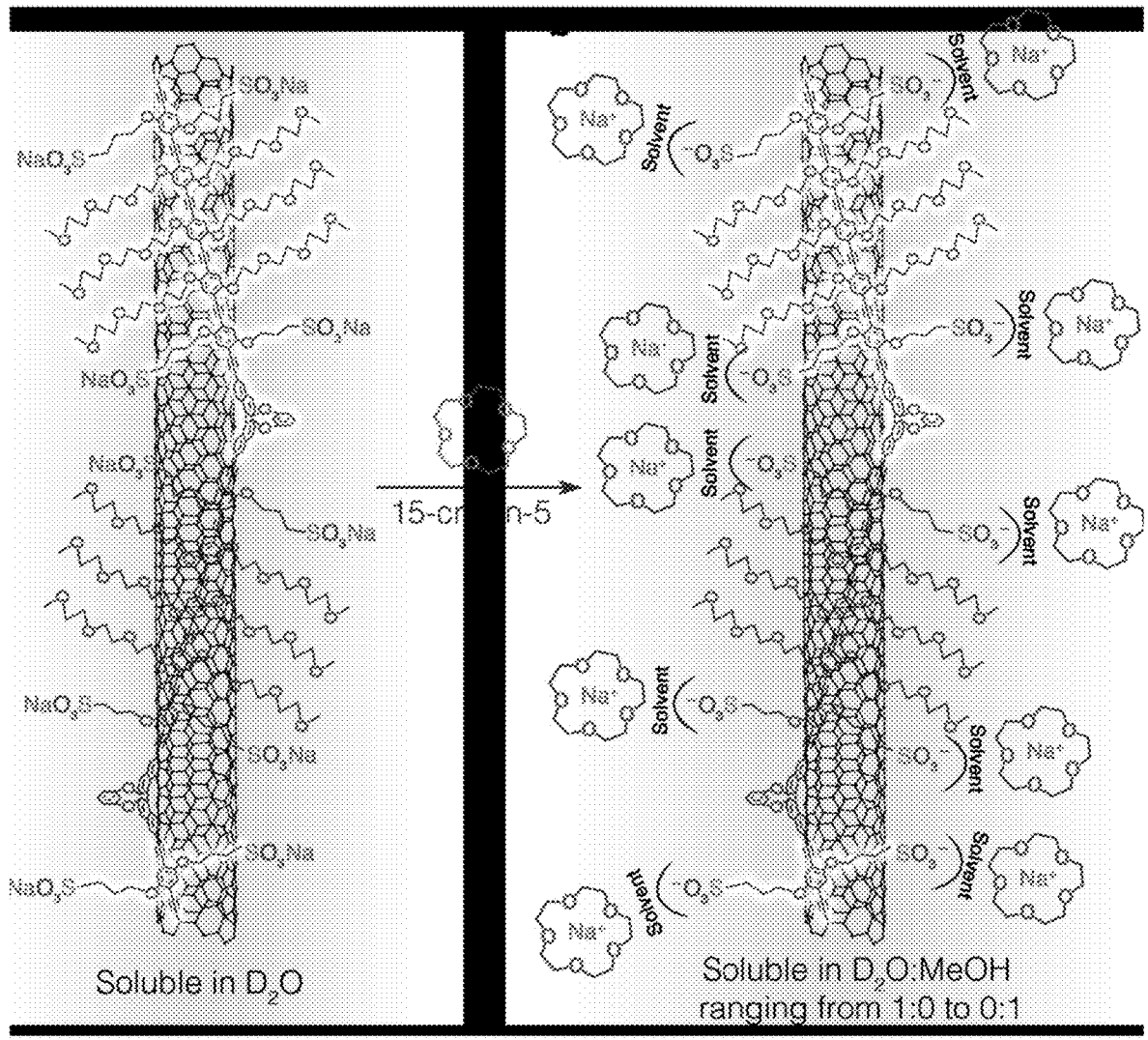
FIG. 8 shows schematic structures of S-PBN(b)-Ph$_5$-[(6, 5) SWNTs] with different countercations.

FIG. 8 shows schematic structures of S-PBN(b)-Ph5-[(6, 5) SWNTs] with different countercations. The left side of the figure shows S-PBN(b)-Ph5-[(6,5) SWNTs] featuring Na+ countercations. The right side of the figure shows S-PBN(b)-Ph5-[(6,5) SWNTs] featuring Na(15-crown-5)+ counter-cations.

Solubilizing S-PBN(b)-Ph5-[(6,5) SWNTs] in $D_2O$: MeOH mixtures (from $D_2O$:MeOH=1:0 to $D_2O$:MeOH=0:1) requires the metathesis of the sodium salt of the chiral, ionic polymer that wraps the SWNT surface. The procedure has been previously described in detail. Briefly, S-PBN(b)-$Ph_5$-[(6,5) SWNTs] was first dissolved in 7:3 $H_2O$:MeOH and the pH was adjusted to ~8 by adding an appropriate amount of 0.1 mM NaOH in $H_2O$. To this solution, an excess amount of 15-crown-5 was added in order to complex the sodium cations, after which the solvent was removed under vacuum. The resulting sticky green solid was then redissolved in the desired $D_2O$:MeOH mixture, and washed 5 times with the same solvent mixture using a Microcon centrifugal YM-100 filter (Milipore, Bedford, Mass.). The structures of S-PBN(b)-$Ph_5$-[(6,5) SWNTs] with $Na^+$ and Na(15-crown-5)$^+$ counterions are schematically highlighted in FIG. 8. Again, S-PBN(b)-$Ph_5$-[(6,5) SWNTs] with $Na^+$ counterions are only soluble in $D_2O$ or in $D_2O$:MeOH mixtures having a high $D_2O$:MeOH ratio. In contrast, S-PBN(b)-$Ph_5$-[(6,5) SWNTs] with Na(15-crown-5)$^+$ counterions manifest consistent solubility in both pure D2O and pure MeOH, as well as other organic solvents.

2. Pump-Probe Spectra of S-PBN(b)-Ph5-[(6,5) SWNTs] with Varying Excitation Energy.

Figure 9A:
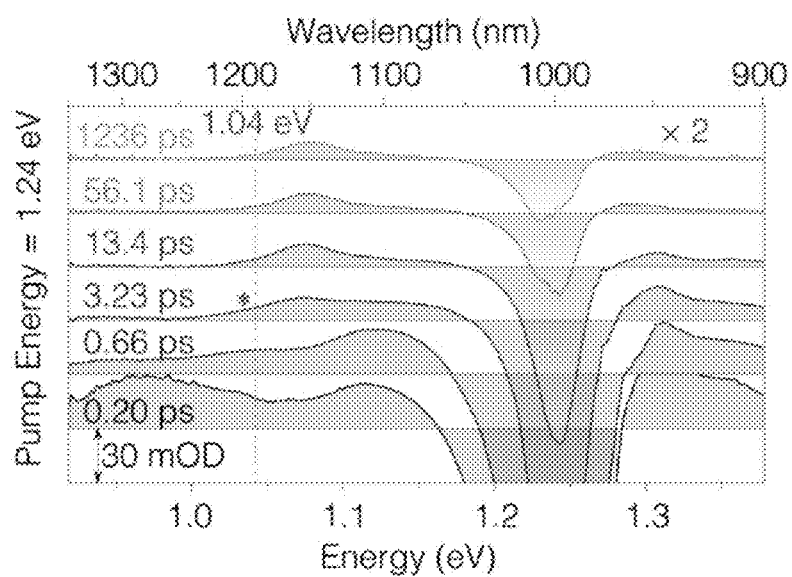
FIGS. 9A-9C show trion signal in transient spectra of neutral polymer-SWNTs.
Figure 9B:
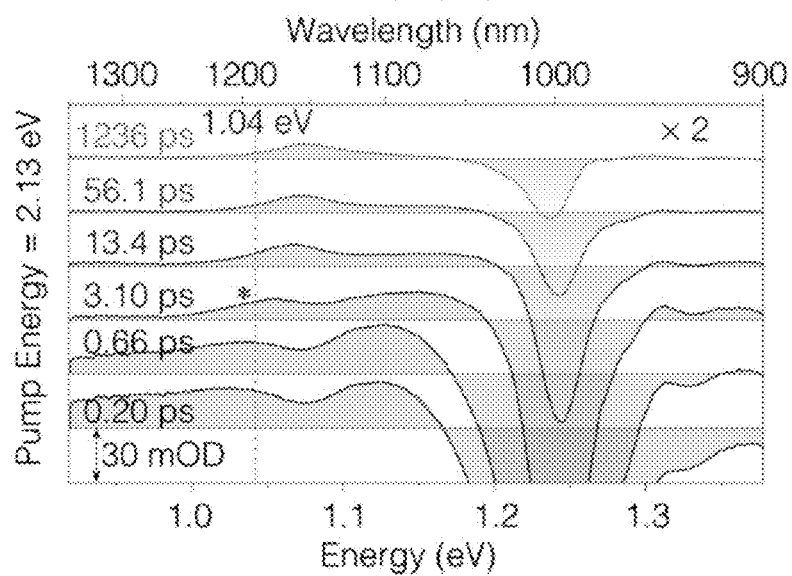
Figure 9C:
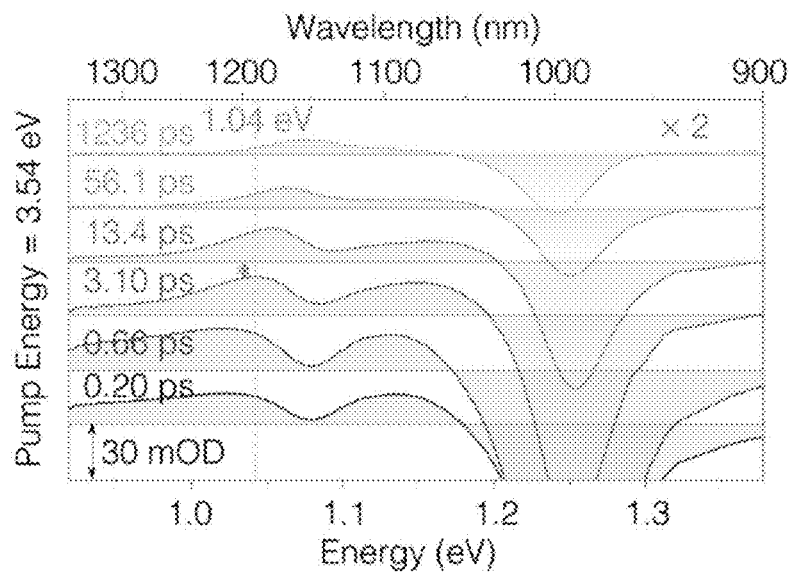

Ultrafast pump-probe transient spectra were acquired for S-PBN(b)-$Ph_5$-[(6,5) SWNTs] with varying optical excitation energies: 1.24 eV ($E_{00} \rightarrow E_{11}$ transition), 2.13 eV ($E_{00} \rightarrow E_{22}$ transition) and 3.54 eV ($E_{00} \rightarrow E_{33}$ transition). FIGS. 9A-9C show trion signal in transient spectra of neutral polymer-SWNTs. FIG. 9A shows pump-probe spectra of neutral S-PBN(b)-Ph5-[(6,5) SWNTs] following $E_{00} \rightarrow E_{11}$ excitation (hvpump~1.24 eV), pump power=180 nJ/pulse. FIG. 9B shows pump-probe spectra of neutral S-PBN(b)-Ph5-[(6,5) SWNTs] following $E_{00} \rightarrow E_{22}$ excitation (hvpump~2.13 eV), pump power=310 nJ/Pulse. FIG. 9C shows pump-probe spectra of neutral S-PBN(b)-Ph5-[(6,5) SWNTs] following $E_{00} \rightarrow E_{33}$ excitation (hvpump~3.54 eV), pump power=500 nJ/pulse. General experimental conditions: ambient temperature (~293 K), magic angle polarization, solvent=D2O.

As can be seen from FIGS. 9A-9C, the transient absorptive signal at ~1.04 eV becomes increasingly dramatic with increasing photon excitation energy. This transient absorptive signal, as discussed in the main text, corresponds to the trion fingerprint evinced in the transient absorption spectra of hole-doped (6,5) SWNT, thus denotes the formation of trions in neutral (6,5) SWNT following optical excitation.

3. Evaluating the Conversion Efficiency of Optically-Generated Free Carriers to Trions.

Quantitatively correlating trion signal intensity to the quantum yield of optically-generated free carriers in neutral SWNTs is based on the supposition that free carriers are essentially converted completely into trions within a few picoseconds ("ps"), so that the maximal trion yield ($N_{Tr+/-11,max}$) corresponds to the amount of optically-generated free carriers ($N_{h+,max} + N_{e-,max}$). Such a supposition was experimentally verified by analyzing the trion formation dynamics and the deconvoluted pump-probe spectra in the NIR regime.

First, by analyzing trion formation dynamics, the time window wherein the amount of trions reaches a maximum in neutral SWNTs following optical excitation was determined.

FIGS. 10A-10F show trion formation dynamics and spectral deconvolution of pump-probe spectra in the NIR regime for neutral S-PBN(b)-Ph5-[(6,5) SWNTs]. FIG. 10A shows trion formation dynamics characterized by the changes of oscillator strength corresponding to the $Tr^+_{11} \rightarrow Tr^+_{nm}$ transition (acquired following optical excitation at 1.24 eV; $E_{00} \rightarrow E_{11}$ excitation). FIG. 10B shows trion formation dynamics similar to FIG. 10A except for excitation energy (hvpump=2.13 eV; $E_{00} \rightarrow E_{22}$ excitation). FIG. 10C shows trion formation dynamics similar to FIG. 10A except for excitation energy (hvpump=3.54 eV; $E_{00} \rightarrow E_{33}$ excitation). FIG. 10D shows Gaussian deconvolution of pump-probe spectra at tdelay~1.1 ps, hvpump=1.24 eV. FIG. 10E shows Gaussian deconvolution of pump-probe spectra at tdelay~1.2 ps, hvpump=2.13 eV. FIG. 10F shows Gaussian deconvolution of pump-probe spectra at tdelay~2.0 ps, hvpump=3.54 eV.

Trion formation dynamics are characterized by the changes of oscillator strength corresponding to the $Tr^{+/-}_{11} \rightarrow Tr^{+/-}_{nm}$ transition (shown in FIGS. 10A-10C). As can be seen in Fig. FIGS. 10A-10C, following $E_{00} \rightarrow E_{nn}$ (where n=1, 2 or 3) excitation, $Tr^{+/-}_{11} \rightarrow Tr^{+/-}_{nm}$ signal intensities reach a maximum at a delay time ($t_{delay}$) of ~1-2 ps. The transient spectra at the delay time was selected where $Tr^{+/-}_{11} \rightarrow Tr^{+/-}_{nm}$ signal intensities reach maximum based the kinetic traces in FIGS. 10A-10C, following the corresponding deconvoluted spectra to evaluate the conversion efficiency from free carriers to trions was further examined. For example, following $E_{00} \rightarrow E_{11}$ excitation, the deconvoluted transient spectrum at $t_{delay}$~1.1 ps manifests four components (shown in FIG. 10D): (i) a broad fast-decay NIR transient absorption band (~0.92-1.02 eV; $\tau_{decay}$~0.7 ps), (ii) $Tr^{+/-}_{11} \rightarrow Tr^{+/-}_{nm}$ transition centered at ~1.04 eV, (iii) a transient absorption manifold centered at ~1.08 eV characteristic of both $^3E_{11} \rightarrow {}^3E_{nn}$ and hole/electron polaron absorptions, and (iv) $E_{11} \rightarrow E_{11,BX}$ transition centered at ~1.13 eV.

Among these components, the integrated oscillator strength of the transient absorption manifold centered at ~1.08 eV was close to zero. Similarly, FIGS. 10E and 10F show that when $Tr^{+/-}_{11} \rightarrow Tr^{+/-}_{nm}$ signal reaches the highest intensity, the oscillator strengths of the transient absorption manifold centered at ~1.08 eV are close to zero. Again, as hole/electron polarons in (6,5) SWNTs absorb at ~1.08 eV, the negligible signal intensity at ~1.08 eV that was manifested concomitantly with the highest $Tr^{+/-}_{11} \rightarrow Tr^{+/-}_{nm}$ signal intensity directly suggested a near-unit conversion efficiency of optically-generated free carriers to trions.

4. Determining the Absorption Cross Section ($\sigma_{Tr}$) for Trions in (6,5) SWNTs.

FIG. 11 shows a plot of exciton density ($NE_{11}$) vs. hole-doping density ($Nh+$) for S-PBN(b)-Ph5-[(6,5) SWNTs]. $NE_{11}$ and $Nh^+$ were determined following previously established protocols. Excitation conditions: hvpump=1.24 eV, pump power~170 nJ/pulse, ambient temperature (293K). Note that constant hvpump and pump power were used for S-PBN(b)-Ph5-[(6,5) SWNT] excitation as hole-doping density was varied; in this regard, note that the variation of SWNT exciton densities mainly derive from the decrease of the $E_{00} \rightarrow E_{11}$ transition oscillator strength with increasing hole-doping densities.

The $\sigma_{Tr}$ (associated with $Tr^+_{11} \rightarrow Tr^+_{nm}$ transition per trion quasiparticle) was determined relying on the spectroscopic properties established for hole-doped (6,5) SWNTs. As $\sigma_{Tr} = A/(l \times C_{SWNT} \times N_A \times L_{SWNT} \times N_{Tr+11})$, where A is the maximum absorbance corresponding to the $Tr^+_{11} \rightarrow Tr^+_{nm}$ transition at ~1.04 eV for (6,5) SWNTs, l is the optical path length of the spectral cuvette, $C_{SWNT}$ is the SWNT molar concentration, $N_A$ is Avogadro constant, $L_{SWNT}$ is the average SWNT length (~700 nm), and $N_{Tr+11}$ is the trion quasiparticle density per 100 nm within the (6,5) SWNT. A relatively accurate A can be acquired via spectral deconvolution of the NIR pump-probe spectrum wherein $Tr^+_{11} \rightarrow Tr^+_{nm}$ transition occurs (vide infra), while $C_{SWNT}$ can be determined following previously established protocols. Trion densities (i.e. $N_{Tr+11}$) were first determined in optically-excited, hole-doped (6,5) SWNTs. Note that previous investigations of hole-doped (6,5) SWNTs have established that under certain hole-doping densities ($N_{h+}$), exciton-to-trion conversion yield can approach unity. Under such doping conditions, trion density is essentially equal to the density of optically produced excitons. For instance, in (6,5) SWNTs, where $N_{h+}$ is fixed at ~14.3 (100 nm)$^{-1}$, exciton-to-trion conversion yield is ~1, while the corresponding exciton density $N_{E11}$ is determined to be ~0.6 (100 nm)$^{-1}$ (see FIG. P1S4, which plots $N_{E11}$ vs. $N_{h+}$) has been demonstrated. Thus, the maximum trion density ($N_{Tr+11}$) under the excitation condition highlighted in FIG. 11 (see arrow to data point) is ~0.6 (100 nm)$^{-1}$.

A, the maximum absorbance of the $Tr^+_{11} \rightarrow Tr^+_{nm}$ transition, was determined next. FIG. 12 shows a kinetic trace representing trion formation dynamics in hole-doped S-PBN(b)-Ph5-[(6,5) SWNTs].

By analyzing trion formation dynamics in hole-doped SWNTs ($N_{h+}$~14.3 (100 nm)$^{-1}$), the time window wherein trion density reaches a maximum following $E_{00} \rightarrow E_{11}$ optical excitation was determined. Such a dynamic process has been established previously, and is displayed in FIG. 12 (more details regarding the acquisition of this kinetic trace may be found in previous work). As can be seen in FIG. 12, $N_{Tr+11}$ reaches the maximum value in the time window of ~0.7-1 ps; accordingly, the NIR transient spectrum recorded at $t_{delay}$~0.9 ps was selected, and a Gaussian function deconvolution was carried out.

FIG. 13 shows a deconvoluted pump-probe transient spectrum at tdelay~0.9 ps for hole-doped S-PBN(b)-Ph5-[(6,5) SWNTs]. The absorbance contribution at 1.04 eV from the $Tr^+_{11} \rightarrow Tr^+_{nm}$ transition (orange) is determined as ~7.66 mOD. The deconvoluted components are highlighted in FIG. 13, among which the absorbance of $Tr^+_{11} \rightarrow Tr^+_{nm}$ transition is readily seen (A~7.66 mOD). Knowing A, $C_{SWNT}$, l, $N_A$, $L_{SWNT}$, and $N_{Tr+11}$, $\sigma_{Tr}$ was calculated to be ~2.16×10$^{-16}$ cm$^2$/trion.

5. Spectral Deconvolution of the SWNT Linear Absorption Spectrum.

FIG. 14 shows a deconvolution of a linear absorption spectrum of SWNTs. The linear absorption spectrum of purified, neutral S-PBN(b)-Ph5-[(6,5) SWNTs] was acquired over the UV-vis-NIR spectral domain. Gaussian peak analysis was exploited to acquire the peak information for (6,5) SWNT $E_{00} \rightarrow E_{11}$, $E_{00} \rightarrow E_{22}$ and $E_{00} \rightarrow E_{33}$ optical transitions. Experimental conditions: solvent=D2O, T=293K.

The comprehensive methodology for fitting SWNT absorption spectra has been detailed in previous investigations. Following the established procedure to perform the spectral fitting, which yields the deconvoluted spectra as shown in FIG. 14; $E_{00} \rightarrow E_{11}$, $E_{00} \rightarrow E_{22}$, and $E_{00} \rightarrow E_{33}$ optical transitions for (6,5) SWNTs are highlighted as point 1, point 10, and point 15.

6. Pump-Probe Spectra of (6,5) SWNTs Dispersed by Different Surfactants.

FIGS. 15A and 15B show trion signal in transient (pump-probe) spectra of neutral polymer-SWNTs and SC-SWNTs, respectively. FIG. 15A shows the pump-probe spectra recorded for neutral S-PBN(b)-Ph5-[(6,5) SWNTs]; and FIG. 15B shows the pump-probe spectra recorded for neutral SC-[(6,5) SWNTs]. General experimental conditions: $E_{00} \rightarrow E_{33}$ optical excitation (hvpump~3.54 eV), pump power~500 nJ/pulse, ambient temperature (~293K), magic angle polarization, solvent=D$_2$O.

The pump-probe spectra of S-PBN(b)-Ph$_5$-[(6,5) SWNTs] were compared with that of SC-[(6,5) SWNTs] (i.e. sodium cholate dispersed (6,5) SWNTs). A distinct difference between these two sets of transient spectra is that the trion transient absorptive signal is much more dramatic in the spectra of S-PBN(b)-Ph$_5$-[(6,5) SWNT] sample than that in the spectrum recorded SC-[(6,5) SWNTs]. Note that in the pump-probe spectra of FIGS. 15A and 15B, the signal labeled at ~1.04 eV (*) denotes the trion transient absorption hallmark ($Tr^{+\backslash-}_{11} \rightarrow Tr^{+\backslash-}_{nm}$ transition) and is highlighted in the spectra by dash lines. Further note that the excitation conditions for these two samples are identical (excitation energy, pump power, solvent), and similar SWNT molar concentrations are utilized (indicated by the optical density at 1.24 eV, i.e. $E_{00} \rightarrow E_{11}$ transition energy for the two samples). Again, as pointed out in the main text, the combination of identical excitation conditions coupled with a substantially stronger $Tr^{+\backslash-}_{11} \rightarrow Tr^{+\backslash-}_{nm}$ transition signal intensity in transient spectra recorded for the S-PBN(b)-Ph$_5$-[(6,5) SWNTs] sample, which directly points to the different natures of S-PBN(b)-Ph$_5$-[(6,5) SWNT] and SC-[(6,5) SWNT] nanotube surfaces: the SWNT surface is considerably more exposed to the surrounding dielectric medium in S-PBN(b)-Ph$_5$-[(6,5) SWNTs], while more isolated in SC-[(6,5) SWNTs], causing optically-driven free-carrier generation to be greatly suppressed in SC-[(6,5) SWNTs], and resulting in a minimal trion formation under these conditions.

7. Pump Fluence Dependence Studies.

This method for quantifying FCG quantum yields in SWNTs and is valid when trions form with near-unit efficiency, so that the free-carrier densities can be directly correlated with trion densities. As such, this method will be suitable for a specific range of pump fluences, as when the pump fluence becomes so low that the inter-exciton distance is much longer than the exciton diffusion length, trions will not form with near-unit efficiency. The regime where trions can form with near-unit efficiency via a series of fluence-dependent measurements was experimentally determined. In these studies, fluence-dependent studies for $E_{00} \rightarrow E_{11}$, $E_{00} \rightarrow E_{22}$, and $E_{00} \rightarrow E_{33}$ excitation, a (ii) examine a broad range of pump fluences for all these excitation energies, so that the converted exciton densities ranges from >20 to <1 per nanotube (~700 nm in length) were performed.

FIGS. 16A-16F show fluence-dependent transient absorption spectra with $E_{00} \rightarrow E_{11}$ optical excitation from pump-probe spectra recorded for neutral S-PBN(b)-Ph5-[(6,5) SWNTs] with a broad range of pump fluences: FIG. 16A: 198 $\mu J \cdot cm^{-2} \cdot pulse^{-1}$; FIG. 16B: 61.7 $\mu J \cdot cm^{-2} \cdot pulse^{-1}$; FIG. 16C: 14.1 $\mu J \cdot cm^{-2} \cdot pulse^{-1}$; FIG. 16D 3.53 $\mu J \cdot cm^{-2} \cdot pulse^{-1}$; FIG. 16E: 0.88 $\mu J \cdot cm^{-2} \cdot pulse^{-1}$; FIG. 16F: 0.18 $\mu J \cdot cm^{-2} \cdot pulse^{-1}$. Note that the signal labeled at ~1.04 eV (*) denotes the trion transient absorption hallmark ($Tr^{+\backslash -}_{11} \rightarrow Tr^{+\backslash -}_{nm}$ transition) and is highlighted in the spectra by dash lines. General experimental conditions: $E_{00} \rightarrow E_{11}$ optical excitation (hvpump~1.24 eV), ambient temperature (~293K), magic angle polarization, solvent=D2O.

FIGS. 17A-17F show fluence-dependent transient absorption spectra with $E_{00} \rightarrow E_{22}$ optical excitation from pump-probe spectra recorded for neutral S-PBN(b)-Ph5-[(6,5) SWNTs] with a broad range of pump fluences: FIG. 17A: 341 $\mu J \cdot cm^{-2} \cdot pulse^{-1}$; FIG. 17B: 53.8 $\mu J \cdot cm^{-2} \cdot pulse^{-1}$; FIG. 17C: 14.1 $\mu J \cdot cm^{-2} \cdot pulse^{-1}$; FIG. 17D: 5.29 $\mu J \cdot cm^{-2} \cdot pulse^{-1}$; FIG. 17E: 1.76 $\mu J \cdot cm^{-2} \cdot pulse^{-1}$; FIG. 17F: 0.35 $\mu J \cdot cm^{-2} \cdot pulse^{-1}$. Note that the signal labeled at ~1.04 eV (*) denotes the trion transient absorption hallmark ($Tr^{+\backslash -}_{11} \rightarrow Tr^{+\backslash -}_{nm}$ transition) and is highlighted in the spectra by dash lines. General experimental conditions: $E_{00} \rightarrow E_{22}$ optical excitation (hvpump~2.13 eV), ambient temperature (~293K), magic angle polarization, solvent=D2O.

FIGS. 18A-18E show fluence-dependent transient absorption spectra with $E_{00} \rightarrow E_{33}$ optical excitation from pump-probe spectra recorded for neutral S-PBN(b)-Ph5-[(6,5) SWNTs] with a broad range of pump fluences: FIG. 18A 244 $\mu J \cdot cm^{-2} \cdot pulse^{-1}$; FIG. 18B: 61.7 $\mu J \cdot cm^{-2} \cdot pulse^{-1}$; FIG. 18C: 20.3 $\mu J \cdot cm^{-2} \cdot pulse^{-1}$; FIG. 18D: 10.2 $\mu J \cdot cm^{-2} \cdot pulse^{-1}$; FIG. 18E: 1.76 $\mu J \cdot cm^{-2} \cdot pulse^{-1}$. Note that the signal labeled at ~1.04 eV (*) denotes the trion transient absorption hallmark ($Tr^{+\backslash -}_{11} \rightarrow Tr^{+\backslash -}_{nm}$ transition) and is highlighted in the spectra by dash lines. General experimental conditions: $E_{00} \rightarrow E_{33}$ optical excitation (hvpump~3.54 eV), ambient temperature (~293K), magic angle polarization, solvent=D2O.

These excitation energy- and fluence-dependence experiments enable the clear determination of the transitions points (i.e. the fluences) at which the trion transient absorption signal begins to disappear. These observations demarcate the fluence regime where trions can form with near-unit efficiency, i.e. the regime where this method determines optically-driven FCG quantum yields in semiconducting SWNTs. The fluence-dependent pump-probe transient absorption spectra at selected delay times have been plotted and shown in FIGS. 16A-18E, while the corresponding excitation conditions (i.e. pump fluences and exciton densities) have been summarized in the below three Tables.

TABLE S1

$E_{00} \rightarrow E_{11}$ optical pump fluences and calculated exciton densities.

| Beam diameter ($\mu m$) | Power ($nJ \cdot pulse^{-1}$) | Power density ($\mu J \cdot cm^{-2} \cdot pulse^{-1}$) | Photons (photons $\cdot pulse^{-1}$) | Photon density (photons $\cdot cm^{-2} \cdot pulse^{-1}$) | Exciton density (excitons $\cdot (100\ nm)^{-1}$) |
|---|---|---|---|---|---|
| 340 | 180 | 198 | $9.06 \times 10^{11}$ | $9.98 \times 10^{14}$ | 6.8 |
| 850 | 350 | 61.7 | $1.76 \times 10^{10}$ | $3.11 \times 10^{14}$ | 3.9 |
| 850 | 80 | 14.1 | $4.03 \times 10^{11}$ | $7.10 \times 10^{13}$ | 2.6 |
| 850 | 20 | 3.53 | $1.01 \times 10^{11}$ | $1.78 \times 10^{13}$ | 1.4 |
| 850 | 5 | 0.88 | $2.52 \times 10^{10}$ | $4.44 \times 10^{12}$ | 0.4 |
| 850 | ~1 | 0.18 | $5.03 \times 10^{9}$ | $8.88 \times 10^{12}$ | ~0.1 |

TABLE S2

$E_{00} \rightarrow E_{22}$ optical pump fluences and calculated exciton densities.

| Beam diameter ($\mu m$) | Power ($nJ \cdot pulse^{-1}$) | Power density ($\mu J \cdot cm^{-2} \cdot pulse^{-1}$) | Photons (photons $\cdot pulse^{-1}$) | Photon density (photons $\cdot cm^{-2} \cdot pulse^{-1}$) | Exciton density (excitons $\cdot (100\ nm)^{-1}$) |
|---|---|---|---|---|---|
| 340 | 310 | 341 | $9.05 \times 10^{11}$ | $9.97 \times 10^{14}$ | 6.1 |
| 850 | 305 | 53.8 | $8.91 \times 10^{11}$ | $1.57 \times 10^{14}$ | 3.7 |
| 850 | 80 | 14.1 | $2.34 \times 10^{11}$ | $4.12 \times 10^{13}$ | 2.2 |
| 850 | 30 | 5.29 | $8.76 \times 10^{10}$ | $1.54 \times 10^{13}$ | 1.7 |
| 850 | 10 | 1.76 | $2.92 \times 10^{10}$ | $5.15 \times 10^{12}$ | 0.5 |
| 850 | ~2 | 0.35 | $5.84 \times 10^{9}$ | $1.03 \times 10^{12}$ | ~0.1 |

TABLE S3

$E_{00} \rightarrow E_{11}$ optical pump fluences and calculated exciton densities.

| Beam diameter (μm) | Power (nJ · pulse$^{-1}$) | Power density (μJ · cm$^{-2}$ · pulse$^{-1}$) | Photons (photons · pulse$^{-1}$) | Photon density (photons · cm$^{-2}$ · pulse$^{-1}$) | Exciton density (excitons · (100 nm)$^{-1}$) |
|---|---|---|---|---|---|
| 510 | 500 | 244 | 8.81 × 10$^{11}$ | 4.31 × 10$^{14}$ | 4.1 |
| 850 | 350 | 61.7 | 6.17 × 10$^{11}$ | 1.09 × 10$^{14}$ | 2.8 |
| 850 | 115 | 20.3 | 2.03 × 10$^{11}$ | 3.57 × 10$^{13}$ | 1.1 |
| 850 | 58 | 10.2 | 1.02 × 10$^{11}$ | 1.80 × 10$^{13}$ | 0.5 |
| 850 | 10 | 1.76 | 1.76 × 10$^{10}$ | 3.11 × 10$^{12}$ | ~0.1 |

7.2 Evaluating the Conversion Efficiency of Optically-Generated Free Carriers to Trions at Modest Pump Fluences.

FIGS. 19A-19C show spectral deconvolution of pump-probe spectra in the NIR regime for neutral SPBN(b)-Ph5-[(6,5) SWNTs]. FIG. 19A shows Gaussian deconvolution of pump-probe spectra at tdelay~1.3 ps, hvpump=1.24 eV. FIG. 19B shows Gaussian deconvolution of pump-probe spectra at tdelay~1.1 ps, hvpump=2.13 eV. FIG. 19C shows Gaussian deconvolution of pump-probe spectra at tdelay~1.9 ps, hvpump=3.54 eV.

From the above fluence-dependent measurements, the pump fluence regime where the trion transient absorption signal begins to disappear was identified. To examine whether or not trions could form with near-unit efficiency above such critical pump fluence values, the strategy detailed in Section 3 was exploited. Briefly, the transient spectra at the delay time was selected where $Tr^{+/-}{}_{11} \rightarrow Tr^{+/-}{}_{nm}$ signal intensities reach a maximum, following which the corresponding deconvoluted spectra to evaluate the conversion efficiency from free carriers to trions was examined. Following $E_{00} \rightarrow E_{nn}$ excitation (where n=1, 2, or 3), the deconvoluted transient spectrum at the selected delay time manifests four components (shown in FIGS. 19A-19C: (i) a broad fast-decay NIR transient absorption band (~0.92-1.02 eV; $\tau_{decay}$~0.7 ps), (ii) $Tr^{+/-}{}_{11} \rightarrow Tr^{+/-}{}_{nm}$ transition centered at ~1.04 eV, (iii) a transient absorption manifold centered at ~1.08 eV characteristic of both $^3E_{11} \rightarrow {}^3E_{nn}$ and hole/electron polaron absorptions, and (iv) $E_{11} \rightarrow E_{11,BX}$ transition centered at ~1.13 eV. Among these components, the $Tr^{+/-}{}_{11} \rightarrow Tr^{+/-}{}_{nm}$ signal reaches the highest intensity, while the oscillator strengths of the transient absorption manifold centered at ~1.08 eV are close to zero. Again, as hole/electron polarons in (6,5) SWNTs absorb at ~1.08 eV, the negligible signal intensity at ~1.08 eV that is manifested concomitantly with the highest $Tr^{+/-}{}_{11} \rightarrow Tr^{+/-}{}_{nm}$ signal intensity signals the near-unit conversion efficiency of optically-generated free carriers to trions. As such, the fluence regime where trions form with near-unit efficiency (from hundreds of μJ·cm$^{-2}$·pulse$^{-1}$ to ~15 μJ·cm$^{-2}$·pulse$^{-1}$) was identified: this fluence regime defines the range where this methodology can be applied to quantify FCG in SWNT.

FIG. 20 shows a plot of excitation-energy- and fluence-dependent FCG quantum yields. Quantum yields of optically-driven FCG as a function of both excitation energy and the pump fluences; error bars represent the uncertainty that derives from the spectral fitting procedure used to determine the absorbance A and the trion absorption cross section σTr associated with the $Tr^{+/-}{}_{11} \rightarrow Tr^{+/-}{}_{nm}$ transition.

The following is an example method implementation of dynamics of charged excitons in electronically and morphologically homogeneous single-walled carbon nanotubes.

1. Preparation of polymer-wrapped (6,5) SWNTs and morphological characterization.

The as-prepared polymer-SWNTs were characterized by atomic force microscopy (AFM), and the corresponding topographic intermittent contact AFM image associated with height profiles are provided in FIGS. 21A-21C. In particular, FIGS. 21A-21C show AFM characterization of S-PBN(b)-Ph5-[(6,5) SWNT] samples. FIG. 21A is a topographic intermittent contact AFM image of S-PBN(b)-Ph5-[(6,5) SWNT] from an aqueous suspension on a Si surface. FIG. 21B shows a height profile along the x direction of FIG. 21A; and FIG. 21C shows a height profile along the z direction (out of page) of FIG. 21A.

AFM images of S-PBN(b)-Ph$_5$-[(6,5) SWNT] dispersed in aqueous solvent corroborate the well-defined periodicities with constant pitch length of ~10 nm (see distance between two dash lines in FIG. 21B). Also, the polymer-wrapped SWNTs are well individualized, as highlighted in FIG. 21C.

2. Determination of Hole Polaron and Exciton Densities in SWNT.

2.a. Determination of Hole Polaron Densities.

The protocol for rigorously controlling hole polaron densities in SWNT has been explicitly described in Deria P, Olivier J-H, Park J, Therien M J (2014) Potentiometric, Electronic, and Transient Absorptive Spectroscopic Properties of Oxidized Single-Walled Carbon Nanotubes Helically Wrapped by Ionic, Semiconducting Polymers in Aqueous and Organic Media. *J Am Chem Soc* 136(40):14193-14199. In brief, (i) SWNTs having uniform length (l=700±50 nm) distribution were obtained by gel permission chromatography (GPC) separation; (ii) the mass concentration (ρ) of SWNTs can be determined using the value from Zheng et al., which correlated OD=1 in 1 cm beam path length at $E_{00} \rightarrow E_{11}$ transition to 6.5 μg mL$^{-1}$ of (6,5) tubes; (iii) the molar concentration of the oxidant was experimentally determined. As the SWNT length is known, the "molecular weight" of these SWNTs, M (g mol$^{-1}$) can be estimated. Then, the molar concentration of SWNTs was calculated by [SWNTs]=ρ×10$^{-3}$/M (for oxidative titration experiments, [SWNTs]~72 nM). With known molar centration of the oxidant [K$_2$IrCl$_6$] and [SWNTs], and the SWNT length, the hole polaron densities can be calculated by [h$^+$]=([K$_2$IrCl$_6$]× V$_1$/([SWNTs]×V$_2$))/l, where V$_1$ and V$_2$ are the volume of the titrant and SWNTs solution sample, respectively.

2.b. Determination of Exciton Densities.

The protocol for rigorously controlling exciton densities in SWNTs has been described previously. Generally, from the measurement of excitation power, the number of incident photons (P$_I$) was calculated. 2) From the measurement of the transmitted excitation power of the SWNT solution and a blank solvent, the numbers of photons absorbed by the SWNTs (P$_A$) and solvent (P$_{Sol}$), as well as the number of photons scattered by the cuvette (P$_{Sc}$), were obtained using P$_A$=P$_I$–P$_{Sc}$–P$_{Sol}$–P$_T$, where P$_{Sc}$: the number of scattered photons, P$_{Sol}$: the number of photons absorbed by solvent, P$_T$: the number of transmitted photons, P$_A$: the number of absorbed photons. 3) From the linear absorbance of the SWNT solution, the SWNT concentration was determined. 4) From the beam diameter measurement, the illuminated volume (V) was obtained. 5) From the SWNT concentration and V, the number of SWNTs in the given V was obtained. 6) From the computed number of absorbed photons and the number of SWNTs in V, the number of excitons generated per 100 nm of SWNT unit length was calculated. It is noted that, for SWNTs samples having different [h$^+$], the exciton densities are varying as a function of [h$^+$], even though identical excitation conditions are applied throughout the measurements for all the hole-doped SWNTs samples; this phenomenon is due to phase space filling.

3. Model Description and Data Fitting.

3.a. Further Description of the Kinetic Model and Rate Equations.

The kinetic model is derived based on 1D diffusion mechanism, where exciton-exciton and exciton-hole interactions are both considered. The simplified exciton-exciton annihilation (EEA) model described by Lüer and co-workers has been adapted and was derived based on pure one-dimensional diffusion and by assuming immediate annihilation upon contact. In addition to the assumptions that have been justified in the main text for this adapted model, there are two additional notes here: (i) in the differential equations describing the decay rate of excitonic species, dissociation of a trion into one $E_{11}$ exciton and one h$^+$ was initially considered by involving a term of $k_{Tr-E}N_{Tr11}{}^+$, where $k_{Tr-E}$ represents the first-order trion dissociation rate constant (See below equation (1)-(4) for the corresponding changes); however, fitting kinetic data ($E_{11}$ exciton decay traces and hole trion evolution and decay traces acquired with differing [h$^+$] but identical excitation conditions) using such a model consistently gives rise to $k_{Tr-E}$ ranging from 10 to $10^3$ s$^{-1}$, that is negligible relative to other dynamical processes. In this regard, such a term ($k_{Tr-E}N_{Tr11}{}^+$) can be removed from the rate equations. (ii) In the present rate equations, the intrinsic decay of singlet exciton is expressed as a term of $-k_{10}N_{E11}$ ($k_{10} \sim 0.048$ ps$^{-1}$), contrasting to some previously used treatment, where singlet exciton decay was expressed as dispersive first-order decay.

FIGS. 22A and 22B show $E_{11}$ exciton dynamics in neutral S-PBN(b)-Ph5-[(6,5) SWNT]. FIG. 22A shows excitation fluence-dependence of $E_{00} \rightarrow E_{11}$ bleaching signal intensity at 1010 nm. FIG. 22B shows $E_{00} \rightarrow E_{11}$ bleach kinetics (same data as that displayed in a) normalized at tdelay=3 ps, and the exponential function fitting of the kinetic traces (fitting range: 3-2500 ps). Experimental conditions: solvent=D2O, T=293 K, magic angle polarization, λPump=1000 nm, pump fluence=6.4 µJ·cm$^{-2}$, 24.0 µJ·cm$^{-2}$, 80.0 µJ·cm$^{-2}$, 288.0 µJ·cm$^{-2}$.

Pump fluence-dependent measurements have been carried out here ($\lambda_{Pump}$=1000 nm), and the kinetic traces ($\lambda_{Probe}$=1010 nm) are compared in FIG. 22A. FIG. 22B displays the corresponding kinetic data normalized at $t_{delay}$=3 ps. As can be seen in FIG. 22B, variation of the pump fluence from 6.4 µJ·cm$^{-2}$ to 228 µJ·cm$^{-2}$ induces no observable changes to the kinetics in the longer delay range ($t_{delay}$>3 ps), and these kinetic traces beyond $t_{delay}$=3 ps can be fitted consistently using exponential functions, resulting in an averaged lifetime of ~20.7 ps, congruent with data obtained from photoluminescence measurements. As such, in the present kinetic model, the intrinsic decay of singlet excitons was described as a first-order process with a rate constant of $k_{10}$~0.048 ps$^{-1}$, based on the data from pump-probe measurements with the S-PBN(b)-Ph$_5$-[(6,5) SWNT] samples. In summary, rate equations describing dynamics of $E_{11}$ excitons, trions, and hole polarons can be derived as following:

$$\frac{dN_{E_{11}}}{dt} = -k_{10}N_{E_{11}} - k_{EEA}(t-t_0)^{-\frac{1}{2}}N_{E_{11}}^2 + \quad (1)$$
$$k_{21}N_{E_{11,2}} - k_{E-Tr}(t-t_0)^{-\frac{1}{2}}N_h + N_{E_{11}}.$$

$$\frac{dN_{E_{11,2}}}{dt} = \frac{1}{2}k_{EEA}(t-t_0)^{-\frac{1}{2}}N_{E_{11}}^2 - k_{21}N_{E_{11,2}} \quad (2)$$

$$\frac{dN_{Tr_{11}^+}}{dt} = k_{E-Tr}(t-t_0)^{-\frac{1}{2}}N_h + N_{E_{11}} - k_{Tr}N_{Tr_{11}^+} \quad (3)$$

$$\frac{dN_h^+}{dt} = -k_{E-Tr}(t-t_0)^{-\frac{1}{2}}N_h + N_{E_{11}} + k_{Tr}N_{Tr_{11}^+} \quad (4)$$

where, the $N_X$ (X=$E_{11}$, $E_{11,2}$, $Tr^+_{11}$, or h$^+$) values correspond to the densities (/100 nm) of these quasi-particles, $k_{10}$=0.022 ps$^{-1}$ is the intrinsic first-order decay rate constant for bright singlet excitons in (6,5) SWNTs, $k_{21}$=23 ps$^{-1}$ is the rate constant for the first-order decay from the second to the first exciton sub-band(10), $k_{Tr}$ is the first-order decay rate constant of trions, $k_{EEA}t^{-1/2}$ is the EEA rate constant, and $k_{E-Tr}t^{-1/2}$ is the trion formation rate constant. Note that: (i) the $t^{-1/2}$ dependence of EEA and hole trion formation processes originate from 1D diffusion; (ii) $k_{E-Tr}$=$k_{EEA}$/2$\sqrt{2}$; and (iii) to is fitting parameter for time zero.

3.b. Extraction of Trion Transient Signal and Fitting Description.

FIG. 23 shows two-dimensional pump-probe spectral data for hole-doped S-PBN(b)-Ph5-[(6,5) SWNT]. Two-dimensional pump-probe spectral data was acquired in the NIR spectral domain (900-1350 nm). The signal intensity Δabsorption is given by the color scale on the right. The $E^+_{00} \rightarrow E^+_{11}$ bleach, $Tr^+_{11} \rightarrow Tr^+_{nm}$ transient absorption, and fast-decay NIR transient signal are highlighted as "2", "3", and "1", respectively. Experimental conditions: solvent=D2O, T=293 K, magic angle polarization, [h+]~14 (100 nm)$^{-1}$, λPump=1000 nm, pump fluence=140.0 µJ cm$^{-2}$.

FIG. 24 shows two-dimensional pump-probe spectral data for neutral S-PBN(b)-Ph5-[(6,5) SWNTs]. Two-dimensional pump-probe spectral data was acquired in the NIR spectral domain (900-1350 nm). The signal intensity Δabsorption is given by the color scale on the right. The fast-decay NIR transient signal is highlighted as "1". Experimental conditions: solvent=D2O, T=293 K, magic angle polarization, λPump=1000 nm, pump fluence=140.0 J cm$^{-2}$.

FIG. 25 shows a linear absorption spectrum for hole-doped S-PBN(b)-Ph5-[(6,5) SWNTs]. The linear absorption spectrum of hole-doped SWNTs was acquired over the 850-1300 nm spectral domain. Gaussian peak analysis was exploited to acquire the peak information for $E^+_{00} \rightarrow E^+_{11}$ transition. Experimental conditions: solvent=D2O, T=293 K.

As shown in FIG. 23, overlap of transient signals was observed in the spectral domain of 1100-1350 nm, these include the $E^+_{00} \rightarrow E^+_{11}$ bleach (highlighted as "2"), $Tr^+_{11} \rightarrow Tr^+_{nm}$ transient absorption (highlighted as "3"), and a fast-decay near-infrared transient signal (highlighted as "1"). An accurate fitting of trion kinetics requires signal separation among "1", "2", and "3". Gaussian peak analyses were exploited to accomplish such signal separations. Gaussian peak deconvolution analyses involving multiple peaks without boundary conditions can lead to arbitrary fitting results that do not reflect real peak information. To avoid such possible fitting "errors", the general peak information (including photon energy at peak maximum [$hv_{Max}$], and peak full-width at half maximum [FWHM]) for (i) signal "1", and "2" was acquired, while keeping the peak information of signal "3" as a free parameter in the fitting. Note that, (i) $hv_{Max}$ and FWHM for signal "1", the fast-decay broad NIR transient absorption signal of hole-doped SWNTs, can be obtained from the transient spectral data of neutral SWNTs (identical excitation conditions as that for hole-doped SWNTs samples), as that highlighted by "1" in FIG. 24; (ii) $hv_{Max}$ and FWHM for signal "2", the $E^+_{00} \to E^+_{11}$ bleach signal of hole-doped SWNTs, can be obtained from the linear absorption spectrum of the corresponding sample, as shown in FIG. 25.

The following Gaussian distribution function was used to accomplish the spectral fitting for selective time delays:

$$f(x, \mu_i, \sigma_i, A_i) = A_1 \frac{1}{\sigma_1 \sqrt{2\pi}} e^{-1/2 \left(\frac{x-\mu_1}{\sigma_1}\right)^2} + A_2 \frac{1}{\sigma_2 \sqrt{2\pi}} e^{-1/2 \left(\frac{x-\mu_2}{\sigma_2}\right)^2} + A_3 \frac{1}{\sigma_3 \sqrt{2\pi}} e^{-1/2 \left(\frac{x-\mu_3}{\sigma_3}\right)^2} + y_0 \quad (5)$$

where x is the photon energy (unit in eV) as variable, $\mu_i$ is the expected value ($hv_{Max}$) of the $i^{th}$ signal, $\sigma_i$ is related to FWHM of the $i^{th}$ signal by FWHM=$2\sqrt{2\ln 2}\sigma$, $A_i$ is the peak area of the $i^{th}$ signal, and $y_0$ is an offset (viewed as baseline). Utilizing such a Gaussian function while applying boundary conditions for signal "1" and "2" (acquired as noted above) allows successful signal extraction for trion transient absorption at selected time delays.

FIGS. 26A-26C show two-dimensional mapping of separated transient signals in the NIR domain. FIG. 26A shows extracted transient signals for $E^+_{00} \to E^+_{11}$ bleach. FIG. 26B shows extracted transient signals for $Tr^+_{11} \to Tr^+_{nm}$ absorption. FIG. 26C shows extracted transient signals for the fast-decay NIR absorption as highlighted in FIG. 25. Note: (i) data processing range spans the time domain of 0.07-5.48 ps, and the spectral domain of 1080-1350 nm; (ii) data processing was accomplished based with equation (5) using Python for coding; (iii) certain extremely noisy data points were removed from this analysis.

FIGS. 26A-26C display the separated signal for "1", "2", and "3" at selected time delays. It should be noted that the $E_{00} \to E_{11}$ bleaching signal was not involved in this signal processing, as it is intrinsically well separated from "1", "2", and "3" (i.e. signals in the energy domain of 0.918-1.148 eV were treated with Gaussian peak analyses). Likewise, dynamical analyses for SWNT samples with varying hole-doping levels can all be accomplished in the similar manner as described above. The transient absorption spectra for SWNTs samples with [h+]=0.3, 0.7, 3.5, and 6.1 (100 nm)$^{-1}$ are also provided in FIGS. 27A-27D.

In particular, FIGS. 27A-27D show two-dimensional pump-probe spectra for S-PBN(b)-Ph5-[(6,5) SWNT] having varying [h+]. FIG. 27A shows two-dimensional pump-probe spectra of hole-doped SWNTs with [h+]=0.3 (100 nm)$^{-1}$. FIG. 27B shows two-dimensional pump-probe spectra of hole-doped SWNTs with [h+]=0.7 (100 nm)$^{-1}$. FIG. 27C shows two-dimensional pump-probe spectra of hole-doped SWNTs with [h+]=3.5 (100 nm)$^{-1}$. FIG. 27D shows two-dimensional pump-probe spectra of hole-doped SWNTs with [h+]=6.1 (100 nm)$^{-1}$. Experimental conditions: solvent=D2O, T=293 K, magic angle polarization, λPump=1000 nm, pump fluence=140.0 μJ cm$^{-2}$.

Data fitting for each kinetic trace starts from $t_{delay}$=130 fs. Initial values for the densities of $E_{11}$ excitons ([$E_{11}$]), $E_{11}$ excitons in the second manifold ([$E_{11,2}$]), trions ([$Tr^+_{11}$]) and hole polarons ([h$^+$]) were required in order to numerically solve these ordinary differential equations (ODEs). The initial values for [$E_{11,2}$] and [$Tr^+_{11}$] are set as zero, while the initial values for [$E_{11}$] and [h$^+$] can be experimentally determined (details see Section 2). The fitting is accomplished by using the nonlinear curve-fitting function ('lsqcurvefit') coupled with 'ODE45' function in MATLAB. Curve-fitting ranges from $t_{delay}$=100 fs to $t_{delay}$=20 ps.

FIGS. 28A and 28B show numerical solutions for [$E_{11}$], [$E_{11,2}$], [$Tr^+_{11}$], and [h+]. FIG. 28A shows numerical solutions for [$E_{11}$], [$E_{11,2}$], [$Tr^+_{11}$], and [h+] obtained by fitting hole-doped S-PBN(b)-Ph5-[(6,5) SWNT] ([h+]~14.0 (100 nm)$^{-1}$) using equations (1)-(4). Initial values are provided as following: [$E_{11}$]=0.7 (100 nm)$^{-1}$, [$E_{11,2}$]=0.0 (100 nm)$^{-1}$, [$Tr^+_{11}$]=0.0 (100 nm)$^{-1}$, [h+]=14.0 (100 nm)$^{-1}$. FIG. 28B shows the same data plot as FIG. 28A but with population densities of the corresponding species being normalized.

In particular, numerical solutions of these ODEs are plotted as decay curves for $E_{11}$ excitons, $E_{11}$ excitons in the second manifold, trions and hole polarons, as shown in FIG. 28A ([$E_{11}$]~0.7 (100 nm)$^{-1}$, [h$^+$]~14 (100 nm)$^{-1}$). In this regard, it is noted that although there is no direct spectroscopic signature for monitoring the population densities for $E_{11}$ excitons in the second manifold and hole polarons, these numerical solutions provided a track for the historical changes of [$E_{11,2}$] and [h$^+$] that are not spectroscopically measurable.

3.c. Trion Formation and Decay Rate Constants.

3.c.1. Rate Constants Acquired Based on Diffusion-Controlled Trion Formation Process.

FIG. 29 shows hole trion formation and decay rate constants as a function of both [h+] and t.

Trion formation and decay dynamics are presented by 2-D plot at a selected time point ($t_{delay}$=0.5 ps) for a parallel comparison between trion formation rate constant ($k_{E-Tr} t^{-1/2} N_{h+}$) and trion decay rate constant ($k_{Tr}$). In fact, as $k_{E-Tr} t^{-1/2} N_{h+}$ varies as a function of both [h$^+$] and t, the 3-D plot of FIG. 29 conveys a more comprehensive picture of these trion dynamics. As trion decay is a first order process, the corresponding rate constant is not varying as a function of time and [h$^+$]. In contrast, trion formation rate constant ($k_{E-Tr} t^{-1/2} N_{h+}$) not only varies as a function a time, but also, at each selected time point, changes its value based on the [h$^+$] characteristic of that time. These FIG. 29 data are clearly congruent with the conclusion that trions are formed via migration of excitons to stationary hole polaron sites, while these states decay in a first-order manner.

3.c.2. Trion Dynamics Examined Based on a Non-Diffusive Model.

A non-diffusive trion formation model has also been examined here. The corresponding ODEs can be derived as below:

$$\frac{dN_{E_{11}}}{dt} = -k_{10} N_{E_{11}} - k_{EEA}(t-t_0)^{-\frac{1}{2}} N_{E_{11}}^2 + k_{21} N_{E_{11,2}} - k_{E-Tr} N_h N_{E_{11}} \quad (6)$$

$$\frac{dN_{E_{11,2}}}{dt} = \frac{1}{2} k_{EEA}(t-t_0)^{-\frac{1}{2}} N_{E_{11}}^2 - k_{21} N_{E_{11,2}} \quad (7)$$

$$\frac{dN_{Tr_{11}^+}}{dt} = k_{E-Tr}N_h + N_{E_{11}} - k_{Tr}N_{Tr_{11}^+} \quad (8)$$

$$\frac{dN_h^+}{dt} = -k_{E-Tr}N_h + N_{E_{11}} + k_{Tr}N_{Tr_{11}^+} \quad (9)$$

Compared to the diffusion-controlled model (equation (1)-(4)), this non-diffusive model lacks a time-dependent term $(t-t_0)^{-1/2}$ in the trion formation rate constant. The suitability of these two models can be evaluated based on their standard deviations (σ).

FIGS. 30A and 30B show plots of standard deviations of diffusion-controlled vs non-diffusive models as a function of hole polaron density. FIG. 30A shows standard deviations of exciton dynamical data fitting based on a diffusion-controlled trion formation model and a non-diffusive trion formation model. FIG. 30B shows standard deviations from trion dynamical data fitting based on a diffusion-controlled trion formation model and a non-diffusive trion formation model.

FIGS. 31A-31D show numerical fitting of the diffusion-controlled vs non-diffusive models in the low hole density regime. FIGS. 31A and 31B show diffusion-controlled vs non-diffusive model fitting of exciton and trion dynamical data at $[h+]\sim 0.3$ $(100 \text{ nm})^{-1}$. FIGS. 31C and 31D show diffusion-controlled vs non-diffusive model fitting of exciton and trion dynamical data at $[h+]\sim 0.7$ $(100 \text{ nm})^{-1}$.

FIGS. 32A-32F show numerical fitting of diffusion-controlled vs non-diffusive models in the medium-to-high hole density regime. FIGS. 32A and 32B show diffusion-controlled vs non-diffusive model fitting of exciton and trion dynamical data at $[h+]\sim 3.5$ $(100 \text{ nm})^{-1}$. FIGS. 32C and 32D show diffusion-controlled model vs non-diffusive model fitting of exciton and trion dynamical data at $[h+]\sim 6.1$ $(100 \text{ nm})^{-1}$. FIGS. 32E and 32F show diffusion-controlled model vs non-diffusive model fitting of exciton and trion dynamical data at $[h+]\sim 14.3$ $(100 \text{ nm})^{-1}$.

As can be seen in FIGS. 30A and 30B, these two models display quite similar σ values for fitting the exciton and trion dynamics in the low hole density regime (i.e. $[h+]\sim 0.3$-$0.7$ $(100 \text{ nm})^{-1}$); however, fitting of the dynamical data in the medium-to-high hole density regime (i.e. $[h+]\sim 3.5$-$14.3$ $(100 \text{ nm})^{-1}$) clearly shows that the diffusion-controlled trion formation model manifests significantly smaller σ values relative to the non-diffusive model (see FIGS. 31A-32F for raw data and fitting curves). In this regard, the diffusion controlled model mathematically displays global suitability for reproducing the experimentally determined exciton and trion dynamics, while the non-diffusive model is only capable of reproducing the dynamics when trion formation makes a minor contribution to the overall exciton decay dynamics (i.e. in low hole doping regime).

Furthermore, the non-diffusive model generates unrealistic fitting parameters. For example, for $[h+]\sim 14.3$ $(100 \text{ nm})^{-1}$ dynamical data, the non-diffusive model results in $k_{EEA} \sim 1.66 \times 10^4$ nm s$^{-0.5}$, corresponding to $D_{E11} \sim 2.7 \times 10^{-7}$ cm$^2$ s$^{-1}$, a value many orders of magnitude removed from the independently established exciton diffusion constants in SWNTs. Also, for the first-order trion decay process, the diffusion-controlled model gives rise to an average (from all $[h^+]$) trion decay rate constant of $\sim 0.42$ ps$^{-1}$, a value close to the result ($\sim 0.36$ ps$^{-1}$, averaged from all $[h^+]$) from simple single exponential fitting of the trion decay dynamics, thus mathematically making sense (as a simple single exponential model corresponds to a first-order process described in the diffusion-controlled model). In the non-diffusive model, although trion decay maintains the same form as that in the diffusion-controlled model, i.e. $k_{Tr-E}N_{Tr11}^+$, the lack of the $(t-t_0)^{-1/2}$ term in the description of trion formation mathematically forces a fit for the average $k_{Tr-E}$ of $\sim 0.9$ ps$^{-1}$, which is incongruent with simple inspection of the data. These fitting results point to the fact that compared to the non-diffusive trion formation model, a diffusion-controlled trion formation model is more appropriately describes the exciton and trion dynamical data acquired for hole-doped SWNTs.

4. Evaluation of Exciton-to-Trion Conversion.

4.a. Simple Qualitative Estimation of the Exciton-to-Trion Conversion Yield.

It is noted that the exciton-to-trion formation quantum yield ($\Phi_{E-Tr}$) may be directly estimated from the relation $\Phi_{E-Tr} \sim k_{E-Tr}/(k_{E-Tr}+k_{EEA}+k_{10})$, where $k_{E-Tr}$ is trion formation rate constant, $k_{EEA}$ is EEA rate constant, and $k_{10}$ is the intrinsic first-order decay rate constant for singlet exciton. Here, a simple bi-exponential function may be used to fit the trion transient absorption signal for obtaining a phenomenological $k_{E-Tr}$ in the dimension of ps$^{-1}$ (this value is $\sim 2.38$ ps$^{-1}$). The phenomenological $k_{EEA}$ and $k_{10}$ were readily acquired from bi-exponentially fitting the neutral SWNTs $E_{11}$ kinetic trace, which are $\sim 0.67$ ps$^{-1}$ and 0.048 ps$^{-1}$, respectively. Therefore, $\Phi_{E-Tr} \sim 2.38$ ps$^{-1}$/(2.38 ps$^{-1}$+0.67 ps$^{-1}$+0.048 ps$^{-1}$)=0.77.

Additionally, if the $E_{11}$ exciton bleaching signature dynamics of heavily hole-doped (e.g. $[h^+]\sim 6.1$-$14.3$ $(100 \text{ nm})^{-1}$) SWNTs samples were fitted bi-exponentially, a fast decay time constant, whose value is close to the bi-exponentially-fitted trion formation time constant of the same sample, can always been obtained; this fast decay components depletes at least 70% of $E_{11}$ exciton population. Based on this simple dynamical correlation and the above estimated $\Phi_{E-Tr}$ (without applying any complex models), it is estimated that the lower limit for exciton-to-trion conversion in (6,5) SWNTs with $[h^+]\sim 6.1$-$14.3$ $(100 \text{ nm})^{-1}$ should be $\sim 70\%$. Additionally, in the absence of any mathematical model, the dynamical correlation between the decay of $E_{11}$ excitons and rise of trions may be directly visualized by looking at the raw kinetic data in FIG. 4, particularly for the initial $\sim 1$ ps.

Note that this qualitative analysis is congruent with the notion that trion formation serves as the dominant decay channel that depletes excitons in SWNTs where $[h^+]$ ranges from 6.1-14.3 $(100 \text{ nm})^{-1}$.

4.b. A Quantitative Estimation on Exciton-to-Trion Conversion Yield Based on Numerical Simulation.

Based on equations 1-4, the exciton decay rate in hole-doped SWNTs is determined by $(d_{NE11}/dt)_{decay}=(-k_{10}N_{E11})+(-k_{EEA}t^{-1/2}N_{E11}^2)+(-k_{E-Tr}t^{-1/2}N_{h+}N_{E11})$, wherein $(-k_{10}N_{E11})$, $(-k_{EEA}t^{-1/2}N_{E11}^2)$, and $(-k_{E-Tr}t^{-1/2}N_{h+}N_{E11})$ represent the excitons decay channels through excitons intrinsic first-order decay, EEA, and trion formation, respectively (note, $t=t-t_0$). Among the parameters, $k_{10}$ is a constant acquired from experiment, $k_{EEA}$ and $k_{E-Tr}$ are acquired from fitting the exciton and trion dynamics, $N_X$ (X=h$^+$, or $E_{11}$) are the numerical solutions of equations 1-4 following fitting the excitons and trions dynamics. As such, the exciton decay rates through different decay channels can be plotted.

FIGS. 33A-33C show plots of exciton decay rate evaluated as a function of exciton intrinsic decay, EEA, and trion formation decay channels. FIG. 33A shows excitons intrinsic decay rate, EEA rate, and trions formation rate as a function of time, initial $[h+]=14.3$ $(100 \text{ nm})^{-1}$. FIG. 33B shows excitons intrinsic decay rate, EEA rate, and trions formation rate as a function of time, initial [h+]=6.1 (100 nm)$^{-1}$. FIG. 33C shows excitons intrinsic decay rate, EEA rate, and trions formation rate as a function of time, initial [h+]=3.5 (100 nm)$^{-1}$. As can be seen in FIGS. 33A-33C, for [h$^+$]~6.1-14.3 (100 nm)$^{-1}$, trions formation predominates in excitons decay channels, while for [h$^+$]≤3.5 (100 nm)$^{-1}$, EEA process starts to compete with the trion formation process in exciton decay channels. The $\Phi_{E-Tr}$ (exciton-to-trion conversion yield) can further be quantified by comparing the integration area of the different decay channels shown in FIGS. 33A-33C. Particularly, for [h$^+$]~14.3 (100 nm)$^{-1}$, $\Phi_{E-Tr}$=0.91; for [h$^+$]~6.1 (100 nm)$^{-1}$, $\Phi_{E-Tr}$=0.80; while for [h$^+$]~3.5 (100 nm)$^{-1}$, $\Phi_{E-Tr}$=0.48. Such $\Phi_{E-Tr}$ determinations are highly consistent with the above qualitative estimations, and they point to the conclusion that under appropriate hole-doping densities (i.e. [h$^+$]~6.1-14.3 (100 nm)$^{-1}$), exciton-to-trion conversion yield can approach unity.

5. Examination of Excitation Wavelength Dependence.

FIGS. 34A and 34B show representative transient absorption spectra obtained for heavily hole-doped S-PBN(b)-Ph5-[(6,5) SWNTs] following excitation at 1000 nm (excitation photon flux: 9.1×1011 pulse$^{-1}$). FIG. 34A shows transient absorption spectra at selected time delays for heavily hole-doped S-PBN(b)-Ph5-[(6,5) SWNTs] following excitation at 1000 nm (excitation photon flux: 9.1×1011 pulse-1). FIG. 34B shows transient absorption spectra at selected time delays for heavily hole-doped S-PBN(b)-Ph5-[(6,5) SWNTs] following excitation at 1130 nm (excitation photon flux: 1.1×1012 pulse$^{-1}$). Experimental conditions: [h+]=14.0 (100 nm)$^{-1}$, solvent=D2O, T=293 K, magic angle polarization.

FIG. 35 shows kinetic traces representative of dynamics for $E_{11}$ excitons and hole trions in heavily hole-doped S-PBN(b)-Ph5-[(6,5) SWNTs]. Representative kinetic traces selected at lProbe=1000 nm (representative of $E_{00} \rightarrow E_{11}$ transition; lPump=1000 nm: black, lPump=1130 nm: green) and lProbe=1190 nm (representative of $Tr^+_{11} \rightarrow Tr^+_{nm}$ transition; lPump=1000 nm: red, lPump=1130 nm: orange) in ps time-domain for hole-doped S-PBN(b)-Ph5-[(6,5) SWNT] ([h+]=14.0 (100 nm)$^{-1}$). Kinetic curves are plotted with absolute ΔAbsorption being normalized.

To examine the nature of the 1150 nm-centered absorption band, the sample was optically excited hole-doped ([h$^+$]~14 (100 nm)$^{-1}$)S-PBN(b)-Ph$_5$-[(6,5) SWNT] with a pump wavelength of 1130 nm, and pump photon flux of 1.1×10$^{12}$ pulse$^{-1}$. The corresponding transient spectra and selected single-wavelength kinetic traces are presented in comparison with that obtained from optical excitation at 1000 nm (photon flux: 9.1×10$^{11}$ pulse$^{-1}$) (see FIGS. 34A-34B and FIG. 35, respectively). As can be seen in these spectra and kinetic traces, no evident differences can be observed. Again, it is denoted that the ~1190 nm absorption band observed in hole-doped SWNTs as an $E^+_{00} \rightarrow E^+_{11}$ transition. Optical pumping at this band should generate lower-energy (relative to the energy of En exciton) excitons that are diffusive in nature. Such excitons can interact with hole polarons and form trions. Congruent with this interpretation, it is observed that the fact that optically pumping at 1190 nm with a photon flux close to that of pumping at 1000 nm gave rise to similar trion transient signal intensity relative to that obtained under 1000 nm optical pump, even though the oscillator strength of $E^+_{00} \rightarrow E^+_{11}$ transition is about twice as that of the $E_{00} \rightarrow E_{11}$ transition at 1130 nm (see FIG. 25).

6. Laser Pulse Characterization and Nature of the $E_{00} \rightarrow E_{11}$ Optical Pumping.

FIGS. 36A-36C show characterizations of excitation laser pulse. FIG. 36A shows 1.24 eV energy laser pulse characterized using a fiber optic path cable (Ocean Optics); FIG. 36B shows a plot at; the FWHM (0.012 eV) and center energy (Xc~1.24 eV) of the laser pulse, fitted by a Gaussian function. FIG. 36C shows overlap of the 1.24 eV laser pulse with the deconvoluted steady-state absorption spectra of hole-doped SWNTs as shown in FIG. 25. The data were collected using Ocean Optics SpectraSuite software.

The deconvoluted steady-state absorption spectra shown in FIG. 25 point to the fact that SWNTs with chiralities other than (6,5) are present and contributed to the electronic absorption spectrum of the ground-state sample in the spectral domain of 900-1300 nm. To address the potential issue that transient optical signals following (6,5) SWNTs $E_{00} \rightarrow E_{11}$ optical pumping could be contaminated by the transient absorptive contributions of other SWNT species other than (6,5) SWNTs, the laser pulse with the TOPAS output was set to 1.24 eV, and the corresponding laser pulse shape is shown in Fig. P2S16. As can be seen in FIGS. 36A-36C, the 1.24 eV laser pulse display maximum overlap with (6,5) SWNT $E_{00} \rightarrow E_{11}$ transition, and is energetically separated from the corresponding $E_{00} \rightarrow E_{11}$ transitions of SWNTs of other chiralities (the combined concentration of which are one order of magnitude smaller than the (6,5) SWNT population); thus, these other SWNT populations will in no way impact the transient signal analysis of (6,5) SWNT excitonic dynamics.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. An optoelectronic system comprising:
   a single walled carbon nanotube (SWNT) device, the SWNT device comprising a SWNT with a carrier-doping density; and
   a stimuli generator capable of generating an optical, electrical, or magnetic stimuli, wherein the stimuli is capable of control of trion formation.

2. The optoelectronic system of claim 1 wherein the carrier-doping density comprises a hole-polaron or electron-polaron concentration.

3. The optoelectronic system of claim 2, wherein the hole-polaron or electron-polaron concentration is in a range of about 6.1 to about 14.3 (100 nm)$^{-1}$.

4. The optoelectronic system of claim 1, wherein the trion formation is characterized by a trion response to a magnetic field.

5. The optoelectronic system of claim 1, wherein the trion formation is characterized by a trion response to an electrical input.

6. The optoelectronic system of claim 1, wherein the trion formation is characterized by a trion response to an optical input.

7. The optoelectronic system of claim 1, wherein the trion formation is characterized by a trion migration rate to an electrode.

8. The optoelectronic system of claim 1, wherein the trion formation is characterized by a SWNT trion transient absorptive signature ($Tr^+_{11} \rightarrow Tr^+_{nm}$ or $Tr^-_{11} \rightarrow Tr^-_{nm}$).

9. The optoelectronic system of claim 1, wherein the SWNT device includes photogenerated free-carriers, wherein the photogenerated free-carriers are quantified according to $$\frac{N_{Tr+/-11}}{2N_{Ex}},$$

where $N_{Ex}$ is an exciton density (per 100 nm) produced following $E_{00} \rightarrow E_{nm}$ excitation, and $N_{Tr+/-11}$ represents a maximum trion density following optical excitation, reflecting a combined $N_{Tr+11}$ and $N_{Tr-11}$ positive and negative trion densities.

10. The optoelectronic system of claim 9, wherein $N_{Tr+/-11}$ is calculated using $A = \sigma_{Tr} l C_{SWNT} N_A L_{SWNT} N_{Tr+/-11}$, where A is the absorbance corresponding to the $Tr_{+/-11} \rightarrow Tr_{+/-nm}$ transition, $\sigma Tr$ is the absorption cross section associated with the $Tr_{+/-11} \rightarrow Tr_{+i-nm}$ transition, l is an optical path length of a spectral cuvette, $C_{SWNT}$ is a SWNT molar concentration, NA is the Avogadro constant, and $L_{SWNT}$ is an average length of the SWNTs used for the SWNT device.

\* \* \* \* \*